US008663966B2

(12) United States Patent
Kragh et al.

(10) Patent No.: US 8,663,966 B2
(45) **Date of Patent: *Mar. 4, 2014**

(54) POLYPEPTIDE

(75) Inventors: Karsten Matthias Kragh, Viby J (DK); Bo Spange Sørensen, Skanderborg (DK)

(73) Assignee: Dupont Nutrition Biosciences APS, Copenhagen (DK)

( * ) Notice: Subject to any disclaimer, the term of this patent is extended or adjusted under 35 U.S.C. 154(b) by 1041 days.

This patent is subject to a terminal disclaimer.

(21) Appl. No.: 11/857,691

(22) Filed: Sep. 19, 2007

(65) Prior Publication Data

US 2008/0107773 A1 May 8, 2008

Related U.S. Application Data

(62) Division of application No. 10/886,023, filed on Jul. 7, 2004, now Pat. No. 7,371,552.

(60) Provisional application No. 60/485,413, filed on Jul. 7, 2003, provisional application No. 60/485,616, filed on Jul. 7, 2003.

(51) Int. Cl.

| | |
|---|---|
| ***C12N 9/28*** | (2006.01) |
| ***C12N 15/00*** | (2006.01) |
| ***C12N 9/88*** | (2006.01) |

(52) U.S. Cl.

USPC ........... 435/202; 435/200; 435/204; 435/69.1

(58) Field of Classification Search

None

See application file for complete search history.

(56) References Cited

U.S. PATENT DOCUMENTS

| | | | |
|---|---|---|---|
| 4,683,202 | A | 7/1987 | Mullis |
| 4,946,779 | A | 8/1990 | Kameda et al. |
| 5,204,254 | A | 4/1993 | Schmid et al. |
| 5,958,749 | A | 9/1999 | Kubota et al. |
| 5,989,169 | A | 11/1999 | Svendsen et al. |
| 6,162,628 | A | 12/2000 | Cherry et al. |
| 6,242,224 | B1 | 6/2001 | Nakano et al. |
| 6,667,065 | B1 | 12/2003 | Kragh et al. |
| 7,166,453 | B2 | 1/2007 | Kragh et al. |
| 7,371,552 | B2 * | 5/2008 | Kragh et al. .................. 435/202 |
| 2003/0134395 | A1 | 7/2003 | Shetty et al. |
| 2005/0059131 | A1 | 3/2005 | Bisgard-Frantzen et al. |
| 2005/0136524 | A1 | 6/2005 | Kragh et al. |
| 2005/0137111 | A1 | 6/2005 | Kragh et al. |
| 2006/0008888 | A1 | 1/2006 | Kragh et al. |
| 2006/0008890 | A1 | 1/2006 | Kragh et al. |
| 2006/0018997 | A1 | 1/2006 | Kragh et al. |
| 2006/0073583 | A1 | 4/2006 | Kragh et al. |
| 2007/0020727 | A1 | 1/2007 | Berg et al. |
| 2007/0020731 | A1 | 1/2007 | Kragh et al. |
| 2007/0072270 | A1 | 3/2007 | Kragh et al. |
| 2007/0141693 | A1 | 6/2007 | Berg et al. |
| 2008/0107773 | A1 | 5/2008 | Kragh et al. |
| 2008/0227173 | A1 | 9/2008 | Berg et al. |
| 2008/0274531 | A1 | 11/2008 | Berg et al. |
| 2008/0292747 | A1 | 11/2008 | Berg et al. |

FOREIGN PATENT DOCUMENTS

| | | |
|---|---|---|
| EP | 120 693 | 3/1984 |
| EP | 0 298 645 | 1/1989 |
| EP | 0 412 607 | 2/1991 |
| EP | 0 494 233 | 4/1991 |
| JP | 6-279745 | 10/1994 |
| JP | 6-279746 | 10/1994 |
| JP | 8-205865 | 8/1996 |
| JP | 2000-245466 | 9/2000 |
| WO | WO 91/04669 | 4/1991 |
| WO | WO 99/23211 | 5/1999 |
| WO | 99/50399 | 10/1999 |
| WO | WO 00/58447 | 10/2000 |
| WO | WO 01/04273 | 1/2001 |
| WO | 02/068589 | 9/2002 |
| WO | WO 2004/091544 | 10/2004 |
| WO | WO 2004/111217 | 12/2004 |
| WO | WO 2005/003339 | 1/2005 |
| WO | WO 2005/007818 | 1/2005 |
| WO | WO 2005/007867 | 1/2005 |
| WO | WO 2006/003461 | 1/2006 |
| WO | PCT US2004/021723 | 6/2007 |

OTHER PUBLICATIONS

Chica et al. Curr Opin Biotechnol. Aug. 2005;16(4):378-84.*

Witkowski et al. Biochemistry. Sep. 7, 1999; 38(36): 11643-50.*

Seffernick et al. J Bacteriol. Apr. 2001; 183 (8): 2405-10.*

U.S. Appl. No. 11/887,977, filed Oct. 5, 2007, Berg et al.

U.S. Appl. No. 12/339,718, filed Dec. 19, 2008, Derkx et al.

Yoshiyuki Takasaki, "Production of Maltohexaose by α-Amylase from *Bacillus circulans* G-6", Agric. Biol. Chem., vol. 46, No. 6, 1982, pp. 1539-1547.

Hajime Taniguchi et al., "Purification of *Baccillus circulans* F-2 Amylase and Its General Properties", Agric. Biol. Chem. vol. 47, No. 3, 1983, pp. 511-519.

Francis J. Bealin-Kelly et al., "The α-amylase of the caldoactive bacterium *Bacillus caldovelox*", Biochemical Society Transactions, vol. 18, No. 2, 1990, pp. 310-311.

William M. Fogarty et al., "A novel maltohexaose-forming α-amylase from *Bacillus caldovelox*: patterns and mechanisms of action", Appl Microbiol Biotechnol, 1991, vol. 36, pp. 184-189.

Narimasa Saito, "A Thermophilic Extracellular α-Amylase from *Baccilus licheniformis*", Archives of Biochemistry and Biophysics, vol. 155, 1973, pp. 290-298.

(Continued)

*Primary Examiner* — Tekchand Saidha

*Assistant Examiner* — MD. Younus Meah

(74) *Attorney, Agent, or Firm* — Vedder Price P.C.; Thomas J. Kowalski; Smitha B. Uthaman

(57) ABSTRACT

We disclose a food additive comprising a PS4 variant polypeptide, in which the PS4 variant polypeptide is derivable from a parent polypeptide having non-maltogenic exoamylase activity, in which the PS4 variant polypeptide comprises substitutions at the following positions: G121D, 134, 141, 157, 223, 307 and 334 with reference to the position numbering of a *Pseudomonas saccharophilia* exoamylase sequence shown as SEQ ID NO: 1.

27 Claims, 4 Drawing Sheets

(56) References Cited

OTHER PUBLICATIONS

Hajime Taniguchi "Matohexaose-Producing Amylase of *Bacillus circulans* F-2" National Food Research Institute, 1991, pp. 111-124.
Altschul et al., 1990, J. Mol. Biol. 403-410 . "Basic Local Alignment Search Tool".
Bernfeld, *Methods Enzymol.*, (1954), 1, 149-158. "Amylase, α and β."
Beucage S.L. et al.,(1981) *Tetrahedron Letters* 22, p. 1859-1869. "Deoxynucleoside Phosphoramidites-A New Class of Key Intermediates for Deoxypolynucleotide Synthesis".
Bradford, 1976, Anal. Biochem., 72, 248. "A Rapid and Senstitive Method for the Quantitation of Microgram Quantities of Protein Utilizing the Principle of Protein-Dye Binding".
Caruthers MH et al., (1980) Nuc. Acids Res. Symp. Ser. 215-23. "New Chemical Methods for Synthesizing Polynucleotides."
Devereux et al., 1984, Nuc. Acids Research 12 p. 387. "A Comprehensive set of sequence analysis programs for the VAX".
Henrissat B, Bairoch A; Biochem. J., 316,695-696 (1996)) "Updating the sequence-based classification of glycosyl hydrolases."
Higgins DG & Sharp PM (1988), Gene 73(1),237-244. "CLUSTAL: a package for performing multiple sequence alignment on a microcomputer".
Horn T. et al., 1980, Nuc. Acids Resp. Symp. Ser. 225-232. "Synthesis of Oligonucleotides on Cellulose."
Horwell DC, *Trends Biotechnol.* (1995) 13(4),132-134. "The 'peptoid' approach to the design of non-peptide, small molecule agonists and antagonists of neuropeptides."
Matthes et al., (1984) *EMBO J.* 3, p. 801-805 "Simultaneous rapid chemical synthesis of over one hundred oligonucleotides on a microscale".
Morinaga et al., (*Biotechnology* (1984) 2, p. 646-649). "Improvement of Oligonucleotide-Directed Site-Specific Mutagenesis Using Double-Stranded Plasmid DNA".
Nelson and Long, Analytical Biochemistry, 1989, 180, p. 147-151. "A General Method of Site-Specific Mutagenesis Using a Modification of the *Thermus aquaticus* Polymerase Chain Reaction".
Saiki R K et al. (*Science* (1988) 239, pp. 487-491. "Primer-Directed Enzymatic Amplification of DNA with a Thermostable DNA polymerase".
Sarkar and Sommer (*Biotechniques* (1990), 8, p. 404-407. "The "Megaprimer" Method of Site-Directed Mutagenesis".
Yoshiyuki Sakano et al., "Purification and Properties of an exo-α-Amylase from *Pseudomonas stutzer*", Agric. Biol. Chem., vol. 46, No. 3, 1982, pp. 639-646.
Yoshiyuki Takasaki et al., "Maltotetraose-producing Amylase from *Bacillus* sp. MG-4", Agric. Biol. Chem., vol. 55, No. 7, 1991, pp. 1715-1720.
Geneseq Database Accession No. ADW75735, A. Gernot, et al., Stutzeri Maltotetrahydrolase Mature Protein Seq ID 7, Apr. 7, 2005.
Geneseq Database Accession No. ADW73063, C. T. Berg, et al., Stutzeri Maltotetrahydrolase Protein Seq ID12, Apr. 7, 2005.
Geneseq Database Accession No. ADW75733, A. Gernot, et al., Saccharophilia Variant Maltotetrahydrolase Protein Seq ID 5, Apr. 7, 2005.
A.K. Chandra et al., "Production of Extracellular Thermostable α-Amylase by *Bacillus licheniformis*", J. Ferment. Technol. vol. 58, No. 1, 1980, pp. 1-10.
R.A.K. Srivastava et al., "Culture Conditions for Production of Thermostable Amylase by *Bacillus stearothermophilus*", Applied and Environmental Microbiology, Jul. 1986, pp. 179-184.
Veronique Planchot et al.., "Purification and characterization of extracellular alpha-amylase from *Aspergillus fumigatus*", Carbohydrate Research, vol. 272, 1995, pp. 97-109.
Ohnishi et al., "General Consideration for Conditions and Methods of Amylase Assay", Handbook of Amylases and Related Enzymes, The Amylase Research Society of Japan, 1988, pp. 10-14.
Kim L. Larsen et al., "Purification and characterization of cyclodextrin glycosyltransferase from *Paenibacillus* sp. F8", Carbohydrate Research, vol. 310, 1998, pp. 211-219.
Helmut Blum et al., "Improved silver staining of plant proteins, RNA and DNA in polyacrylamide gels", Electrophoresis, 1987, vol. 8, pp. 93-99.
Hidetsugu Fuwa, "A New Method for Microdetermination of Amylase Activity by the Use of Amylose as the Substrate", The Journal of Biochemistry, vol. 41, No. 5, 1954, pp. 583-603.
Akira Tsukamoto et al., "Nucleotide Sequence of the Maltohexaose-Producing Amylase Gene from an Alkalophilic *Bacillus* sp. #707 and Structural Similarity to Liquefying Type α-Amylase", Biochemical and Biophysical Research Communications, vol. 151, No. 1, Feb. 29, 1988, pp. 25-31.
Y.C. Lee, "Carbohydrate analyses with high-performance anion-exchange chromatography", Journal of Chromatography A., vol. 720, 1996, pp. 137-149.
Robert N. Ammeraal et al., "High-performance anion-exchange chromatography with pulsed amperometric detection of linear and branched glucose oligosaccharides", Carbohydrate Research, vol. 215, 1991, pp. 179-192.
Greg Winter et al., "Man-made antibodies", Nature, vol. 349, 1991, pp. 293-299.
Rosario Orlandi et al.., "Cloning immunoglobulin variable domains for expression by the polymerase chain reaction", Proc. Natl. Acad. Sci. USA, vol. 86, May 1989, pp. 3833-3837.
Shun-ichi Takeda et al., "Construction of chimaeric processed immunoglobulin genes containing mouse variable and human constant region sequences", Nature, vol. 314, Apr. 1985, 452-454.
Michael S. Neuberger, et al., "Recombinant antibodies possessing novel effector functions", Nature, vol. 312, Dec. 13, 1984, pp. 604-608.
Sherie L. Morrison et al., "Chimeric human antibody molecules: Mouse antigen-binding domains with human constant region domains", Proc. Natl. Acad. Sci. USA, vol. 81, Nov. 1984, pp. 6851-6855.
J. F. Kennedy et al., "Characteristics of alpha-Amylase K, a Novel Amylase from a Strain of *Bacillus subtilis*", Starch/Starke, vol. 31, No. 3, 1979, pp. 93-99.
Sambrook, J., E. F. Fritsch, and T. Maniatis, 1989, "Molecular Cloning: A Laboratory Manual", Second Edition, Books 1-3.
S.P.C. Cole et al., "The EBV-Hybridoma Technique and Its Application to Human Lung Cancer", Monoclonal Antibodies and Cancer Therapy, 1985, pp. 77-96.
Richard J. Cote, et al., "Generation of human monoclonal antibodies reactive with cellular antigens", Proc. Natl. Acad. Sci. USA, vol. 80, Apr. 1983, pp. 2026-2030.
Danuta Kozbor et al., "The production of monoclonal antibodies from human lymphocytes", Immunology Today, vol. 4, No. 3, 1983.
Kohler et al., Nature, vol. 256, 1975, pp. 495-497 "Continuous cultures of fused cells secreting antibody of predefined specificity."
M. Antoinette Mc Tigue et al., The alkaline amylase of the alkalophilic *Bacillus* sp. IMD 370, Department of Industrial Microbiology, vol. 17, 1995, pp. 570-573.
Takaya Hayashi et al., "Properties of new alkaline maltohexaose-forming amylases", Appl Microbiol Biotechnol, vol. 28, 1988, pp. 281-285.
Tae Un Kim et al., "Purification and Characterization of a Maltotetraose-Forming Alkaline α-Amylase from an Alkalophilic *Bacillus* Strain, GM8901", Applied and Environmental Microbiology, Aug. 1995, pp. 3105-3112.
Keiji Kainuma et al., "Isolation and Action Pattern of Maltohexaose Producing Amylase From *Aerobacter Aerogenes*", FEBS Letters, vol. 26, No. 1, Oct. 1972, pp. 281-285.
Byoung-Cheol Min et al., "Cloning of Novel Maltooligosaccharide-Producing Amylases as Antistaling Agents for Bread", J. Agric. Food Chem., 1998, vol. 46, pp. 779-782.
Tadeusz Jakubezyk et al., "Scientific Transactions of the Academy of Agriculture in Warsaw", Agricultural and Food Technology, vol. 8, 1973, pp. 223-235.
Jianhua Zhou et al., "Properties of the enzyme expressed by the *Pseudomonas saccharophila* maltotetraohydrolase gene (*mta*) in *Escherichia coli*", Carbohydrate Research, vol. 223, 1992, pp. 255-261.

(56) References Cited

OTHER PUBLICATIONS

Mitsuru Monma et al. "Formation and Hydrolysis of Maltohexaose by an Extracellular Exo-maltohexaohydrolase", Agric. Biol. Chem., vol. 47, No. 8, 1983, pp. 1769-1774.

William M. Fogarty et al., "Extracellular Maltotetraose-Forming Amylase of *Pseudomonas* SP". IMD 353, Biotechnology Letters, vol. 16, No. 5, May 1994, pp. 473-478.

Katsuo Wako et al., "Purification and Some Properties of a Maltotriose-producing Amylase", J. Jap. Soc. Starch Sci., vol. 26, No. 3, 1979, pp. 175-181.

Yoshiyuki Takasaki, "An Amylase Producing Maltotriose from *Bacillus subtilis*", Agric. Biol. Chem., vol. 49, No. 4, 1985, pp. 1091-1097.

E. Ann MacGregor, "Relationship of Sequence and Structure to Specificity in the α-amylase family of Enzymes", Biochimica et Biphysica Acta 1546 (2001) p. 1-20.

Simon RJ et al. *PNAS* (1992) 89(20), 9367-9371. "Peptoids: A Modular approach to drug discovery".

Smith et al., 1988, Gene 70, 351-361. "Characterization of signal-sequence-coding regions selected from the *Bacillus subtilis* chromosome".

Tatusova, T. FEMS Microbiol Lett 1999 174(2): 247-50. "BLAST 2 sequences, a new tool for comparing protein and nucleotide sequences".

Tatusova,T. FEMS Microbiol Lett 1999 177(1): 187-188. Erratum to "BLAST 2 Sequences, a new tool for comparing protein and nucleotide sequences".

Taylor W.R. (1986) "The classification of amino acid conservation" *J. Theor.Biol.* 119; 205-218.

Fujita et al. "Cloning and Nucleotide Sequence of the Gene (amyP) for Maltotetraose-Forming Amylase from *Pseudomonas stutzeri* MO-19," *J. Bactrol.* 1989, 171, 1333-1339.

Van der Maarel et al., "Properties and applications of starch-converting enzymes of the beta-amylase family," *J. of Biotechnology*, 94 (2002) pp. 137-155.

Ausubel et al., 1999, "Short Protocols in Molecular Biology", pp. 7-58 to 7-60.

Ausubel, F. M. et al. Cold Spring Harbor Laboratory Press; (1995 and periodic supplements).

Ed Harlow and David Lane "Antibodies, A Laboratory Manual", Cold Spring Harbor Laboratory Press, ISBN 0-87969-314-2, 1988.

Roskams, Jane and Linda Rodgers, "Lab Ref: A Handboook of Recipes, Reagents, and Other Reference Tools for Use at the Bench", Cold Spring Harbor Laboratory, ISBN 0-87969-630-3, 2002.

Larsson, Lars-Inge "Immunocytochemistry: Theory and Practice", CRC Press inc., Baca Raton, Florida, 1988, ISBN 0-8493-6078-1.

Seethala, Ramakrishna; Prabhavathi B. Fernandes, "Handbook of Drug Screening" vol. 114, Marcel Dekker, 2001, New York, NY, ISBN 0-8247-0562-9.

Lane, David; Ed Harlow, "Using Antibodies: A Laboratory Manual: Portable Protocol No. I" (1998, Cold Spring Harbor Laboratory Press, ISBN 0-87969-544-7).

Gait, M.J., (ed), 1984, "Oligonucleotide Synthesis: A Practical Approach", IRL Press.

Polak, J. M. and James O'D. McGee, 1990, "In Situ Hybridization: Principles and Practice".

Pound John D. (ed); "Immunochemical Protocols, vol. 80", in the series: "Methods in Molecular Biology", Humana Press, Totowa, New Jersey, 1998.

Roe, B., Crabtree, J., and A. Kahn, "Current Protocols in Molecular Biology", ch. 9, 13, and 16, John Wiley & Sons, New York, N.Y., 1996.

Hisashi Okemoto et al., "Isolation and cultivation of a novel microorganism producing a maltopentaose-forming enzyme", Appl Microbiol Biotechnol, 1986, vol. 25, pp. 137-142.

Jianhua Zhou et al., "Nucleotide sequence of the maltotetraohydrolase gene from *Pseudomonas saccharophila*", FEBS Letters, vol. 255, No. 1, 1989, 37-41, pp. 37-41.

William M. Fogarty, Department of Industrial Microbiology, University College, Dublin, Ireland, "Microbial Amylases", 1983, W.M Fogarty (Ed.) Microbial Enzymes and biotechnology, Applied Science, London, pp. 1-92.

William M. Fogarty et al., "Starch-Degrading Enzymes of Microbial Origin", Progress in Industrial Microbiology, vol. 15, M.J. Bull (Ed), Elsevier Scientific, 1979, pp. 87-150.

Keiji Kainuma et al., "Purification and some properties of a novel Maltohexaose-Producing Exo-Amylase From *Aerobacter Aerogenes*", Biochimica et Biophysica Acta, 410 (1975) 333-346.

Osamu Shida et al., "Cloning and Nucleotide Sequence of the Maltopentaose-forming Amylase Gene from *Pseudomonas* sp. KO-8940", Biosci. Biotech. Biochem. vol. 56, No. 1, pp. 76-80, 1992.

Christophersen, et al.; "Enzymatic Characterisation of Novamyl a Thermostable α-Amylase"; Starch/Stärke 50 (1998); vol. 50 (1); pp. 39-45.

Steven Mosimann et al., "A Critical Assessment of Comparative Molecular Modeling of Tertiary Structures of Proteins", Proteins: Structure, Function, and Genetics, 1995, vol. 23, pp. 301-317.

GenomeNet 1GCY, Aug. 14, 2000, High Resolution Crystal Structure Of Maltotetraose-Forming Exo-Amylase.

Damien Devos, et al., Practical Limits Of Function Prediction, Proteins: Structure, Function, and Genetics (2000) vol. 41, p. 98-107.

S. Sen, et al., Development In Directed Evolution For Improving Enzyme Functions, Applied Biochemistry and Biotechnology (2007) vol. 143, p. 212-223.

James C. Whisstock, et al., Prediction Of Protein Function From Protein Sequence And Structure, Quarterly Reviews of Biophysics (2003) vol. 36, No. 3, p. 307-340.

UniProt database Accession No. P22963, Glucan 1,4-alpha-maltotetraohydrolase, Aug. 1, 1991.

UniProt database Accession No. P22953, Glucan 1,4-alpha-maltotetraohydrolase, Aug. 1, 1991.

\* cited by examiner

POLYPEPTIDE

This application is a divisional of U.S. Application Ser. No. 10/886,023, filed Jul. 7, 2004, now U.S. Pat 7371,552, which application claims priority to U.S. provisional application Ser. Nos. 60/485,413 and 60/485,616 both filed Jul. 7, 2003, in which inventor Kragh is a co-inventor. Reference is also-made to international applications PCT/US04/0021723 and PCT/US04/21739, filed Jul. 7, 2004: designating the US, published as WO 05/007818 and WO 05/007867, respectively. (applicant: Genencor, and Reference is also made to US utility applications Ser. Nos. 10/886,903 and 10/886.905, were filed Jul. 7, 2004, in which inventor Kragh is a co-inventor.

This application also claims priority to U.S. provisional application Ser. No. 60/485,539 filed Jul. 7, 2003, in which inventor Kragh is a co-inventor. Reference is also made to international application PCT/IB2004/002487 filed Jul. 7, 2004 and designating the U.S. , published as WO 2005/003339, in which inventor Kragh is a coinventor.

The foregoing applications, and each document cited or referenced in each of the present and foregoing applications, including during the prosecution of each of the foregoing applications ("application and article cited documents"), and any manufacturer's instructions or catalogues for any products cited or mentioned in each of the foregoing applications and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text for in any document here by incorporated into this text, are hereby incorporated herein by reference. Documents incorporated by reference into this text or any teachings therein may be used in the practice of this invention. Documents incorporated by reference into this text are not admitted to be prior art.

FIELD

This invention relates to polypeptides, and nucleic acids encoding these, and their uses as non-maltogenic exoamylases in producing food products. In particular, the polypeptides are derived from polypeptides having non-maltogenic exoamylase activity, in particular, glucan 1,4-alpha-maltotetrahydrolase (EC 3.2.1.60) activity.

SUMMARY

According to a first aspect of the invention, we provide a food additive comprising a PS4 variant polypeptide, in which the PS4 variant polypeptide is derivable from a parent polypeptide having non-maltogenic exoamylase activity, in which the PS4 variant polypeptide comprises substitutions at the following positions: G121D, 134, 141, 157, 223, 307 and 334 with reference to the position numbering of a *Pseudomonas saccharophilia* exoamylase sequence shown as SEQ ID NO: 1.

Preferably, the PS4 variant polypeptide comprises one or both of substitutions at positions 121 and 223, preferably G121D and/or G223A. The position 223 substitution may also comprise G223L. More preferably, the PS4 variant polypeptide comprises one or more of: a substitution at position 33, preferably N33, more preferably N33Y, a substitution at position 34, preferably D34, more preferably D34N, a substitution at position 178 and a substitution at position 179.

Preferably, the parent polypeptide comprises a non-maltogenic exoamylase, preferably a glucan 1,4-alpha-maltotetrahydrolase (EC 3.2.1.60). Preferably, the parent polypeptide is or is derivable from *Pseudomonas* species, preferably *Pseudomonas saccharophilia* or *Pseudomonas stutzeri*. In preferred embodiments, the parent polypeptide is a non-maltogenic exoamylase, from *Pseudomonas saccharophilia* exoamylase having a sequence shown as SEQ ID: 1 or SEQ ID NO: 5. In highly preferred embodiments, the parent polypeptide is a non-maltogenic exoamylase from *Pseudomonas stutzeri* having a sequence shown as SEQ ID NO: 7 or SEQ ID NO: 11.

In highly preferred embodiments, the PS4 variant polypeptide has a higher thermostability compared to the parent polypeptide when tested under the same conditions. Preferably, the half life (t½), preferably at 60 degrees C., is increased by 15% or more, preferably 50% or more, most preferably 100% or more, relative to the parent polypeptide.

Alternatively or in addition, the PS4 variant polypeptide preferably has a higher exo-specificity compared to the parent polypeptide when tested under the same conditions. Preferably, it has 10% or more, preferably 20% or more, preferably 50% or more, exo-specificity compared to the parent polypeptide.

In further preferred embodiments, the PS4 variant polypeptide is one in which the position 134 substitution comprises G134R. The position 141 substitution preferably comprises A141P. furthermore, the position 334 substitution preferably comprises S334P.

Preferably, the PS4 variant polypeptide is one in which (a) the position 33 substitution comprises N33Y; (b) the position 34 substitution comprises D34N; (c) the position 157 substitution comprises 1157L; (d) the position 178 substitution comprises L178F; (e) the position 179 substitution comprises A179T. (f) the position 223 substitution comprises G223A; or (g) the position 307 substitution comprises H307L.

In highly preferred embodiments, the PS4 variant polypeptide comprises the substitutions: G134R, A141P, 1157L; G223A, H307L and S334P, together with phenylalanine at position 178 or threonine at position 179, or both, optionally together with one or both of N33Y and D34N.

It may further comprise a substitution at position 121. The PS4 variant polypeptide may have the sequence PSac-D34 (SEQ ID NO: 2) or the sequence PStu-D34 (SEQ ID NO: 8). The PS4 variant polypeptide may furthermore preferably be one in which the position 121 substitution comprises G121D. Preferably, the PS4 variant polypeptide has the sequence PSac-D20 (SEQ ID NO: 3) or th sequence PStu-D20 (SEQ ID NO: 9).

Further substitutions are possible. For example, the PS4 variant peptide may further comprise a substitution at position 87. The position 87 substitution preferably comprises G87. Preferably, the PS4 variant polypeptide has the sequence PSac-D14 (SEQ ID NO: 4) or the sequence PStu-D14 (SEQ ID NO: 10). The PS4 variant polypeptide may have the sequence PSac-pPD77d33.

According to a second aspect of the invention, we provide a use of a PS4 variant polypeptide as set out in the first aspect of the invention as a food additive.

According to a third aspect of the invention, we provide a process for treating a starch comprising contacting the starch with a PS4 variant polypeptide as set out above and allowing the polypeptide to generate from the starch one or more linear products.

According to a fourth aspect of the invention, we provide use of a PS4 variant polypeptide as set out in the first aspect of the invention in preparing a food product.

According to a fifth aspect of the invention, we provide a process of preparing a food product comprising admixing a polypeptide as set out in the first aspect of the invention with a food ingredient.

In preferred embodiments, the food product comprises a dough or a dough product, preferably a processed-dough product. Preferably, the food product is a bakery product.

According to a sixth aspect of the invention, we provide a process for making a bakery product comprising: (a) providing a starch medium; (b) adding to the starch medium a PS4 variant polypeptide as set out in the first aspect of the invention; and (c) applying heat to the starch medium during or after step (b) to produce a bakery product.

According to a seventh aspect of the invention, we provide a food product, dough product or a bakery product obtained by a process as described.

According to a eighth aspect of the invention, we provide an improver composition for a dough, in which the improver composition comprises a PS4 variant polypeptide as set out in the first aspect of the invention, and at least one further dough ingredient or dough additive.

According to a ninth aspect of the invention we provide a composition comprising a flour and a PS4 variant polypeptide as set out in the first aspect of the invention.

According to a tenth aspect of the invention, we provide a use of a PS4 variant polypeptide as set out in the first aspect of the invention, in a dough product to retard or reduce staling, preferably detrimental retrogradation, of the dough product.

According to a eleventh aspect of the invention, we provide a combination of a PS4 variant polypeptide as set out above, together with Novamyl, or a variant, homologue, or mutants thereof which has maltogenic alpha-amylase activity.

According to a twelfth aspect of the invention, we provide a use of a Novamyl combination as described for an application as set out above.

According to an thirteenth aspect of the invention, we provide a food product produced by treatment with a combination as described.

There is provided, according to a fourteenth aspect of the present invention, a food additive comprising a PS4 variant polypeptide, in which the PS4 variant polypeptide is derivable from a parent polypeptide having non-maltogenic exoamylase activity, in which the PS4 variant polypeptide comprises substitutions at the following positions: G121D, 134, 141, 157, G223A, 307 and 334 with reference to the position numbering of a *Pseudomonas saccharophilia* exoamylase sequence shown as SEQ ID NO: 1.

SEQUENCE LISTINGS

Figure 1:
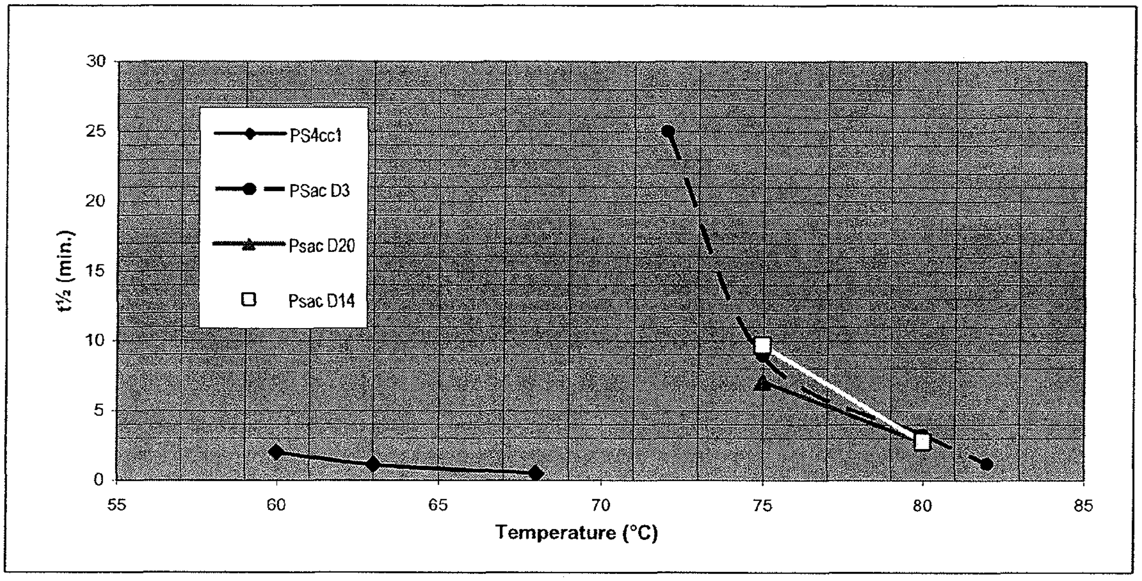
FIG. 1 is a graph showing thermostability improvement of the PS4 variants. PS4cc1 is an expressed control enzyme derived from *Pseudomonas saccharophilia*, without signal sequence and lacking the starch binding domain. Half life in minutes is plotted against temperature in degrees C. for PS4cc1, PSac-D3, PSac-D20 and PSac-D14.

SEQ ID NO: 1 shows a PS4 reference sequence, derived from *Pseudomonas saccharophila* maltotetrahydrolase amino acid sequence.

SEQ ID NO: 2 shows a PSac-D34 sequence; *Pseudomonas saccharophila* maltotetrahydrolase amino acid sequence with 11 substitutions and deletion of the starch binding domain.

SEQ ID NO: 3 shows a PSac-D20 sequence; *Pseudomonas saccharophila* maltotetrahydrolase amino acid sequence with 13 substitutions and deletion of the starch binding domain.

SEQ ID NO: 4 shows a PSac-D14 sequence; *Pseudomonas saccharophila* maltotetrahydrolase amino acid sequence with 14 substitutions and deletion of the starch binding domain.

SEQ ID NO: 5 shows a *Pseudomonas saccharophila* Glucan 1,4-alpha-maltotetrahydrolase precursor (EC 3.2.1.60) (G4-amylase) (Maltotetraose-forming amylase) (Exo-maltotetraohydrolase) (Maltotetraose-forming exo-amylase). SWISS-PROT accession number P22963.

SEQ ID NO: 6 shows a *P. saccharophila* mta gene encoding maltotetraohydrolase (EC number=3.2.1.60). GenBank accession number X16732.

SEQ ID NO:7 shows a PS4 reference sequence, derived from *Pseudomonas stutzeri* maltotetrahydrolase amino acid sequence.

SEQ ID NO. 8 shows a PStu-D34 sequence; *Pseudomonas stutzeri* maltotetrahydrolase amino acid sequence with 9 substitutions.

SEQ ID NO: 9 shows a PStu-D20 sequence; *Pseudomonas stutzeri* maltotetrahydrolase amino acid sequence with 11 substitutions.

SEQ ID NO: 10 shows a PStu-D14 sequence; *Pseudomonas stutzeri* maltotetrahydrolase amino acid sequence with 12 substitutions.

SEQ ID NO: 11 shows a *Pseudomonas stutzeri* (*Pseudomonas perfectomarina*). Glucan 1,4-alpha-maltotetrahydrolase precursor (EC 3.2.1.60) (G4-amylase) (Maltotetraose-forming amylase) (Exo-maltotetraohydrolase)(Maltotetraose-forming exo-amylase). SWISS-PROT accession number P13507.

SEQ ID NO: 12 shows a *P. stutzeri* maltotetraose-forming amylase (amyp) gene, complete cds. GenBank accession number M24516.

SEQ ID NO: 13 shows a PSac-pPD77d33 sequence; *Pseudomonas saccharophila* maltotetrahydrolase amino acid sequence with 10 substitutions (N33Y, D34N, G134R, A141P, 1157L, L178F, A179T, G223A, H307L, S334P) and deletion of the starch binding domain.

SEQ ID NO: 14 shows a PSac-D34(Y33N) sequence; *Pseudomonas saccharophila* maltotetrahydrolase amino acid sequence with 10 substitutions and deletion of the starch binding domain.

SEQ ID NO: 15 shows a PSac-D20(Y33N) sequence; *Pseudomonas saccharophila* maltotetrahydrolase amino acid sequence with 12 substitutions and deletion of the starch binding domain.

SEQ ID NO: 16 shows a PSac-D14(Y33N) sequence; *Pseudomonas saccharophila* maltotetrahydrolase amino acid sequence with 13 substitutions and deletion of the starch binding domain.

SEQ ID NO: 17 shows a PStu-D34(Y33N) sequence; *Pseudomonas stutzeri* maltotetrahydrolase amino acid sequence with 8 substitutions.

SEQ ID NO: 18 shows a PStu-D20 (Y33N sequence; *Pseudomonas stutzeri* maltotetrahydrolase acid sequence with 10 substitutions.

SEQ ID NO: 19 shows a PStu-D14(Y33N) sequence; *Pseudomonas stutzeri* maltotetrahydrolase amino acid sequence with 11 substitutions.

SEQ ID NO: 20 shows a PSac-pPD77d33(Y33N) sequence; *Pseudomonas saccharophila* maltotetrahydrolase amino acid sequence with 9 substitutions (D34N, G134R, A141P, 1157L, L178F, A179T, G223A, H307L, S334P) and deletion of the starch binding domain.

SEQ ID NO: 21 shows a PSac-D34(N34D) sequence; *Pseudomonas saccharophila* maltotetrahydrolase amino acid sequence with 10 substitutions and deletion of the starch binding domain.

SEQ ID NO: 22 shows a PSac-D20(N34D) sequence; *Pseudomonas saccharophila* maltotetrahydrolase amino acid sequence with 12 substitutions and deletion of the starch binding domain.

SEQ ID NO: 23 shows a PSac-D14(N34D) sequence; *Pseudomonas saccharophila* maltotetrahydrolase amino acid sequence with 13 substitutions and deletion of the starch binding domain.

SEQ ID NO: 24 shows a PStu-D34(N34D) sequence; *Pseudomonas stutzeri* maltotetrahydrolase amino acid sequence with 8 substitutions.

SEQ ID NO: 25 shows a PStu-D20(N34D) sequence; *Pseudomonas stutzeri* maltotetrahydrolase amino acid sequence with 10 substitutions.

SEQ ID NO: 26 shows a PStu-D14(N34D) sequence; *Pseudomonas stutzeri* maltotetrahydrolase amino acid sequence with 11 substitutions.

SEQ ID NO: 27 shows a PSac-pPD77d33(N34D) sequence; *Pseudomonas saccharophila* maltotetrahydrolase amino acid sequence with 9 substitutions (N33Y, G134R, A141P, 1157L, L178F, A179T, G223A, H307L, S334P) and deletion of the starch binding domain.

SEQ ID NO: 28 shows a PSac-D34(Y33N-N34D) sequence; *Pseudomonas saccharophila* maltotetrahydrolase amino acid sequence with 9 substitutions and deletion of the starch binding domain.

SEQ ID NO: 29 shows a PSac-D20(Y33N-N34D) sequence; *Pseudomonas saccharophila* maltotetrahydrolase amino acid sequence with 11 substitutions and deletion of the starch binding domain.

SEQ ID NO: 30 shows a PSac-D14(Y33N-N34D) sequence; *Pseudomonas saccharophila* maltotetrahydrolase amino acid sequence with 12 substitutions and deletion of the starch binding domain.

SEQ ID NO: 31 shows a PStu-D34(Y33N-N34D) sequence; *Pseudomonas stutzeri* maltotetrahydrolase amino acid sequence with 7 substitutions.

SEQ ID NO: 32 shows a PStu-D20(Y33N-N34D) sequence; *Pseudomonas stutzeri* maltotetrahydrolase amino acid sequence with 9 substitutions.

SEQ ID NO: 33 shows a PStu-D14(Y33N-N34D) sequence; *Pseudomonas stutzeri* maltotetrahydrolase amino acid sequence with 10 substitutions.

SEQ ID NO: 34 shows a PSac-pPD77d33(Y33N-N34D) sequence; *Pseudomonas saccharophila* maltotetrahydrolase amino acid sequence with 8 substitutions (G134R, A141P, 1157L, L178F, A179T, G223A, H307L, S334P) and deletion of the starch binding domain.

Other sequences are also shown in the sequence listings. Each of these other sequences, as well as those SEQ ID NO: 1 to 34 may (with the exception of SEQ ID NO: 1, 5, 6, 7, 11 and 12) may be used as PS4 variant polypeptides according to the methods and compositions described here. Each of these sequences may be employed as parent sequences.

DETAILED DESCRIPTION

In the following description and examples, unless the context dictates otherwise, dosages of PS4 variant polypeptides are given in parts per million (micrograms per gram) of flour. For example, "1 D34" as used in Table 2 indicates 1 part per million of pSac-D34 based on weight per weight. Preferably, enzyme quantities or amounts are determined based on activity of pure enzyme measured with bovine serum albumin (BSA) as a standard, using the assay described in Bradford (1976, A rapid and sensitive method for the quantification of microgram quantities of protein utilizing the principle of protein-dye binding. Anal. Biochem. 72:248-254).

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989*, Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996*, DNA Isolation and Sequencing: Essential Techniques*, John Wiley & Sons; J. M. Polak and James O'D. McGee, 1990*, In Situ Hybridization: Principles and Practice*; Oxford University Press M. J. Gait (Editor), 1984*, Oligonucleotide Synthesis: A Practical Approach*, Irl Press; D. M. J. Lilley and J. E. Dahlberg, 1992*, Methods of Enzymology: DNA Structure Part A: Synthesis and Physical Analysis of DNA* Methods in Enzymology, Academic Press; Using Antibodies: A-Laboratory Manual: Portable Protocol NO. I by Edward Harlow, David Lane, Ed Harlow (1999, Cold Spring Harbor Laboratory Press, ISBN 0-87969-54-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Baca Raton, Fla., 1998 ISBN 0-8493-6078-1, John D. Pound (ed); "*Immunochemical Protocols, vol* 80", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

PS4 Variants

We provide for competitions comprising polypeptides which are variants of polypeptides having non-maltogenic exoamylase activity, as well as uses of such variant polypeptides and the compositions. The compositions include the polypeptide variants together with another component. In particular, we provide for food additives comprising the polypeptides.

Such variant polypeptides are referred to in this document as "PS4 variant polypeptides". Nucleic acids encoding such variant polypeptides will be referred to for convenience as "PS4 variant nucleic acids". PS4 variant polypeptides and nucleic acids will be described in further detail below.

Specifically, the polypeptides disclosed in U.S. applications Ser. Nos. 60/485,413 and 60/485,616 (to be assigned, attorney docket numbers GC806P and GC807P), in which inventor Kragh is a co-inventor, as well as those disclosed in concurrently filed PCT application designating the US (applicant: Genencor GC806-PCT and GC807-PCT), in which inventor Kragh is a co-inventor, are to be included within the term "PS4 variant polypeptides". Such polypeptides are suitable for use in the applications described herein, in particular, as food additives, to treat starch as described, to prepare a food product, to make a bakery product, for the formulation of improver compositions, for the formulation of combinations, etc.

Likewise, the nucleic acids disclosed in these documents should be understood to be included within the term "PS4 variant nucleic acids".

Specifically, we provide for PS4 variant polypeptides with sequence alterations comprising amino acid substitutions in a non-maltogenic exoamylase sequence. The amino acid substitutions may be at positions 134, 141, 157, 223, 307 and 334, with reference to the position numbering of a *Pseudomonas saccharophilia* exoamylase sequence shown as SEQ ID NO: 1. Further substitutions at one or both of positions 33 and 34 may be present. Even further substitutions at positions 178 and 179 may also be included. These are described in detail below.

The residue at position 33 is preferably wild type, i.e., N; similarly, the residue at position 34 is preferably wild type, i.e., D.

Where a substitution at position 121 is present, it will advantageously comprise G121D. Similarly where a substitution at position 223 is present, it will advantageously comprise G223A. Alternatively, it may comprise G223L. Accordingly, in some embodiments, we disclose a food additive comprising a PS4 variant polypeptide, in which the PS4 variant polypeptide is derivable from a parent polypeptide having non-maltogenic exoamylase activity, in which the PS4 variant polypeptide comprises substitutions at the following positions: G121D, 134, 141, 157, G223A, 307 and 334 with reference to the position numbering of a *Pseudomonas saccharophilia* exoamylase sequence shown as SEQ ID NO: 1.

Such variant polypeptides retain the features of the parent polypeptides, and additionally preferably have additional beneficial properties, for example, enhanced activity or thermostability, or pH resistance, or any combination (preferably all).

The PS4 substitution mutants described here may be used for any purpose for which the parent enzyme is suitable. In particular, they may be used in any application for which exo-maltotetraohydrolase is used. In highly preferred embodiments, they have the added advantage of higher thermostability, or higher exoamylase activity or higher pH stability, or any combination. Examples of suitable uses for the PS4 variant polypeptides and nucleic acids include food production, in particular baking, as well as production of foodstuffs; further examples are set out in detail below.

The "parent" sequences, i.e., the sequences on which the PS4 variant polypeptides and nucleic acids are based, preferably are polypeptides having non-maltogenic exoamylase activity. The terms "parent enzymes" and "parent polypeptides" should be interpreted accordingly, and taken to mean the enzymes and polypeptides on which the PS4 variant polypeptides are based.

In particularly preferred embodiments, the parent sequences are non-maltogenic exoamylase enzymes, preferably bacterial non-maltogenic exoamylase enzymes. In highly preferred embodiments, the parent sequence comprises a glucan 1,4-alpha-maltotetrahydrolase (EC 3.2.1.60). Preferably, the parent sequence is from *Pseudomonas* species, for example *Pseudomonas saccharophilia* or *Pseudomonas stutzeri.*

In preferred embodiments, the parent polypeptide comprises, or is homologous to, a *Pseudomonas saccharophilia* non-maltogenic exoamylase having a sequence shown as SEQ ID NO: 1. Proteins and nucleic acids related to, preferably having sequence or functional homology with *Pseudomonas saccharophilia* non-maltogenic exoamylase *Pseudomonas saccharophilia* exoamylase sequence shown as SEQ ID NO: 1 are referred to in this document as members of the "PS4 family". Examples of "PS4 family" non-maltogenic exoamylase enzymes suitable for use in generating the PS4 variant polypeptides and nucleic acids are disclosed in further detail below.

In some preferred embodiments, the parent polypeptide comprises a non-maltogenic exoamylase from *Pseudomonas saccharophilia* non-maltogenic exoamylase having a sequence shown as SEQ ID NO: 1, or a SWISS-PROT accession number P22963. In other preferred embodiments, the parent polypeptide comprises a non-maltogenic exoamylase from *Pseudomonas stutzeri* having a sequence shown as SEQ ID NO: 11, or a *Pseudomonas stutzeri* non-maltogenic exoamylase having SWISS-PROT accession number P13507.

The PS4 variant polypeptides and nucleic acids vary from their parent sequences by including a number of mutations. In other words, the sequence of the PS4 variant polypeptide or nucleic acid is different from that of its parent at a number of positions or residues. In preferred embodiments, the mutations comprise amino acid substitutions, that is, a change of one amino acid residue for another. Thus, the PS4 variant polypeptides comprise a number of changes in the nature of the amino acid residue at one or more positions of the parent sequence.

In describing the different PS4 variant polypeptide variants produced or which are contemplated to be encompassed by this document, the following nomenclature will be adopted for ease of reference: [original amino acid/position according to the numbering system/substituted amino acid]. Accordingly, for example, the substitution of alanine with proline in position 141 is designated as A141P. Multiple mutations may be designated by being separated by slash marks "/", e.g. A141P/G223A representing mutations in position 141 and 223 substituting alanine with proline and glycine with alanine respectively.

All positions referred to in the present document by numbering refer to the numbering of a *Pseudomonas saccharophilia* exoamylase reference sequence shown below (SEQ ID NO: 1):

```
  1 DQAGKSPAGV RYHGGDEIIL QGFHWNVVRE APNDWYNILR QQASTIAADG FSAIWMPVPW
 61 RDFSSWTDGG KSGGGEGYFW HDFNKNGRYG SDAQLRQAAG ALGGAGVKVL YDVVPNHMNR
121 GYPDKEINLP AGQGFWRNDC ADPGNYPNDC DDGDRFIGGE SDLNTGHPQI YGMFRDELAN
181 LRSGYGAGGF RFDFVRGYAP ERVDSWMSDS ADSSFCVGEL WKGPSEYPSW DWRNTASWQQ
241 IIKDWSDRAK CPVFDFALKE RMQNGSVADW KHGLNGNPDP RWREVAVTFV DNHDTGYSPG
301 QNGGQHHWAL QDGLIRQAYA YILTSPGTPV VYWSHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGGE GGLVNVNFRC DNGVTQMGDS VYAVGNVSQL GNWSPASAVR LTDTSSYPTW
481 KGSIALPDGQ NVEWKCLIRN EADATLVRQW QSGGNNQVQA AAGASTSGSF
```

The reference sequence is derived from the *Pseudomonas saccharophilia* sequence having SWISS-PROT accession number P22963, but without the signal sequence MSHILRAAVLAAVLLPFPALA (SEQ ID NO: 41).

The PS4 variant polypeptide variants described here preferably comprises substitutions at the following positions: G134, A141, 1157, G223, H307, S334, N33 and D34. Preferably, they may comprise in addition substitutions at one or both of L178 and A179. In further preferred embodiments, glycine at position 134 is substituted by arginine in the PS4 variant polypeptides. In further particularly preferred embodiments, arginine at position 141 is substituted by proline. Furthermore, in such particularly preferred embodiments, serine at position 334 is substituted by proline.

Accordingly, in preferred embodiments, the PS4 variant polypeptides comprise substitutions arginine at position 134, proline at position 141 and proline at position 334, e.g., G134R, A141P and S334P. The residues at positions 157, 223, 307, 33, 34, 178 and 179, may be substituted by a number of residues, for example 1157V or 1157N or G223L or G2231 or G223S or G223T or H3071 or H307V or D34G or D34A or D34S or D34T or A179V.

However, the PS4 variant polypeptides preferably comprise the substitutions I157L, L178F, A179T G223A and H307L. Where substitutions at positions 33 and/or 34 are present, these will preferably be N33Y and D34N.

In highly preferred embodiments, PS4 variant polypeptides comprise the following substitutions: G134R, A141P, 1157L, G223A, H307L and S334P, together with one or both of L178F and A179T. Optionally, substitutions N33Y and D34N may also be included.

In one embodiment, the PS4 variants are derived from a *Pseudomonas saccharophila* non-maltogenic enzyme sequence. Accordingly, and preferably, the PS4 variant polypeptide variant comprises a sequence PSac-D34 (SEQ ID NO: 2).

One or more further substitutions may be introduced into the parent sequence, in particular, at G121 or G87, or at both positions. The G121 substitution preferably comprises G121D, and the G87 substitution preferably comprises G87S.

Accordingly, we disclose *Pseudomonas saccharophilia* based PS4 variant polypeptides comprising the following substitutions: G134R, A141P, 1157L, G121D; G223A, H307L and S334P, together with one or both of L178F and A179T, optionally also N33Y and/or D34N, as well as PS4 variant polypeptides comprising the following substitutions: G87S, G121D, G134R, A141P, 1157L, G223A, H307L and S334P, together with one or both of L178F and A179T, optionally together with N33Y and/or D34N.

Therefore, a PS4 variant based on *Pseudomonas saccharophila* non-maltogenic enzyme sequence may have a sequence PSac-D20 (SEQ ID NO: 3), comprising G121D, or a sequence PSac-D14 (SEQ ID NO: 4), further comprising G87S. The PS4 variant polypeptide may have the sequence PSac-pPD77d33.

In another embodiment, the PS4 variants are derived from a *Pseudomonas stutzeri* non-maltogenic enzyme sequence, preferably shown as SEQ ID NO: 7 below:

```
  1 DQAGKSPNAV RYHGGDEIIL QGFHWNVVRE APNDWYNILR QQAATIAADG FSAIWMPVPW
 61 RDFSSWSDGS KSGGGEGYFW HDFNKNGRYG SDAQLRQAAS ALGGAGVKVL YDVVPNHMNR
121 GYPDKEINLP AGQGFWRNDC ADPGNYPNDC DDGDRFIGGD ADLNTGHPQV YGMFRDEFTN
181 LRSQYGAGGF RFDFVRGYAP ERVNSWMTDS ADNSFCVGEL WKGPSEYPNW DWRNTASWQQ
241 IIKDWSDRAK CPVFDFALKE RMQNGSIADW KHGLNGNPDP RWREVAVTFV DNHDTGYSPG
301 QNGGQHHWAL QDGLIRQAYA YILTSPGTPV VYWSHMYDWG YGDFIRQLIQ VRRAAGVRAD
361 SAISFHSGYS GLVATVSGSQ QTLVVALNSD LGNPGQVASG SFSEAVNASN GQVRVWRSGT
421 GSGGGEPGAL VSVSFRCDNG ATQMGDSVYA VGNVSQLGNW SPAAALRLTD TSGYPTWKGS
481 IALPAGQNEE WKCLIRNEAN ATQVRQWQGG ANNSLTPSEG ATTVGRL
```

Accordingly, the PS4 variant polypeptide may comprise a sequence PStu-D34 (SEQ ID NO: 8). We further disclose PS4 variant polypeptides based on *Pseudomonas stutzeri* non-maltogenic enzyme-sequence and including G121 and/or G87 substitutions. These may comprise the following substitutions: N33Y (if a substitution at position 33 is present), D34N (if a substitution at position 34 is present), G121D, G134R, A141P, 1157L, G223A, H307L and S334P, together with one or both of L178F and A179T, as well as PS4 variant polypeptides comprising the following substitutions: N33Y (if a substitution at position 33 is present), D34N (if a substitution at position 34 is present), G87S, G121D, G134R, A141P, 1157L, G223A, H307L and S334P, together with one or both of L178F and A179T.

A PS4 variant based on *Pseudomonas stutzeri* non-maltogenic enzyme sequence may have a sequence PStu-D20 (SEQ ID NO: 9), comprising G121D, or a sequence PStu-D14 (SEQ ID NO: 10), further comprising G87S.

The numbering system, even though it may use a specific sequence as a base reference point, is also applicable to all relevant homologous sequences. For example, the position numbering may be applied to homologous sequences from other *Pseudomonas* species, or homologous sequences from other bacteria. Preferably, such homologous have 60% or greater homology, for example 70% or more, 80% or more, 90% or more or 95% or more homology, with the reference sequence SEQ ID NO: 1 above, or the sequences having SWISS-PROT accession numbers P22963 or P13507, preferably with all these sequences. Sequence homology between proteins may be ascertained using well known alignment programs and hybridisation techniques described herein. Such homologous sequences will be referred to in this document as the "PS4 Family".

Furthermore, and as noted above, the numbering system used in this document makes reference to a reference sequence SEQ ID NO: 1, which is derived from the *Pseudomonas saccharophilia* sequence having SWISS-PROT accession number P22963, but without the signal sequence MSHILRAAVLAAVLLPFPALA (SEQ ID NO: 41). This signal sequence is located N terminal of the reference sequence and consists of 21 amino acid residues. Accordingly, it will be trivial to identify the particular residues to be mutated or substituted in corresponding sequences comprising the signal sequence, or indeed, corresponding sequences comprising any other N- or C- terminal extensions or deletions. For example, the sequence of *Pseudomonas saccharophilia* non-maltogenic exoamylase having SWISS-PROT accession number P22963 or a *Pseudomonas stutzeri* non-maltogenic exoamylase having SWISS-PROT accession number P13507.

The PS4 variant polypeptides may comprise one or more further mutations in addition to those set out above. There may be one, two, three, four, five, six, seven or more mutations preferably substitutions in addition to those already set out. Other mutations, such as deletions, insertions, substitutions, transversions, transitions and inversions, at one or more other locations, may also be included. In addition, the PS4 variants need not have all the substitutions at the positions listed. Indeed, they may have one, two, three, four, or five substitutions missing, i.e., the wild type amino acid residue is present at such positions.

We also describe PS4 nucleic acids having sequences which correspond to or encode the alterations in the PS4 variant polypeptide sequences, for use in producing such polypeptides for the purposes described here. The skilled person will be aware of the relationship between nucleic acid sequence and polypeptide sequence, in particular, the genetic code and the degeneracy of this code, and will be able to construct such PS4 nucleic acids without difficulty. For example, he will be aware that for each amino acid substitution in the PS4 variant polypeptide sequence, there may be one or more codons which encode the substitute amino acid. Accordingly, it will be evident that, depending on the degeneracy of the genetic code with respect to that particular amino acid residue, one or more PS4 nucleic acid sequences may be generated corresponding to that PS4 variant polypeptide sequence. Furthermore, where the PS4 variant polypeptide comprises more than one substitution, for example A141P/G223A, the corresponding PS4 nucleic acids may comprise pairwise combinations of the codons which encode respectively the two amino acid changes.

Thus, for example, a PS4 nucleic acid sequence may be derivable from a parent sequence encoding a polypeptide having non-maltogenic exoamylase activity and comprising codons encoding amino acid substitutions at the following positions: G134, A141, I157, G223, H307, 5334, optionally with one or both of N33 and D34, together with one or both of L178 and A179, with reference to the position numbering of a *Pseudomonas saccharophilia* exoamylase sequence shown as SEQ ID NO: 1. We also describe a nucleic acid sequence derivable from a parent sequence, the parent sequence capable of encoding a non-maltogenic exoamylase, which nucleic acid sequence comprises a substitution at one or more residues such that the nucleic acid encodes one or more of the following mutations at the positions specified: G134, A141, I157, G223, H307, S334, optionally together with one or both of N33 and D34, together with one or both of L178 and A179, with reference to the position numbering of a *Pseudomonas saccharophilia* exoamylase sequence shown as SEQ ID NO: 1.

It will be understood that nucleic acid sequences which are not identical to the particular PS4 variant nucleic acid sequences, but are related to these, will also be useful for the methods and compositions described here, such as a variant, homologue, derivative or fragment of a PS4 variant nucleic acid sequence, or a complement or a sequence capable of hybridising thereof. Unless the context dictates otherwise, the term "PS4 variant nucleic acid" should be taken to include each of these entities listed above.

Mutations in amino acid sequence and nucleic acid sequence may be made by any of a number of techniques, as known in the art. In particularly preferred embodiments, the mutations are introduced into parent sequences by means of PCR (polymerase chain reaction) using appropriate primers, as illustrated in the Examples. It is therefore possible to alter the sequence of a polypeptide by introducing amino acid substitutions comprising: G134, A141, I157, G223, H307, S334, optionally N33 and/or D34, together with one or both of L178 and A179, into a parent polypeptide having non-maltogenic exoamylase activity, such as into a *Pseudomonas saccharophilia* or a *Pseudomonas stutzeri* exoamylase sequence at amino acid or nucleic acid level, as described. We describe a method in which the sequence of a non-maltogenic exoamylase is altered by altering the sequence of a nucleic acid which encodes the non-maltogenic exoamylase.

The PS4 variant polypeptides and nucleic acids may be produced by any means known in the art. Specifically, they may be expressed from expression systems, which may be in vitro or in vivo in nature. Specifically, we describe plasmids and expression vectors comprising PS4 nucleic acid sequences, preferably capable of expressing PS4 variant polypeptides. Cells and host cells which comprise and are preferably transformed with such PS4 nucleic acids, plasmids and vectors are also disclosed, and it should be made clear that these are also encompassed in this document.

In preferred embodiments, the PS4 variant polypeptide sequence is used as a food additive in an isolated form. The term "isolated" means that the sequence is at least substantially free from at least one other component with which the sequence is naturally associated in nature and as found in nature. In one aspect, preferably the sequence is in a purified form. The term "purified" means that the sequence is in a relatively pure state—e.g. at least about 90% pure, or at least about 95% pure or at least about 98% pure.

Parent Enzyme

The PS4 variant polypeptides are derived from, or are variants of, another sequence, known as a "parent enzyme", a "parent polypeptide" or a "parent sequence".

The term "parent enzyme" as used in this document means the enzyme that has a close, preferably the closest, chemical structure to the resultant variant, i.e., the PS4 variant polypeptide or nucleic acid. The parent enzyme may be a precursor enzyme (i.e. the enzyme that is actually mutated) or it may be prepared de novo. The parent enzyme may be a wild type enzyme.

The term "precursor" as used herein means an enzyme that precedes the enzyme which is modified to produce the enzyme. Thus, the precursor may be an enzyme that is modified by mutagenesis. Likewise, the precursor may be a wild type enzyme, a variant wild type enzyme or an already mutated enzyme.

The term "wild type" is a term of the art understood by skilled persons and means a phenotype that is characteristic of most of the members of a species occurring naturally an 4 contrasting with the phenotype of a mutant. Thus, in the present context, the wild type enzyme is a form of the enzyme naturally found in most members of the relevant species. Generally, the relevant wild type enzyme in relation to the variant polypeptides described here is the most closely related corresponding wild type enzyme in terms of sequence homology. However, where a particular wild type sequence has been used as the basis for producing a variant PS4 polypeptide as described here, this will be the corresponding wild type sequence regardless of the existence of another wild type sequence that is more closely related in terms of amino acid sequence homology.

The parent enzyme is preferably a polypeptide which preferably exhibits non-maltogenic exoamylase activity. Preferably, the parent enzyme is a non-maltogenic exoamylase itself. For example, the parent enzyme may be a *Pseudomonas saccharophila* non-maltogenic exoamylase, such as a polypeptide having SWISS-PROT accession number P22963, or a *Pseudomonas stutzeri* non-maltogenic exoamylase, such as a polypeptide having SWISS-PROT accession number P13507. Other members of the PS4 family may be used as parent enzymes; such PS4 family members will generally be similar to, homologous to, or functionally equivalent to either of these two enzymes, and may be identified by standard methods, such as hybridisation screening of a suitable library using probes, or by genome sequence analysis.

In particular, functional equivalents of either of these two enzymes, as well as other members of the "PS4 family" may also be used as starting points or parent polypeptides for the generation of PS4 variant polypeptides as described here.

A "functional equivalent" of a protein means something that shares one or more, preferably substantially all, of the functions of that protein. Preferably, such functions are biological functions, preferably enzymatic functions, such as amylase activity, preferably non-maltogenic exoamylase activity.

The term "functional equivalent" in relation to a parent enzyme being a *Pseudomonas saccharophila* non-maltogenic exoamylase, such as a polypeptide having SWISS-PROT accession number P22963, or a *Pseudomonas stutzeri* non-maltogenic exoamylase, such as a polypeptide having SWISS-PROT accession number P13507 means that the functional equivalent could be obtained from other sources. The functionally equivalent enzyme may have a different amino acid sequence but will have non-maltogenic exoamylase activity.

In highly preferred embodiments, the functional equivalent will have sequence homology to either of the *Pseudomonas saccharophilia* and *Pseudomonas stutzeri* non-maltogenic exoamylase mentioned above, preferably both. The functional equivalent may also have sequence homology with any of the sequences set out as SEQ ID NOs: 1 to 12, preferably SEQ ID NO: 1 or SEQ ID NO: 7 or both. Sequence homology between such sequences is preferably at least 60%, preferably 65% or more, preferably 75% or more, preferably 80% or more, preferably 85% or more, preferably 90% or more, preferably 95% or more. Such sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 *ibid*—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 *ibid*, pages 7-58 to 7-60). However it is preferred to use the GCG Bestfit program.

In other embodiments, the functional equivalents will be capable of specifically hybridising to any of the sequences set out above. Methods of determining whether one sequence is capable of hybridising to another are known in the art, and are for example described in Sambrook, et al (supra) and Ausubel, F. M. et al. (supra). In highly preferred embodiments, the functional equivalents will be capable of hybridising under stringent conditions, e.g. 65° C. and 0.1×SSC {1×SSC=0.15 M NaCl, 0.015 M $Na_3$ Citrate pH 7.0}.

For example, functional equivalents which have sequence homology to *Pseudomonas saccharophila* and *Pseudomonas stutzeri* non-maltogenic exoamylases are suitable for use as parent enzymes. Such sequences may differ from the *Pseudomonas saccharophila* sequence at any one or more positions. Furthermore, non-maltogenic exoamylases from other strains of *Pseudomonas* spp, such as ATCC17686, may also be used as a parent polypeptide. The PS4 variant polypeptide residues may be inserted into any of these parent sequences to generate the variant PS4 polypeptide sequences.

The parent enzymes may be modified at the amino acid level or the nucleic acid level to generate the PS4 variant sequences described here. Therefore, we provide for the generation of PS4 variant polypeptides by introducing one or more corresponding codon changes in the nucleotide sequence encoding a non-maltogenic exoamylase polypeptide.

The nucleic acid numbering should preferably be with reference to the position numbering of a *Pseudomonas saccharophilia* exoamylase nucleotide sequence shown as SEQ ID NO: 6. Alternatively, or in addition, reference may be made to the sequence with GenBank accession number X16732. In preferred embodiments, the nucleic acid numbering should be with reference to the nucleotide sequence shown as SEQ ID NO; 6. However, as with amino acid residue numbering, the residue numbering of this sequence is to be used only for reference purposes only. In particular, it will be appreciated that the above codon changes can be made in any PS4 family nucleic acid sequence. For example, sequence changes can be made to a *Pseudomonas saccharophila* or a

*Pseudomonas stutzeri* non-maltogenic exoamylase nucleic acid sequence (e.g., X16732, SEQ ID NO: 6 or M24516, SEQ ID NO: 12).

The parent enzyme may comprise the "complete" enzyme, i.e., in its entire length as it occurs in nature (or as mutated), or it may comprise a truncated form thereof. The PS4 variant derived from such may accordingly be so truncated, or be "full-length". The truncation may be at the N-terminal end, or the C-terminal end, preferably the C-terminal end. The parent enzyme or PS4 variant may lack one or more portions, such as sub-sequences, signal sequences, domains or moieties, whether active or not etc. For example, the parent enzyme or the PS4 variant polypeptide may lack a signal sequence, as described above. Alternatively, or in addition, the parent enzyme or the PS4 variant may lack one or more catalytic or binding domains.

In highly preferred embodiments, the parent enzyme or PS4 variant may lack one or more of the domains present in non-maltogenic exoamylases, such as the starch binding domain. For example, the PS4 polypeptides may have only sequence up to position 429, relative to the numbering of a *Pseudomonas saccharophilia* non-maltogenic exoamylase shown as SEQ ID NO: 1. It is to be noted that this is the case for the PS4 variants pSac-d34, pSac-D20 and pSac-D14.

Amylase

The PS4 variant polypeptides generally comprise amylase activity.

The term "amylase" is used in its normal sense—e.g. an enzyme that is inter alia capable of catalysing the degradation of starch. In particular they are hydrolases which are capable of cleaving α-D-(1→4) O-glycosidic linkages in starch.

Amylases are starch-degrading enzymes, classified as hydrolases, which cleave αD-(1→4) O-glycosidic linkages in starch. Generally, α-amylases (E.C. 3.2.1.1, α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (E.C. 3.2.1.2, α-D-(1→4)-glucan maltohydrolase), and some product-specific amylases like maltogenic alpha-amylase (E.C. 3.2.1.133) cleave the starch molecule from the non-reducing end of the substrate. β-Amylases, α-glucosidases (E.C. 3.2.1.20, α-D-glucoside glucohydrolase), glucoamylase (E.C. 3.2.1.3, α-D-(1→4)-glucan glucohydrolase), and product-specific amylases can produce malto-oligosaccharides of a specific length from starch.

Non-Maltogenic Exoamylase

The PS4 variant polypeptides described in this document are derived from (or variants of) polypeptides which preferably exhibit non-maltogenic exoamylase activity. Preferably, these parent enzymes are non-maltogenic exoamylases themselves. The PS4 variant polypeptides themselves in highly preferred embodiments also exhibit non-maltogenic exoamylase activity.

In highly preferred embodiments, the term "non-maltogenic exoamylase enzyme" as used in this document should be taken to mean that the enzyme does not initially degrade starch to substantial amounts of maltose as analysed in accordance with the product determination procedure as described in this document.

In highly preferred embodiments, the non-maltogenic exoamylase comprises an exo-maltotetraohydrolase. Exo-maltotetraohydrolase (E.C.3.2.1.60) is more formally known as glucan 1,4-alpha-maltotetrahydrolase. This enzyme hydrolyses 1,4-alpha-D-glucosidic linkages in amylaceous polysaccharides so as to remove successive maltotetraose residues from the non-reducing chain ends.

Non-maltogenic are de rib in detail in U.S. Pat. No. 6,667,065, hereby incorporated by reference.

Assays for Non-Maltogenic Exoamylase Activity

The following system is used to characterize polypeptides having non-maltogenic exoamylase activity which are suitable for use according to the methods and compositions described here. This system may for example be used to characterise the PS4 parent or variant polypeptides described here.

By way of initial background information, waxy maize amylopectin (obtainable as WAXILYS 200 from Roquette, France) is a starch with a very high amylopectin content (above 90%). 20 mg/ml of waxy maize starch is boiled for 3 min. in a buffer of 50 mM MES (2-(N-morpholino)ethanesulfonic acid), 2 mM calcium chloride, pH 6.0 and subsequently incubated at 50° C. and used within half an hour.

One unit of the non-maltogenic exoamylase is defined as the amount of enzyme which releases hydrolysis products equivalent to 1 μmol of reducing sugar per min. when incubated at 50 degrees C. in a test tube with 4 ml of 10 mg/ml waxy maize starch in 50 mM MES, 2 mM calcium chloride, pH 6.0 prepared as described above. Reducing sugars are measured using maltose as standard and using the dinitrosalicylic acid method of Bernfeld, *Methods Enzymol*., (1954), 1, 149-158 or another method known in the art for quantifying reducing sugars.

The hydrolysis product pattern of the non-maltogenic exoamylase is determined by incubating 0.7 units of non-maltogenic exoamylase for 15 or 300 min. at 50° C. in a test tube with 4 ml of 10 mg/ml waxy maize starch in the buffer prepared as described above. The reaction is stopped by immersing the test tube for 3 min. in a boiling water bath.

The hydrolysis products are analyzed and quantified by anion exchange HPLC using a Dionex PA 100 column with sodium acetate, sodium hydroxide and water as eluents, with pulsed amperometric detection and with known linear maltooligosaccharides of from glucose to maltoheptaose as standards. The response factor used for maltooctaose to maltodecaose is the response factor found for maltoheptaose.

Preferably, the PS4 variant polypeptides have non-maltogenic exoamylase activity such that if an amount of 0.7 units of said non-maltogenic exoamylase were to incubated for 15 minutes at a temperature of 50° C. at pH 6.0 in 4 ml of an aqueous solution of 10 mg preboiled waxy maize starch per ml buffered solution containing 50 mM 2-(N-1-morpholino) ethane sulfonic acid and 2 mM calcium chloride then the enzyme would yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis products would consist of linear maltooligosaccharides of from three to ten D-glucopyranosyl units, preferably of linear maltooligosaccharides consisting of from four to eight D-glucopyranosyl units.

For ease of reference, and for the present purposes, the feature of incubating an amount of 0.7 units of the non-maltogenic exoamylase for 15 minutes at a temperature of 50° C. at pH 6.0 in 4 ml of an aqueous solution of 10 mg preboiled waxy maize starch per ml buffered solution containing 50 mM 2-(N-morpholino)ethane sulfonic acid and 2 mM calcium chloride, may be referred to as the "Waxy Maize Starch Incubation Test".

Thus, alternatively expressed, preferred PS4 variant polypeptides which are non-maltogenic exoamylases are characterised as having the ability in the waxy maize starch incubation test to yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

The hydrolysis products in the waxy maize starch incubation test may include one or more linear malto-oligosaccharides of from two to ten D-glucopyranosyl units and optionally glucose. The hydrolysis products in the waxy maize starch incubation test may also include other hydrolytic products. Nevertheless, the % weight amounts of linear maltooligosaccharides of from three to ten D-glucopyranosyl units are based on the amount of the hydrolysis duct that consists of bone or more linear malto-oligosaccharides of from two to ten D-glucopyranosyl units and optionally glucose. In other words, the % weight amounts of linear maltooligosaccharides of from three to ten D-glucopyranosyl units are not based on the amount of hydrolysis products other than one or more linear malto-oligosaccharides of from two to ten D-glucopyranosyl units and glucose.

The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

For ease of reference, and for the present purposes, the feature of analysing the hydrolysis product(s) using anion exchange HPLC using a Dionex PA 100 column with pulsed amperometric detection and with known linear maltooligosaccharides of from glucose to maltoheptaose used as standards, can be referred to as "analysing by anion exchange". Of course, and as just indicated, other analytical techniques would suffice, as well as other specific anion exchange techniques.

Thus, alternatively expressed, a preferred PS4 variant polypeptide is one which has non-maltogenic exoamylase such that it has the ability in a waxy maize starch incubation test to yield hydrolysis product(s) that would consist of one or more linear malto-oligosaccharides of from two to ten D-glucopyranosyl units and optionally glucose, said hydrolysis products being capable of being analysed by anion exchange; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

As used herein, the term "linear malto-oligosaccharide" is used in the normal sense as meaning 2-10 units of α-D-glucopyranose linked by an α-(1→4) bond.

In highly preferred embodiments, the PS4 polypeptides described here have improved exoamylase activity, preferably non-maltogenic exoamylase activity, when compared to the parent polypeptide, preferably when tested under the same conditions. In particular, in highly preferred embodiments, the PS4 variant polypeptides have 10% or more, preferably 20% or more, preferably 50% or more, exoamylase activity compared to their parents, preferably when measured in a waxy maize starch test.

The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

As used herein, the term "linear malto-oligosaccharide" is used in the normal sense as meaning 2-20 units of α-D-glucopyranose linked by an α-(1→4) bond.

Improved Properties

The PS4 variants described here preferably have improved properties when compared to their parent enzymes, such as any one or more of improved thermostability, improved pH stability, or improved exo-specificity.

Without wishing to be bound by any particular theory, we believe that the mutations at the particular positions have individual and cumulative effects on the properties of a polypeptide comprising such mutations. Thus, for example, we believe that positions 134, 141, 157, 223, 334, as well as optionally positions 178 or 179, or both influence the thermostability of PS4 polypeptides comprising such changes. Particularly, and preferably, positive or beneficial effects reside in these positions, particular in the substitutions: 134R, 141P, 157L, 223A, 307L, 334P, 178F and 179T where present.

On the other hand, we believe that positions 307, as well as position 121 have effects (preferably positive effects) on the exo-specificity of a PS4 polypeptide.

Thermostability and pH Stability

Preferably, the PS4 variant polypeptide is thermostable; preferably, it has higher thermostability than its parent enzyme.

In wheat and other cereals the external side chains in amylopectin are in the range of DP 12-19. Thus, enzymatic hydrolysis of the amylopectin side chains, for example, by PS4 variant polypeptides as described having non-maltogenic exoamylase activity, can markedly reduce their crystallisation tendencies.

Starch in wheat and other cereals used for baking purposes is present in the form of starch granules which generally are resistant to enzymatic attack by amylases. Thus starch modification is mainly limited to damaged starch and is progressing very slowly during dough processing and initial baking until gelatinisation starts at about 60 C. As a consequence hereof only amylases with a high degree of thermostability are able to modify starch efficiently during baking. And generally the efficiency of amylases is increased with increasing thermostability. That is because the more thermostable the enzyme is the longer time it can be active during baking and thus the more antistaling effect it will provide.

Accordingly, the use of PS4 variant polypeptides as described here when added to the starch at any stage of its processing into a food product, e.g., before during or after baking into bread can retard or impede or slow down the retrogradation. Such use is described in further detail below.

As used herein the term 'thermostable' relates to the ability of the enzyme to retain activity after exposure to elevated temperatures. Preferably, the PS4 variant polypeptide is capable of degrading starch at temperatures of from about 55° C. to about 80° C. or more. Suitably, the enzyme retains its activity after exposure to temperatures of up to about 95° C.

The thermostability of an enzyme such as a non-maltogenic exoamylase is measured by its half life. Thus, the PS4 variant polypeptides described here have half lives extended relative to the parent enzyme by preferably 10%, 20%, 30%, 40%, 50%, 60%, 70%, 80%, 90%, 100%, 200% or more, preferably at elevated temperatures of from 55° C. to about 95° C. or more, preferably at about 80° C.

As used here, the half life (t½) is the time (in minutes) during which half the enzyme activity is inactivated under defined heat conditions. In preferred embodiments, the half life is assayed at 80 degrees C. Preferably, the sample is heated for 1-10 minutes at 80° C. or higher. The half life value is then calculated by measuring the residual amylase activity, by any of the methods described here. Preferably, a half life assay is conducted as described in more detail in the Examples.

Preferably, the PS4 variants described here are active during baking and hydrolyse starch during and after the gelatinization of the granules which starts at temperatures of about 55° C. The more thermostable the non-maltogenic exoamylase is the longer time it can be active and thus the more antistaling effect it will provide. However, during baking above temperatures of about 85° C., enzyme inactivation can take place. If this happens, the non-maltogenic exoamylase may be gradually inactivated so that there is substantially no activity after the baking process in the final bread. Therefore preferentially the non-maltogenic exoamylases suitable for use as described have an optimum temperature above 50° C. and below 98° C.

The thermostability of the PS4 variants described here can be improved by using protein engineering to become more thermostable and thus better suited for the uses described here; we therefore encompass the use of PS4 variants modified to become more thermostable by protein engineering.

Preferably, the PS4 variant polypeptide is pH stable; more preferably, it has a higher pH stability than its cognate parent polypeptide. As used herein the term 'pH stable' relates to the ability of the enzyme to retain activity over a wide range of pHs. Preferably, the PS4 variant polypeptide is capable of degrading starch at a pH of from about 5 to about 10.5. In one embodiment, the degree of pH stability may be assayed by measuring the half life of the enzyme in specific pH conditions. In another embodiment, the degree of pH stability may be assayed by measuring the activity or specific activity of the enzyme in specific pH conditions. The specific pH conditions may be any pH from pH5 to pH10.5.

Thus, the PS4 variant polypeptide may have a longer half life, or a higher activity (depending on the assay) when compared to the parent polypeptide under identical conditions. The PS4 variant polypeptides may have 10%, 20%, 30%, 40%, 50%, 60%, 70%, 80%, 90%, 100%, 200% or longer half life when compared to their parent polypeptides under identical pH conditions. Alternatively, or in addition, they may have such higher activity when compared to the parent polypeptide under identical pH conditions.

Exo-Specificity

It is known that some non-maltogenic exoamylases can have some degree of endoamylase activity. In some cases, this type of activity may need to be reduced or eliminated since endoamylase activity can possibly negatively effect the quality of the final bread product by producing a sticky or gummy crumb due to the accumulation of branched dextrins.

Exo-specificity can usefully be measured by determining the ratio of total amylase activity to the total endoamylase activity. This ratio is referred to in this document as a "Exo-specificity index". In preferred embodiments, an enzyme is considered an exoamylase if it has a exo-specificity index of 20 or more, i.e., its total amylase activity (including exo-amylase activity) is 20 times or more greater than its endoamylase activity. In highly preferred embodiments, the exo-specificity index of exoamylases is 30 or more, 40 or more, 50 or more, 60 or more, 70 or more, 80 or more, 90 or more, or 100 or more, In highly preferred embodiments, the exo-specificity index is 150 or more, 200 or more, 300 or more, or 400 or more.

The total amylase activity and the endoamylase activity may be measured by any means known in the art. For example, the total amylase activity may be measured by assaying the total number of reducing ends released from a starch substrate. Alternatively, the use of a Betamyl assay is described in further detail in the Examples, and for convenience, amylase activity as assayed in the Examples is described in terms of "Betamyl Units" in the Tables and Figures.

Endoamylase activity may be assayed by use of a Phadebas Kit (Pharmacia and Upjohn). This makes use of a blue labelled crosslinked starch (labelled with an azo dye); only internal cuts in the starch molecule release label, while external cuts do not do so. Release of dye may be measured by spectrophotometry. Accordingly, the Phadebas Kit measures endoamylase activity, and for convenience, the results of such an assay (described in the Examples) are referred to in this document as "Phadebas units".

In a highly preferred embodiment, therefore, the exo-specificity index is expressed in terms of Betamyl Units/Phadebas Units.

Exo-specificity may also be assayed according to the methods described in the prior art, for example, in our International Patent Publication Number WO99/50399. This measures exo-specificity by way of a ratio between the endoamylase activity to the exoamylase activity. Thus, in a preferred aspect, the PS4 variants described here will have less than 0.5 endoamylase units (EAU) per unit of exoamylase activity. Preferably the non-maltogenic exoamylases which are suitable for use according to the present invention have less than 0.05 EAU per unit of exoamylase activity and more preferably less than 0.01 EAU per unit of exoamylase activity.

The PS4 variants described here will preferably have exospecificity, for example measured by exo-specificity indices, as described above, consistent with their being exoamylases. Moreover, they preferably have higher or increased exospecificity when compared to the parent enzymes or polypeptides from which they are derived. Thus, for example, the PS4 variant polypeptides may have 10%, 20%, 30%, 40%, 50%, 60%, 70%, 80%, 90%, 100%, 200% or higher exo-specificity index when compared to their parent polypeptides, preferably under identical conditions. They may have 1.5× or higher, 2× or higher, 5× or higher, 10× or higher, 50× or higher, 100× or higher, when compared to their parent polypeptides, preferably under identical conditions.

Uses of PS4 Variant Polypeptides and Nucleic Acids

The PS4 variant polypeptides, nucleic acids, host cells, expression vectors, etc, may be used in any application for which an amylase may be used. In particular, they may be used to substitute for any non-maltogenic exoamylase. They may be used to supplement amylase or non-maltogenic exoamylase activity, whether alone or in combination with other known amylases or non-maltogenic exoamylases.

The PS4 variant sequences described here may be used in various applications in the food industry—such as in bakery and drink products, they may also be used in other applications such as a pharmaceutical composition, or even in the chemical industry. In particular, the PS4 variant polypeptides and nucleic acids are useful for various industrial applications including baking (as disclosed in WO 99/50399) and flour standardisation (volume enhancement or improvement), They may be used to produce maltotetraose from starch and other substrates.

The PS4 variant polypeptides may be used to enhance the volume of bakery products such as bread. While not wishing to be bound by any particular theory, we believe that this results from the reduction in viscosity of the dough during heating (such as baking) as a result of the exoamylase shortening amylose molecules. This enables the carbon dioxide generated by fermentation to increase the size of the bread with less hindrance.

Thus, food products comprising or treated with PS4 variant polypeptides are expanded in volume when compared to products which have not been so treated, or treated with parent polypeptides. In other words, the food products have a larger volume of air per volume of food product. Alternatively, or in addition, the food products treated with PS4 variant polypeptides have a lower density, or weight (or mass) per volume ratio. In particularly preferred embodiments, the PS4 variant polypeptides are used to enhance the volume of bread. Volume enhancement or expansion is beneficial because it reduces the gumminess or starchiness of foods. Light foods are preferred by consumers, and the customer experience is enhanced. In preferred embodiments, the use of PS4 variant polypeptides enhances the volume by 10%, 20%, 30% 40%, 50% or more.

The use of PS4 variant polypeptides to increase the volume of foods is described in detail in the Examples.

Food Uses

The PS4 variant polypeptides and nucleic acids described here may be used as—or in the preparation of—a food. In particular, they may be added to a food, i.e., as a food additive. The term "food" is intended to include both prepared food, as well as an ingredient for a food, such as a flour. In a preferred aspect, the food is for human consumption. The food may be in the from of a solution or as a solid—depending on the use and/or the mode of application and/or the mode of administration.

The PS4 variant polypeptides and nucleic acids may be used as a food ingredient. As used herein the term "food ingredient" includes a formulation; which is or can be added to functional foods or foodstuffs and includes formulations which can be used at low levels in a wide variety of products that require, for example, acidifying or emulsifying. The food ingredient may be in the from of a solution or as a solid—depending on the use and/or the mode of application and/or the mode of administration.

The PS4 variant polypeptides and nucleic acids disclosed here may be—or may be added to—food supplements. The PS4 variant polypeptides and nucleic acids disclosed here may be—or may be added to—functional foods. As used herein, the term "functional food" means food which is capable of providing not only a nutritional effect and/or a taste satisfaction, but is also capable of delivering a further beneficial effect to consumer. Although there is no legal definition of a functional food, most of the parties with an interest in this area agree that they are foods marketed as having specific health effects.

The PS4 variant polypeptides may also be used in the manufacture of a food product or a foodstuff. Typical foodstuffs include dairy products, meat products, poultry products, fish products and dough products. The dough product may be any processed dough product, including fried, deep fried, roasted, baked, steamed and boiled doughs, such as steamed bread and rice cakes. In highly preferred embodiments, the food product is a bakery product.

Preferably, the foodstuff is a bakery product. Typical bakery (baked) products include bread—such as loaves, rolls, buns, pizza bases etc. pastry, pretzels, tortillas, cakes, cookies, biscuits, krackers etc.

Retrogradation/Staling

We describe the use of PS4 variant proteins that are capable of retarding the staling of starch media, such as starch gels. The PS4 variant polypeptides are especially capable of retarding the detrimental retrogradation of starch.

Most starch granules are composed of a mixture of two polymers: an essentially linear amylose and a highly branched amylopectin. Amylopectin is a very large, branched molecule consisting of chains of α-D-glucopyranosyl units joined by (1→4) linkages, wherein said chains are attached by α-D-(1-6) linkages to form branches. Amylopectin is present in all natural starches, constituting about 75% of most common starches. Amylose is essentially a linear chain of (1-4) linked α-D-glucopyranosyl units having few α-D-(1-6) branches. Most starches contain about 25% amylose.

Starch granules heated in the presence of water undergo an order-disorder phase transition called gelatinization, where liquid is taken up by the swelling granules. Gelatinization temperatures vary for different starches. Upon cooling of freshly baked bread the amylose fraction, within hours, retrogrades to develop a network. This process is beneficial in that it creates a desirable crumb structure with a low degree of firmness and improved slicing properties. More gradually crystallisation of amylopectin takes place within the gelatinised starch granules during the days after baking. In this process amylopectin is believed to reinforce the amylose network in which the starch granules are embedded. This reinforcement leads to increased firmness of the bread crumb. This reinforcement is one of the main causes of bread staling.

It is known that the quality of baked products gradually deteriorates during storage As a consequence of starch recystallisation (also called retrogradation), the water-holding capacity of the crumb is changed with important implications on the organoleptic and dietary properties. The crumb loses softness and elasticity and becomes firm and crumbly. The increase in crumb firmness is often used as a measure of the staling process of bread.

The rate of detrimental retrogradation of amylopectin depends on the length of the side chains of amylopectin. Thus, enzymatic hydrolysis of the amylopectin side chains, for example, by PS4 variant polypeptides having non-maltogenic exoamylase activity, can markedly reduce their crystallisation tendencies.

Accordingly, the use of PS4 variant polypeptides as described here when added to the starch at any stage of its processing into a food product, e.g., before during or after baking into bread can retard or impede or slow down the retrogradation. Such use is described in further detail below.

Assays for Measurement of Retrogradation (Inc. Staling)

For evaluation of the antistaling effect of the PS4 variant polypeptides having non-maltogenic exoamylase activity described here, the crumb firmness can be measured 1, 3 and 7 days after baking by means of an Instron 4301 Universal Food Texture Analyzer or similar equipment known in the art.

Another method used traditionally in the art and which is used to evaluate the effect on starch retrogradation of a PS4 variant polypeptide having non-maltogenic exoamylase activity is based on DSC (differential scanning calorimetry). Here, the melting enthalpy of retrograded amylopectin in bread crumb or crumb from a model system dough baked with or without enzymes (control) is measured. The DSC equipment applied in the described examples is a Mettler-Toledo DSC 820 run with a temperature gradient of 10° C. per min. from 20 to 95° C. For preparation of the samples 10-20 mg of crumb are weighed and transferred into Mettler-Toledo aluminium pans which then are hermetically sealed.

The model system doughs used in the described examples contain standard wheat flour and optimal amounts of water or buffer with or without the non-maltogenic PS4 variant exoamylase. They are mixed in a 10 or 50 g Brabender Farinograph for 6 or 7 min., respectively. Samples of the doughs are placed in glass test tubes (15*0.8 cm) with a lid. These test tubes are subjected to a baking process in a water bath starting with 30 min. incubation at 33° C. followed by heating from 33 to 95° C. with a gradient of 1.1° C. per min. and finally a 5 min. incubation at 95° C. Subsequently, the tubes are stored in a thermostat at 20° C. prior to DSC analysis.

In preferred embodiments, the PS4 variants described here have a reduced melting enthalpy, compared to the control. In highly preferred embodiments, the PS4 variants have a 10% or more reduced melting enthalpy. Preferably, they have a 20% or more, 30%, 40%, 50%, 60%, 70%, 80%, 90% or more reduced melting enthalpy when compared to the control.

TABLE 2

| | DSC (J/g) |
|---|---|
| Control | 2.29 |
| 0.5 D34 | 1.91 |
| 1 D34 | 1.54 |
| 2 D34 | 1.14 |

The above Table 2 shows DSC values of model dough systems prepared with different doses of PSac-D34 after 7 days of storage. 0.5, 1 and 2 parts per million (or microgram per gram) of flour are tested.

Preparation of Starch Products

We provide the use of PS4 variant polypeptides in the preparation of food products, in particular, starch products. The method comprises forming the starch product by adding a non-maltogenic exoamylase enzyme such as a PS4 variant polypeptide, to a starch medium. If the starch medium is a dough, then the dough is prepared by mixing together flour, water, the non-maltogenic exoamylase which is a PS4 variant polypeptide and optionally other possible ingredients and additives.

The term "starch" should be taken to mean starch per se or a component thereof, especially amylopectin. The term "starch medium" means any suitable medium comprising starch. The term "starch product" means any product that contains or is based on or is derived from starch. Preferably, the starch product contains or is based on or is derived from starch obtained from wheat flour. The term "flour" as used herein is a synonym for the finely-ground meal of wheat or other grain. Preferably, however, the term means flour obtained from wheat per se and not from another grain. Thus, and unless otherwise expressed, references to "wheat flour" as used herein preferably mean references to wheat flour per se as well as to wheat flour when present in a medium, such as a dough.

A preferred flour is wheat flour or rye flour or mixtures of wheat and rye flour. However, dough comprising flour derived from other types of cereals such as for example from rice, maize, barley, and durra are also contemplated. Preferably, the starch product is a bakery product. More preferably, the starch product is a bread product. Even more preferably, the starch product is a baked farinaceous bread product. The term "baked farinaceous bread product" refers to any baked product based on a dough obtainable by mixing flour, water, and a leavening agent under dough forming conditions. Further components can of course be added to the dough mixture.

Thus, if the starch product is a baked farinaceous bread product, then the process comprises mixing—in any suitable order—flour, water, and a leavening agent under dough forming conditions and further adding a PS4 variant polypeptide, optionally in the form of a premix. The leavening agent may be a chemical leavening agent such as sodium bicarbonate or any strain of *Saccharomyces cerevisiae* (Baker's Yeast).

The PS4 variant non-maltogenic exoamylase can be added together with any dough ingredient including the water or dough ingredient mixture or with any additive or additive mixture. The dough can be prepared by any conventional dough preparation method common in the baking industry or in any other industry making flour dough based products.

Baking of farinaceous bread products such as for example white bread, bread made from bolted rye flour and wheat flour, rolls and the like is typically accomplished by baking the bread dough at oven temperatures in the range of from 180 to 250° C. for about 15 to 60 minutes. During the baking process a steep temperature gradient (200→120° C.) is prevailing in the outer dough layers where the characteristic crust of the baked product is developed. However, owing to heat consumption due to steam generation, the temperature in the crumb is only close to 100° C. at the end of the baking process.

We therefore describe a process for making a bread product comprising: (a) providing a starch medium; (b) adding to the starch medium a PS4 variant polypeptide as described in this document; and (c) applying heat to the starch medium during or after step (b) to produce a bread product. We also describe a process for making a bread product comprising adding to a starch medium a PS4 variant polypeptide as described.

The non-maltogenic exoamylase PS4 variant polypeptide can be added as a liquid preparation or as a dry pulverulent composition either comprising the enzyme as the sole active component or in admixture with one or more additional dough ingredient or dough additive.

Improving Composition

We describe improver compositions, which include bread improving compositions and dough improving compositions. These comprise a PS4 variant polypeptide, optionally together with a further ingredient, or a further enzyme, or both.

We also provide for the use of such a bread and dough improving compositions in baling. In a further aspect, we provide a baked product or dough obtained from the bread improving composition or dough improving composition. In another aspect, we describe a baked product or dough obtained from the use of a bread improving composition or a dough improving composition.

Dough Preparation

A dough may be prepared by admixing flour, water, a dough improving composition comprising PS4 variant polypeptide (as described above) and optionally other ingredients and additives.

The dough improving composition can be added together with any dough ingredient including the flour, water or optional other ingredients or additives. The dough improving composition can be added before the flour or water or optional other ingredients and additives. The dough improving composition can be added after the flour or water, or optional other ingredients and additives. The dough can be prepared by any conventional dough preparation method common in the baking industry or in any other industry making flour dough based products.

The dough improving composition can be added as a liquid preparation or in the form of a dry powder composition either comprising the composition as the sole active component or in admixture with one or more other dough ingredients or additive.

The amount of the PS4 variant polypeptide non-maltogenic exoamylase that is added is normally in an amount which results in the presence in the finished dough of 50 to 100,000 units per kg of flour, preferably 100 to 50,000 units per kg of flour. Preferably, the amount is in the range of 200 to 20,000 units per kg of flour.

In the present context, 1 unit of the non-maltogenic exoamylase is defined as the amount of enzyme which releases hydrolysis products equivalent to 1 μmol of reducing sugar per min. when incubated at 50 degrees C. in a test tube with 4 ml of 10 mg/ml waxy maize starch in 50 mM MES, 2 mM calcium chloride, pH 6.0 as described hereinafter.

The dough as described here generally comprises wheat meal or wheat flour and/or other types of meal, flour or starch such as corn flour, corn starch, maize flour, rice flour, rye meal, rye flour, oat flour, oat meal, soy flour, sorghum meal, sorghum flour, potato meal, potato flour or potato starch. The dough may be fresh, frozen, or part-baked.

The dough may be a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae.*

The dough may comprise fat such as granulated fat or shortening. The dough may further comprise a further emulsifier such as mono- or diglycerides, sugar esters of fatty acids, polyglycerol esters of fatty acids, lactic acid esters of monoglycerides, acetic acid esters of monoglycerides, polyoxethylene stearates, or lysolecithin.

We also describe a pre-mix comprising flour together with the combination as described herein. The pre-mix may contain other dough-improving and/or bread-improving additives, e.g. any of the additives, including enzymes, mentioned herein.

Further Dough Additives or Ingredients

In order to improve further the properties of the baked product and impart distinctive qualities to the baked product further dough ingredients and/or dough additives may be incorporated into the dough. Typically, such further added components may include dough ingredients such as salt, grains, fats and oils, sugar or sweeteber, dietary fibres, protein sources such as milk powder, gluten soy or eggs and dough additives such as emulsifiers, other enzymes, hydrocolloids, flavouring agents, oxidising agents, minerals and vitamins The emulsifiers are useful as dough strengtheners and crumb softeners. As dough strengtheners, the emulsifiers can provide tolerance with regard to resting time and tolerance to shock during the proofing. Furthermore, dough strengtheners will improve the tolerance of a given dough to variations in the fermentation time. Most dough strengtheners also improve on the oven spring which means the increase in volume from the proofed to the baked goods. Lastly, dough strengtheners will emulsify any fats present in the recipe mixture.

Suitable emulsifiers include lecithin, polyoxyethylene stearat, mono- and diglycerides of edible fatty acids, acetic acid esters of mono- and diglycerides of edible fatty acids, lactic acid esters of mono- and diglycerides of edible fatty acids, citric acid esters of mono- and diglycerides of edible fatty acids, diacetyl tartaric acid esters of mono- and diglycerides of edible fatty acids, sucrose esters of edible fatty acids, sodium stearoyl-2-lactylate, and calcium stearoyl-2-lactylate.

The further dough additive or ingredient can be added together with any dough ingredient including the flour, water or optional other ingredients or additives, or the dough improving composition. The further dough additive or ingredient can be added before the flour, water, optional other ingredients and additives or the dough improving composition. The further dough additive or ingredient can be added after the flour, water, optional other ingredients and additives or the dough improving composition.

The further dough additive or ingredient may conveniently be a liquid preparation. However, the further dough additive or ingredient may be conveniently in the form of a dry composition.

Preferably the further dough additive or ingredient is at least 1% the weight of the flour component of dough. More preferably, the further dough additive or ingredient is at least 2%, preferably at least 3%, preferably at least 4%, preferably at least 5%, preferably at least 6%. If the additive is a fat, then typically the fat may be present in an amount of from 1 to 5%, typically 1 to 3%, more typically about 2%.

Further Enzyme

In addition to the PS4 variant polypeptides, one or more further enzymes may be used, for example added to the food, dough preparation, foodstuff or starch composition.

Further enzymes that may be added to the dough include oxidoreductases, hydrolases, such as lipases and esterases as well as glycosidases like α-amylase, pullulanase, and xylanase. Oxidoreductases, such as for example glucose oxidase and hexose oxidase, can be used for dough strengthening and control of volume of the baked products and xylanases and other hemicellulases may be added to improve dough handling properties, crumb softness and bread volume. Lipases are useful as dough strengtheners and crumb softeners and α-amylases and other amylolytic enzymes may be incorporated into the dough to control bread volume and further reduce crumb firmness.

Further enzymes that may be used may be selected from the group consisting of a cellulase, a hemicellulase, a starch degrading enzyme, a protease, a lipoxygenase.

Examples of useful oxidoreductases include oxidises such as maltose oxidising enzyme, a glucose oxidase (EC 1.1.3.4), carbohydrate oxidase, glycerol oxidase, pyranose oxidase, galactose oxidase (EC 1.1.3.10) and hexose oxidase (EC 1.1.3.5).

Among starch degrading enzymes, amylases are particularly useful as dough improving additives. α-amylase breaks downs starch into dextrins which are further broken down by β-amylase to maltose. Other useful starch degrading enzymes which may be added to a dough composition include glucoamylases and pullulanases.

Preferably, the further enzyme is at least a xylanase and/or at least an amylase. The term "xylanase" as used herein refers to xylanases (EC 3.2.1.32) which hydrolyse xylosidic linkages.

The term "amylase" as used herein refers to amylases such as α-amylases (EC 3.2.1.1), β-amylases (EC 3.2.1.2) and γ-amylases (EC 3.2.1.3.

The further enzyme can be added together with any dough ingredient including the flour, water or optional other ingredients or additives, or the dough improving composition. The further enzyme can be added before the flour, water, and optionally other ingredients and additives or the dough improving composition. The further enzyme can be added after the flour, water, and optionally other ingredients and additives or the dough improving composition. The further enzyme may conveniently be a liquid preparation. However, the composition may be conveniently in the form of a dry composition.

Some enzymes of the dough improving composition are capable of interacting with each other under the dough conditions to an extent where the effect on improvement of the rheological and/or machineability properties of a flour dough and/or the quality of the product made from dough by the enzymes is not only additive, but the effect is synergistic.

In relation to improvement of the product made from dough (finished product), it may be found that the combination results in a substantial synergistic effect in respect to crumb structure. Also, with respect to the specific volume of baked product a synergistic effect may be found.

The further enzyme may be a lipase (EC 3.1.1) capable of hydrolysing carboxylic ester bonds to release carboxylate. Examples of lipases include but are not limited to triacylglycerol lipase (EC 3.1.1.3), galactolipase (EC 3.1.1.26), phospholipase A1 (EC 3.1.1.32, phospholipase A2 (EC 3.1.1.4) and lipoprotein lipase A2 (EC 3.1.1.34).

Amylase Combinations

We disclose in particular combinations of PS4 variant polypeptides with amylases, in particular, maltogenic amylases. Maltogenic alpha-amylase (glucan 1,4-a-maltohydrolase, E.C. 3.2.1.133) is able to hydrolyze amylose and amylopectin to maltose in the alpha-configuration.

A maltogenic alpha-amylase from *Bacillus* (EP 120 693) is commercially available under the trade name Novamyl (Novo Nordisk A/S, Denmark) and is widely used in the baking industry as an anti-staling agent due to its ability to reduce retrogradation of starch. Novamyl is described in detail in International Patent Publication WO 91/04669. The maltogenic alpha-amylase Novamyl shares several characteristics with cyclodextrin glucanotransferases (CGTases), including sequence homology (Henrissat B, Bairoch A; Biochem. J., 316, 695-696 (1996)) and formation of transglycosylation products (Christophersen, C., et al., 1997, Starch, vol. 50, No. 1, 39-45).

In highly preferred embodiments, we disclose combinations comprising PS4 variant polypeptides together with Novamyl or any of its variants. Such combinations are useful for food production such as baking. The Novamyl may in particular comprise Novamyl 1500 MG.

Other documents describing Novamyl and its uses include Christophersen, C., Pedersen, S., and Christensen, T., (1993) Method for production of maltose an a limit dextrin, the limit dextrin, and use of the limit dextrin. Denmark, and WO 95/10627. It is further described in U.S. Pat. No. 4,598,048 and U.S. Pat. No. 4,604,355. Each of these documents is hereby incorporated by reference, and any of the Novamyl polypeptides described therein may be used in combinations with any of the PS4 variant polypeptides described here.

Variants, homologues, and mutants of Novamyl may be used for the combinations, provided they retain alpha amylase activity. For example, any of the Novamyl variants disclosed in U.S. Pat. No. 6,162,628, the entire disclosure of which is hereby incorporated by reference, may be used in combination with the PS4 variant polypeptides described here. In particular, any of the polypeptides described in that document, specifically variants of SEQ ID NO:1 of U.S. Pat. No. 6,162,628 at any one or more positions corresponding to Q13, I16, D17, N26, N28, P29, A30, S32, Y33, G34, L35, K40, M45, P73, V74, D76 N77, D79, N86, R95, N99, I100, H103, Qi 19, N120, N131, S141, T142, A148, N152, A163, H169, N171, G172, I174, N176, N187, F188, A192, Q201, N203, H220, N234, G236, Q247, K249, D261, N266, L268, R272, N275, N276, V279, N280, V281, D285, N287, F297, Q299, N305, K316, N320, L321, N327, A341, N342, A348, Q365, N371, N375, M378, G397, A381, F389, N401, A403, K425, N436, S442, N454, N468, N474, S479, A483, A486, V487, S493, T494, S495, A496, S497, A498, Q500, N507, I510, N513, K520, Q526, A555, A564, S573, N575, Q581, S583, F586, K589, N595, G618, N621, Q624, A629, F636, K645, N664 and/or T681 may be used.

Amino Acid Sequences

The invention makes use of a PS4 variant nucleic acid, and the amino acid sequences of such PS4 variant nucleic acids are encompassed by the methods and compositions described here.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The PS4 variant enzyme described here may be used in conjunction with other enzymes. Thus we further disclose a combination of enzymes wherein the combination comprises a PS4 variant polypeptide enzyme described here and another enzyme, which itself may be another PS4 variant polypeptide enzyme.

PS4 Variant Nucleotide Sequence

As noted above, we disclose nucleotide sequences encoding the PS4 variant enzymes having the specific properties described.

The term "nucleotide sequence" or "nucleic acid sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" as used in this document includes genomic DNA, cDNA, synthetic DNA, and RNA. Preferably it means DNA, more preferably cDNA sequence coding for a PS4 variant polypeptide.

Typically, the PS4 variant nucleotide sequence is prepared using recombinant DNA techniques (i.e. recombinant DNA). However, in an alternative embodiment, the nucleotide sequence could be synthesised, in whole or in part, using chemical methods well known in the art (see Caruthers M H et al., (1980) *Nuc Acids Res Symp Ser* 215-23 and Horn T et al., (1980) Nuc Acids Res Symp Ser 225-232).

Preparation of Nucleic Acid Sequences

A nucleotide sequence encoding either an enzyme which has the specific properties as defined herein (e.g., a PS4 variant polypeptide) or an enzyme which is suitable for modification, such as a parent enzyme, may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. maltose), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al.; (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (Science (1988) 239, pp 487-491).

Variants/Homologues/Derivatives

We further describe the use of variants, homologues and derivatives of any amino acid se ee of an enzyme or of any nucleotide sequence encoding such an enzyme, such a PS4 variant polypeptide or a PS4 variant nucleic acid. Unless the context dictates otherwise, the term "PS4 variant nucleic acid" should be taken to include each of the nucleic acid entities described below, and the term "PS4 variant polypeptide" should likewise be taken to include each of the polypeptide or amino acid entities described below.

Here, the term "homologue" means an entity having a certain homology with the subject amino acid sequences and the subject nucleotide sequences. Here, the term "homology" can be equated with "identity".

In the present context, a homologous sequence is taken to include an amino acid sequence which may be at least 75, 80, 85 or 90% identical, preferably at least 95, 96, 97, 98 or 99% identical to the subject sequence. Typically, the homologues will comprise the same active sites etc. as the subject amino acid sequence. Although homology can also be considered in terms of similarity (i.e. amino acid residues having similar chemical properties/functions), in the context of this document it is preferred to express homology in terms of sequence identity.

In the present context, an homologous sequence is taken to include a nucleotide sequence which may be at least 75, 80, 85 or 90% identical, preferably at least 95, 96, 97, 98 or 99% identical to a nucleotide sequence encoding a PS4 variant polypeptide enzyme (such as a PS4 variant nucleic acid). Typically, the homologues will comprise the same sequences that code for the active sites etc as the subject sequence. Although homology can also be considered in terms of similarity (i.e. amino acid residues having similar chemical properties/functions), in the context of this document it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungappped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 *Short Protocols in Molecular Biology,* 4$^{th}$ Ed—Chapter 18), FASTA (Altschul et al., 1990 *J. Mol. Biol.* 403-410) and the GENEWORKS suite of comparison tools. Both BLAST and FASTA are available for offline and online searching see Ausubel et al, 1999*, Short Protocols in Molecular Biology,* 7-58 to 7-60).

However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" *Comput. Appl Biosci.* 9: 745-756)(Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| Set | | Sub-set | |
|---|---|---|---|
| Hydrophobic | FWYHKMILVAGC | Aromatic | FWYH |
| | | Aliphatic | ILV |
| Polar | WYHKREDCSTNQ | Charged | HKRED |
| | | Positively charged | HKR |
| | | Negatively charged | ED |
| Small | VCAGSPTND | Tiny | AGS |

We further disclose sequences comprising homologous substitution (substitution and replacement are both used herein to mean the interchange of an existing amino acid residue, with an alternative residue) that may occur i.e. like for like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

The nucleotide sequences described here, and suitable for use in the methods and compositions described here (such as PS4 variant nucleic acids) may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of this document, it is to be understood that the nucleotide sequences described herein may be modified by any method available in the art. Such modifications may be carried out in order to enhance the in vivo activity or life span of nucleotide sequences.

We further describe the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the PS4 variant sequences may be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences described here.

Variants and strain/species homologues may also be obtained using degenerate PCR which will use primers designed to target sequences within the variants and homologues encoding conserved amino acid sequences. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides (nucleotide sequences) such as the PS4 variant nucleic acids described in this document may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides.

Polynucleotides such as DNA polynucleotides and probes may be produced recombinantly, synthetically, or by any means available to those of skill in the art. They may also be cloned by standard techniques. In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be design to contain suitable restriction enzyme recognition sites so that the amplified DNA can be cloned into a suitable cloning vector. Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

Hybridisation

We further describe sequences that are complementary to the nucleic acid sequences of PS4 variants or sequences that are capable of hybridising either to the PS4 variant sequences or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies. Therefore, we disclose the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M $Na_3$citrate pH 7.0}) to the nucleotide sequences presented herein. More preferably, the term "variant" encompasses sequences that are complementary to sequences that are capable of hybridising under high stringent conditions (e.g. 65° C. and 0.1×SSC {1×SSC=0.15 M NaCl, 0.015 M $Na_3$citrate pH 7.0}) to the nucleotide sequences presented herein.

We further disclose nucleotide sequences that can hybridise to the nucleotide sequences of PS4 variants (including complementary sequences of those presented herein), as well as nucleotide sequences that are complementary to sequences that can hybridise to the nucleotide sequences of PS4 variants (including complementary sequences of those presented herein). We further describe polynucleotide sequences that are capable of hybridising to the nucleotide sequences presented herein under conditions of intermediate to maximal stringency.

In a preferred aspect, we disclose nucleotide sequences that can hybridise to the nucleotide sequence of a PS4 variant nucleic acid, or the complement thereof, under stringent conditions (e.g. 50° C. and 0.2×SSC). More preferably, the nucleotide sequences can hybridise to the nucleotide sequence of a PS4 variant, or the complement thereof, under high stringent conditions (e.g. 65° C. and 0.1×SSC).

Site-Directed Mutagenesis

Once an enzyme-encoding nucleotide sequence has been isolated, or a putative enzyme-encoding nucleotide sequence has been identified, it may be desirable to mutate the sequence in order to prepare an enzyme. Accordingly, a PS4 variant sequence may be prepared from a parent sequence. Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151). A further method is described in Sarkar and Sommer (*Biotechniques* (1990), 8, p 404-407—"The megaprimer method of site directed mutagenesis").

In one aspect the sequence for use in the methods and compositions described here is a recombinant sequence—i.e. a sequence that has been prepared using recombinant DNA techniques. These recombinant DNA techniques are within the capabilities of a person of ordinary skill in the art. Such techniques are explained in the literature, for example, J. Sambrook, E. F. Fritsch, and T. Maniatis, 1989, Molecular Cloning: A Laboratory Manual, Second Edition, Books 1-3, Cold Spring Harbor Laboratory Press.

In one aspect the sequence for use in the methods and compositions described here is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

The nucleotide sequence for use in the methods and compositions described here may be incorporated into a recombinant replicable vector. The vector may be used to replicate and express the nucleotide sequence, in enzyme form, in and/or from a compatible host cell. Expression may be controlled using control sequences eg. regulatory sequences. The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression of PS4 Nucleic Acids and Polypeptides

The PS4 polynucleotides and nucleic acids may include DNA and RNA of both synthetic and natural origin which DNA or RNA may contain modified or unmodified deoxy- or dideoxy-nucleotides or ribonucleotides or analogs thereof. The PS4 nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides. The PS4 nucleic acid may even be codon optimised to further increase expression.

The term "synthetic", as used herein, is defined as that which is produced by in vitro chemical or enzymatic synthesis. It includes but is not limited to PS4 nucleic acids made with optimal codon usage for host organisms such as the methylotrophic yeasts *Pichia* and *Hansenula*.

Polynucleotides, for example variant PS4 polynucleotides described here, can be incorporated into a recombinant replicable vector. The vector may be used to replicate the nucleic acid in a compatible host cell. The vector comprising the polynucleotide sequence may be transformed into a suitable host cell. Suitable hosts may include bacterial, yeast, insect and fungal cells.

The term “transformed cell” includes cells that have been transformed by use of recombinant DNA techniques. The transformation typically occurs by insertion of one or more nucleotide sequences into a cell that is to be transformed. The inserted nucleotide sequence may be a heterologous nucleotide sequence (i.e. is a sequence that is not natural to the cell that is to be transformed. In addition, or in the alternative, the inserted nucleotide sequence may be an homologous nucleotide sequence (i.e. is a sequence that is natural to the cell that is to be transformed)—so that the cell receives one or more extra copies of a nucleotide sequence already present in it.

Thus in a further embodiment, we provide a method of making PS4 variant polypeptides and polynucleotides by introducing a polynucleotide into a replicable vector, introducing the vector into a compatible host cell, and growing the host cell under conditions which bring about replication of the vector. The vector may be recovered from the host cell.

Expression Constructs

The PS4 nucleic acid may be operatively linked to transcriptional and translational regulatory elements active in a host cell of interest. The PS4 nucleic acid may also encode a fusion protein comprising signal sequences such as, for example, those derived from the glucoamylase gene from *Schwanniomyces occidentalis*, α-factor mating type gene from *Saccharomyces cerevisiae* and the TAKA-amylase from *Aspergillus oryzae*. Alternatively, the PS4 nucleic acid may encode a fusion protein comprising a membrane binding domain.

Expression Vector

The PS4 nucleic acid may be expressed at the desired levels in a host or organism using an expression vector.

An expression vector comprising a PS4 nucleic acid can be any vector which is capable of expressing the gene encoding PS4 nucleic acid in the selected host organism, and the choice of vector will depend on the host cell into which it is to be introduced. Thus, the vector can be an autonomously replicating vector, i.e. a vector that exists as an episomal entity, the replication of which is independent of chromosomal replication, such as, for example, a plasmid, a bacteriophage or an episomal element, a minichromosome an artificial chromosome. Alternatively, the vector may be one which, when introduced into a host cell, is integrated into the host cell genome and replicated together with the chromosome.

Components of the Expression Vector

The expression vector typically includes the components of a cloning vector, such as, for example, an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. Additionally, the expression vector may comprise a sequence coding for an amino acid sequence capable of targeting the PS4 variant polypeptide to a host cell organelle such as a peroxisome or to a particular host cell compartment. Such a targeting sequence includes but is not limited to the sequence SKL. In the present context, the terin “expression signal” includes any of the above control sequences, repressor or activator sequences. For expression under the direction of control sequences, the nucleic acid sequence the PS4 variant polypeptide is operably linked to the control sequences in proper manner with respect to expression.

Preferably, a polynucleotide in a vector is operably linked to a control sequence that is capable of providing for the expression of the coding sequence by the host cell, i.e. the vector is an expression vector. The term “operably linked” means that the components described are in a relationship permitting them to function in their intended manner. A regulatory sequence “operably linked” to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators. The control sequences may in particular comprise promoters.

Promoter

In the vector, the nucleic acid sequence encoding for the variant PS4 polypeptide is operably combined with a suitable promoter sequence. The promoter can be any DNA sequence having transcription activity in the host organism of choice and can be derived from genes that are homologous or heterologous to the host organism.

Bacterial Promoters

Examples of suitable promoters for directing the transcription of the modified nucleotide sequence, such as PS4 nucleic acids, in a bacterial host include the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes and a promoter derived from a *Lactococcus* sp.-derived promoter including the P170 promoter. When the gene encoding the PS4 variant polypeptide is expressed in a bacterial species such as *E. coli*, a suitable promoter can be selected, for example, from a bacteriophage promoter including a T7 promoter and a phage lambda promoter.

Fungal Promoters

For transcription in a fungal species, examples of useful promoters are those derived from the genes encoding the, *Aspergillus oryzae* TAKA amylase, *Rhizomucor miehei* aspartic proteinase, *Aspergillus niger* neutral α-amylase, *A. niger* acid stable α-amylase, *A. niger glucoamylase, Rhizomucor miehei lipase, Aspergillus oryzae* alkaline protease, *Aspergillus oryzae* triose phosphate isomerase or *Aspergillus nidulans* acetamidase.

Yeast Promoters

Examples of suitable promoters for the expression in a yeast species include but are not limited to the Gal 1 and Gal 10 promoters of *Saccharomyces cerevisiae* and the *Pichia pastoris* AOX1 or AOX2 promoters.

Host Organisms (I) Bacterial Host Organisms

Examples of suitable bacterial host organisms are gram positive bacterial species such as Bacillaceae including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus lautus, Bacillus megaterium* and *Bacillus thuringiensis, Streptomyces* species such as *Streptomyces murinus*, lactic acid bacterial species including *Lactococcus* spp. such as *Lactococcus lactis, Lactobacillus* spp. including *Lactobacillus reuteri, Leuconostoc* spp., *Pediococcus* spp. and *Streptococcus* spp. Alternatively, strains of a gram-negative bacterial species belonging to Enterobacteriaceae including *E. coli*, or to Pseudomonadaceae can be selected as the host organism.

(II) Yeast Host Organisms

A suitable yeast host organism can be selected from the biotechnologically relevant yeasts species such as but not limited to yeast species such as *Pichia* sp., *Hansenula* sp or *Kluyveromyces, Yarrowinia* species or a species of *Saccharomyces* including *Saccharomyces cerevisiae* or a species belonging to *Schizosaccharomyce* such as, for example, *S. Pombe* species.

Preferably a strain of the methylotrophic yeast species *Pichia pastoris* is used as the host organism. Preferably the host organism is a *Hansenula* species.

(III) Fungal Host Organisms

Suitable host organisms among filamentous fungi include species of *Aspergillus*, e.g. *Aspergillus niger, Aspergillus oryzae, Aspergillus tubigensis, Aspergillus awamori* or *Aspergillus nidulans*. Alternatively, strains of a *Fusarium* species, e.g. *Fusarium oxysporum* or of a *Rhizomucor* species such as *Rhizomucor miehei* can be used as the host organism. Other suitable strains include *Thermomyces* and *Mucor* species.

Protein Expression and Purification

Host cells comprising polynucleotides may be used to express polypeptides, such as variant PS4 polypeptides, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Polypeptides can be extracted from host cells by a variety of techniques known in the art, including enzymatic, chemical and/or osmotic lysis and physical disruption. Polypeptides may also be produced recombinantly in an in vitro cell-free system, such as the TnT™ Promega) rabbit reticulocyte system.

EXAMPLES

Example 1

Cloning of PS4

*Pseudomonas sacharophila* is grown overnight on LB media and chromosomal DNA is isolated by standard methods (Sambrook J, 1989). A 2190 bp fragment containing the PS4 open reading frame (Zhou et al., 1989) is amplified from *P. sacharophila* chromosomal DNA by PCR using the primers P1 and P2 (see Table 3). The resulting fragment is used as a template in a nested PCR with primers P3 and P4, amplifying the openreading frame of PS4 without its signal sequence and introducing a NcoI site at the 5' end of the gene and a BamHI site at the 3' end. Together with the NcoI site a codon for a N-terminal Methionine is introduced, allowing for intracellular expression of PS4. The 1605 bp fragment is cloned into pCRBLUNT TOPO (Invitrogen) and the integrity of the construct analysed by sequencing. The *E. coli Bacillus* shuttle vector pDP66K (Penning a et al., 1996) is modified to allow for expression of the PS4 under control of the P32 promoter and the ctgase signal sequence. The resulting plasmid, pCSmta is transformed into *B. subtlis.*

A second expression construct is made in which the starch binding domain of PS4 is removed. In a PCR with primers P3 and P6 (Table 3) on pCSmta, a truncated version of the mta gene is generated. The full length mta gene in pCSmta is exchanged with the truncated version which resulted in the plasmid pCSmta-SBD.

Example 2

Site Directed Mutagenesis of PS4

Mutations are introduced into the mta gene by 2 methods. Either by a 2 step PCR based method, or by a Quick Exchange method (QE). For convenience the mta gene is split up in 3 parts; a PvuI-FspI fragment, a FspI-PstI fragment and a PstI-AspI fragment, further on referred to as fragment 1, 2 and 3 respectively.

In the 2 step PCR based method, mutations are introduced using Pfu DNA polymerase (Stratagene). A first PCR is carried out with a mutagenesis primer (Table 4) for the coding strand plus a primer downstream on the lower strand (either 2R or 3R Table 3). The reaction product is used as a primer in a second PCR together with a primer upstream on the coding strand. The product of the last reaction is cloned into pCR-BLUNT topo (Invitrogen) and after sequencing the fragment is exchanged with the corresponding fragment in pCSmta.

Using the Quick Exchange method (Stratagene), mutations are introduced using two complementary primers in a PCR on a plasmid containing the mta gene, or part of the mta gene.

For this purpose a convenient set of plasmids is constructed, comprising of 3 SDM plasmids and 3 pCSΔ plasmids. The SDM plasmids each bear 1 of the fragments of the mta gene as mentioned above, in which the desired mutation is introduced by QE. After verification by sequencing, the fragments are cloned into the corresponding recipient pCSΔ plasmid. The pCSΔ plasmids are inactive derivatives from pCSmta. Activity is restored by cloning the corresponding fragment from the SDM plasmid, enabling easy screening.

TABLE 3

Primers used in cloning the mta gene, and standard primers used in construction of site directed mutants with the 2 step PCR method.

| Primer | Primer sequence | Introduced site |
|---|---|---|
| P1 | 5'-ATG ACG AGG TCC TTG TTT TTC (SEQ ID NO: 42) | |
| P2 | 5'-CGC TAG TCG TCC ATG TCG (SEQ ID NO: 43) | |
| P3 | 5'-GCC ATG GAT CAG GCC GGC AAG AGC CCG (SEQ ID NO: 44) | NcoI |
| P4 | 5'-TGG ATC CTC AGA ACG AGC CGC TGG T (SEQ ID NO: 458) | BamHI |
| P6 | 5'-GAA TTC AGC CGC CGT CAT TCC CGC C (SEQ ID NO: 46) | EcoRI |
| 2L | 5'-AGA TTT ACG GCA TGT TTC GC (SEQ ID NO: 47) | |
| 2R | 5'-TAG CCG CTA TGG AAG CTG AT (SEQ ID NO: 48) | |
| 3L | 5'-TGA CCT TCG TCG ACA ACC AC (SEQ ID NO: 49) | |
| 3R | 5'-GAT AGC TGC TGG TGA CGG TC (SEQ ID NO: 50) | |

TABLE 4

| Primers used to introduce site directed mutations in mta | | | | |
|---|---|---|---|---|
| Mutation | Oligo Sequence | Modification | Strand | Purpose |
| G134R | CTGCCGGCCGGCCAGcGCTTCTGGCG (SEQ ID NO: 51) | | + | SDM |
| G134R - | Cgccagaagcgctggccggccggcag (SEQ ID NO: 52) | | - | SDM |
| I157L | GACGGTGACCGCTTCcTgGGCGGCGAGTCG (SEQ ID NO: 53) | | + | SDM |
| I151L - | Cgactcgccgcccaggaagcggtcaccgtc (SEQ ID NO: 54) | | - | SDM |
| G223A | GGCGAGCTGTGGAAAgccCCTTCTGAATATCCG (SEQ ID NO: 55) | | + | SDM |
| G223A - | Cggatattcagaaggggctttccacagctcgcc (SEQ ID NO: 56) | | - | SDM |
| H307L | gaacGGCGGCCAGCACctgTGGGCGCTGCAG (SEQ ID NO: 57) | | + | SDM |
| H307L - | Ctgcagcgcccacaggtgctggccgccgttc (SEQ ID NO: 58) | | - | SDM |
| S334P, D343E | GTACTGGccgCACATGTACGACTGGGGCTACGGC gaaTTCATC (SEQ ID NO: 59) | | + | SDM |
| S334P, D343E - | Gatgaattcgccgtagccccagtcgtacatgtgc ggccagtac (SEQ ID NO: 60) | | - | SDM |

TABLE 5

| Features of the SDM and pCSΔ plasmids | |
|---|---|
| Plasmid | Features/construction |
| SDM1 | pBlueSK+ 480 bp SalI-StuI fragment mta |
| SDM2 | pBlueSK+ 572 bp SacII-PstI fragment mta |
| SDM3 | pBlueSK+ 471 bp SalI-StuI fragment mta |
| pCSΔ1 | FseI site filled in with Klenow ---> frameshift in mta |
| pCSΔ2 | FspI-PstI fragment of mta replaced with 'junk-DNA' |
| pCSΔ3 | PstI-AspI fragment of mta replaced with 'junk-DNA' |

Example 3

Multi SDM

The PS4 variants were generated using a QuickChange® Multi Site Directed Mutagenesis Kit (Stratagene) according to the manufactures protocol with some modifications as described.

Step 1: Mutant Strand Synthesis Reaction (PCR)

Inoculate 3 ml. LB (22 g/l Lennox L Broth Base, Sigma)+ antibiotics (0.05 µg/ml kanamycin, Sigma) in a 10 ml Falcon tube Incubate o/n 37° C., ca. 200 rpm.

Spin down the cells by centrifugation (5000 rpm/5 min)

Poor off the medium

Prepare ds-DNA template using QIAGEN Plasmid Mini Purification Protocol

1. The mutant strand synthesis reaction for thermal cycling was prepared as follow:

PCR Mix:

| | | |
|---|---|---|
| 2.5 µl | 10× QuickChange ® Multi reaction buffer | |
| 0.75 µl | QuickSolution | |
| X µl | Primers | primer length 28-35 bp → 10 pmol |
| | | primer length 24-27 bp → 7 pmol |
| | | primer length 20-23 bp → 5 pmol |
| 1 µl | dNTP mix | |
| X µl | ds-DNA template (200 ng) | |
| 1 µl | QuickChange ® Multi enzyme blend (2.5 U/µl) (PfuTurbo ® DNA polymerase) | |
| X µl | $dH_2O$ (to a final volume of 25 µl) | |

Mix all components by pipetting and briefly spin down the reaction mixtures.

2. Cycle the reactions using the following parameters:
   35 cycles of denaturation (96° C./1 min)
   primer annealing (62.8° C./1 min)
   elongation (65° C./15 min)
   then hold at 4° C.

Preheat the lid of the PCR machine to 105° C. and the plate to 95° C. before the PCR tubes are placed in the machine (eppendorf thermal cycler).

Step 2: Dpn I Digestion

1. Add 2 µl Dpn I restriction enzyme (10 U/µl) to each amplification reaction, mix by pipetting and spin down mixture.
2. Incubate at 37° C. for ~3 hr.

Step 3: Transformation of XL10-Gold® Ultracompetent Cells

1. Thaw XL10-Gold cells on ice. Aliquot 45 µl cells per mutagenesis reaction to prechilled Falcon tubes.

2. Turn on the waterbath (42° C.) and place a tube with NZY+ broth in the bath to preheat.
3. Add 2 µl β-mercaptoethanol mix to each tube. Swirl and tap gently and incubate 10 min on ice, swirling every 2 min.
4. Add 1.5 µl Dpn I-treated DNA to each aliquot of cells, swirl to mix and incubate on ice for 30 nm.
5. Heat-pulse the tubes in 42° C. waterbath for 30 s and place on ice for 2 min.
6. Add 0.5 ml preheated NZY+ broth to each tube and incubate at 37° C. for 1 hr with shaking at 225-250 rpm.
7. Plate 200 µl of each transformation reaction on LB plates (33.6 g/l Lennox L Agar, Sigma) containing 1% starch and 0.05 µg/ml kanamycin
8. Incubate the transformation plates at 37° C. overnight.

TABLE 6

Primer table for pPD77d14:

| Mutation | Oligo Sequence | Modification | Strand | Purpose |
|---|---|---|---|---|
| N33Y, D34N | GCGAAGCGCCCTACAACTGGTACAAC (SEQ ID NO: 61) | 5' phosphate | + | MSDM |
| K71R | CCGACGGCGGCAGGTCCGGCG (SEQ ID NO: 62) | 5' phosphate | + | MSDM |
| G87S | CAAGAACAGCCGCTACGGCAGCGAC (SEQ ID NO: 63) | 5' phosphate | + | MSDM |
| G121D | CACATGAACCGCGACTACCCGGACAAG (SEQ ID NO: 64) | 5' phosphate | + | MSDM |
| G134R | CTGCCGGCCGGCCAGcGCTTCTGGCG (SEQ ID NO: 65) | 5' phosphate | + | MSDM |
| A141P | CGCAACGACTGCGCCGACCCGGG (SEQ ID NO: 66) | 5' phosphate | + | MSDM |
| I157L | GACGGTGACCGCTTCcTgGGCGGCGAGTCG (SEQ ID NO: 67) | 5' phosphate | + | MSDM |
| L178F, A179T | CGCGACGAGTTTACCAACCTGCG (SEQ ID NO: 68) | 5' phosphate | + | MSDM |
| G223A | GGCGAGCTGTGGAAAgccCCTTCTGAATATCCG (SEQ ID NO: 69) | 5' phosphate | + | MSDM |
| H307L | gaacGGCGGCCAGCACctgTGGGCGCTGCAG (SEQ ID NO: 70) | 5' phosphate | + | MSDM |
| S334P, D343E | GTACTGGccgCACATGTACGACTGGGGCTACGGCgaaTTCATC (SEQ ID NO: 71) | 5' phosphate | + | MSDM |

TABLE 7

Primer table for pPD77d20:

| Mutation | Oligo Sequence | Modification | Strand | Purpose |
|---|---|---|---|---|
| N33Y, D34N | GCGAAGCGCCCTACAACTGGTACAAC (SEQ ID NO: 61) | 5' phosphate | + | MSDM |
| K71R | CCGACGGCGGCAGGTCCGGCG (SEQ ID NO: 62) | 5' phosphate | + | MSDM |
| G121D | CACATGAACCGCGACTACCCGGACAAG (SEQ ID NO: 64) | 5' phosphate | + | MSDM |
| G134R | CTGCCGGCCGGCCAGcGCTTCTGGCG (SEQ ID NO: 65) | 5' phosphate | + | MSDM |
| A141P | CGCAACGACTGCGCCGACCCGGG (SEQ ID NO: 66) | 5' phosphate | + | MSDM |
| I157L | GACGGTGACCGCTTCcTgGGCGGCGAGTCG (SEQ ID NO: 67) | 5' phosphate | + | MSDM |
| L178F, A179T | CGCGACGAGTTTACCAACCTGCG (SEQ ID NO: 68) | 5' phosphate | + | MSDM |

TABLE 7-continued

| Primer table for pPD77d20: | | | | |
|---|---|---|---|---|
| Mutation | Oligo Sequence | Modification | Strand | Purpose |
| G223A | GGCGAGCTGTGGAAAgccCCTTCTGAATATCCG (SEQ ID NO: 69) | 5' phosphate | + | MSDM |
| H307L | gaacGGCGGCCAGCACctgTGGGCGCTGCAG (SEQ ID NO: 70) | 5' phosphate | + | MSDM |
| S334P, D343E | GTACTGGccgCACATGTACGACTGGGGCTACGGC gaaTTCATC (SEQ ID NO: 71) | 5' phosphate | + | MSDM |

TABLE 8

| Primer table for pPD77d34 (pSac-D34) | | | | |
|---|---|---|---|---|
| Mutation | Oligo Sequence | Modification | Strand | Purpose |
| N33Y, D34N | GCGAAGCGCCCTACAACTGGTACAAC (SEQ ID NO: 61) | 5' phosphate | + | MSDM |
| G121D | CACATGAACCGCGACTACCCGGACAAG (SEQ ID NO: 64) | 5' phosphate | + | MSDM |
| G134R | CTGCCGGCCGGCCAGcGCTTCTGGCG (SEQ ID NO: 65) | 5' phosphate | + | MSDM |
| A141P | CGCAACGACTGCGCCGACCCGGG (SEQ ID NO: 66) | 5' phosphate | + | MSDM |
| I157L | GACGGTGACCGCTTCcTgGGCGGCGAGTCG (SEQ ID NO: 67) | 5' phosphate | + | MSDM |
| L178F, A179T | CGCGACGAGTTTACCAACCTGCG (SEQ ID NO: 68) | 5' phosphate | + | MSDM |
| G223A | GGCGAGCTGTGGAAAgccCCTTCTGAATATCCG (SEQ ID NO: 69) | 5' phosphate | + | MSDM |
| H307L | gaacGGCGGCCAGCACctgTGGGCGCTGCAG (SEQ ID NO: 70) | 5' phosphate | + | MSDM |
| S334P | GTACTGGccgCACATGTACGACTGGGGCTACGGC (SEQ ID NO: 72) | 5' phosphate | + | MSDM |

Vector System Based on pPD77

The vector system used for pPD77 is based on pCRblunt-TOPOII (invitrogen). The zeocin resistance cassette has been removed by pmlI, 393 bp fragment removed. The expression cassette from the pCC vector (P32-ssCGTase-PS4-tt) has then been inserted into the vector.

Ligation of PS4 Variant into pCCMini

The plasmid which contain the relevant mutations (created by MSDM) is cut with restriction enzyme Nco 1 and Hind III (Biolabs):

3 μg plasmid DNA, X μl 10× buffer 2, 10 units Nco1, 20 units HindIII,

Incubation 2 h at 37° C.

Run digestion on a 1% agarose gel. Fragments sized 1293 bp (PS4 gene) is cut out of the gel and purified using Qiagen gel purification kit.

The vector pCCMini is then cut with restriction enzymes, Nco 1 and Hind III, and the digestion is then run on a 1% agarose gel. The fragment sized 3569 bp is cut out of the gel and purified using Qiagen gel purification kit.

Ligation: Use Rapid DNA ligation kit (Roche)

Use the double amount of insert compared to vector e.g. 2 pt insert (PS4 gene)

1 μl vector

5 μl T4 DNA ligation buffer 2×conc

1 μl $dH_2O$

1 μl T4 DNA ligase

Ligate-5 min/RT

Transform the ligation into One Shot TOPO competent cells according to manufactures protocol (Invitrogen). Use 5 μl ligation pr. transformation.

Plate 50 μl transformations mix onto LB plates (33.6 g/l Lennox L Agar, Sigma) containing 1% starch and 0.05 μg/ml kanamycin. Vectors containing insert (PS4 variants) can be recognised by halo formation on the starch plates.

Example 4

Transformation into *Bacillus subtilis* (Protoplast Transformation)

*Bacillus subtilis* (strain DB104A; Smith et al. 1988; Gene 70, 351-361) is transformed with the mutated pCS-plasmids according to the following protocol.

A. Media for Protoplasting and Transformation

| | |
|---|---|
| 2 × SMM | per liter: 342 g sucrose (1 M); 4.72 g sodium maleate (0.04M); 8:12 g $MgCl_2$, $6H_20$ (0.04M); pH 6.5 with concentrated NaOH. Distribute in 50-ml portions and autoclave for 10 min. |
| 4 × YT | 2 g Yeast extract + 3.2 g Tryptone + 0.5 g NaCl per 100 ml. |
| (½ NaCl) | mix equal volumes of 2 × SMM and 4 × YT. |
| SMMP | 10 g polyethyleneglycol 6000 (BDH) or 8000 (Sigma) |
| PEG | in 25 ml 1 × SMM (autoclave for 10 min.). |

B. Media for Plating/Regeneration

| | |
|---|---|
| agar | 4% Difco minimal agar. Autoclave for 15 min. |
| sodium succinate | 270 g/l (1M), pH 7.3 with HCl. Autoclave for 15 min. |
| phosphate buffer | 3.5 g $K_2HPO_4$ + 1.5 g $KH_2PO_4$ per 100 ml. Autoclave for 15 min. |
| $MgCl_2$ | 20.3 g $MgCl_2$, $6H_2O$ per 100 ml (1M). |
| casamino acids | 5% (w/v) solution. Autoclave for 15 min. |
| yeast extract | 10 g per 100 ml, autoclave for 15 min. |
| glucose | 20% (w/v) solution. Autoclave for 10 min. |

DM3 regeneration medium: mix at 60 C (waterbath; 500-ml bottle):

250 ml sodium succinate
50 ml casamino acids
25 ml yeast extract
50 ml phosphate buffer
15 ml glucose
10 ml $MgCl_2$
100 ml molten agar Add appropriate antibiotics: chloramphenicol and tetracycline, 5 ug/ml; erytliromycin, 1 ug/ml. Selection on kanamycin is problematic in DM3 medium: concentrations of 250 ug/ml may be required.

C. Preparation of Protoplasts

1. Use detergent-free plastic or glassware throughout.

2. Inoculate 10 ml of 2×YT medium in a 100-ml flask from a single colony. Grow an overnight culture at 25-30 C in a shaker (200 rev/min).

3. Dilute the overnight culture 20 fold into 100 ml of fresh 2×YT medium (250-ml flask) and grow until $OD_{600}$=0.4-0.5 (approx. 2h) at 37 C in a shaker (200-250 rev/min).

4. Harvest the cells by centrifugation (9000 g, 20 min, 4 C).

5. Remove the supernatant with pipette and resuspend the cells in 5 ml of SMMP+5 mg lysozyme, sterile filtered.

6. Incubate at 37 C in a waterbath shaker (100 rev/min).

After 30 min and thereafter at 15 min intervals, examine 25 ul samples by microscopy. Continue incubation until 99% of the cells are protoplasted (globular appearance). Harvest the protoplasts by centrifugation (4000 g, 20 min, RT) and pipet off the supernatant. Resuspend the pellet gently in 1-2 ml of SMMP.

The protoplasts are now ready for use. (Portions (e.g. 0.15 ml) can be frozen at −80 C for future use (glycerol addition is not required). Although this may result in some reduction of transformability, 106 transformants per ug of DNA can be obtained with frozen protoplasts).

D. Transformation

1. Transfer 450 ul of PEG to a microtube.

2. Mix 1-10 ul of DNA (0.2 ug) with 150 ul of protoplasts and add the mixture to the microtube with PEG. Mix immediately, but gently.

3. Leave for 2 min at RT, and then add 1.5 ml of SMMP and mix.

4. Harvest protoplasts by microfuging (10 min, 13.000 rev/min (110-12.000 g)) and pour off the supernatant. Remove the remaining droplets with a tissue.

Add 300 ul of SMMP (do not vortex) and incubate for 60-90 min at 37 C in a waterbath shaker (100 rev/min) to allow for expression of antibiotic resistance markers. (The protoplasts become sufficiently resuspended through the shaking action of the waterbath.). Make appropriate dilutions in 1×SSM and plate 0.1 ml on DM3 plates Example 5

Fermentation of PS4 Variants in Shake Flasks

The shake flask substrate is prepared as follows:

| Ingredient | % (w/v) |
|---|---|
| Water | — |
| Yeast extract | 2 |
| Soy Flour | 2 |
| NaCl | 0.5 |
| Dipotassium phosphate | 0.5 |
| Antifoam agent | 0.05 |

The substrate is adjusted to pH 6.8 with 4N sulfuric acid or sodium hydroxide before autoclaving. 100 ml of substrate is placed in a 500 ml flask with one baffle and autoclaved for 30 minutes. Subsequently, 6 ml of sterile dextrose syrup is added. The dextrose syrup is prepared by mixing one volume of 50% w/v dextrose with one volume of water followed by autoclaving for 20 minutes.

The shake flask are inoculated with the variants and incubated for 24 hours at 35° C./180 rpm in an incubator. After incubation cells are separate from broth by centrifugation (10.000×g in 10 minutes) and finally, the supernatant is made cell free by microfiltration at 0.2 µm. The cell free supernatant is used for assays and application tests.

Example 6

Amylase Assays

Betamyl assay

One Betamyl unit is defined as activity degrading 0.0351 mmole per 1 min. of PNP-coupled maltopentaose so that 0.0351 mmole PNP per 1 min. can be released by excess a-glucosidase in the assay mix. The assay mix contains 50 ul 50 mM Na-citrate, 5 mM $CaCl_2$, pH 6.5 with 25 ul enzyme sample and 25 ul Betamyl substrate (GlcS-PNP and a-glucosidase) from Megazyme, Ireland (1 vial dissolved in 10 ml water). The assay mix is incubated for 30 min. at 40 C and then stopped by adding 150 ul 4% Tris. Absorbance at 420 nm is measured using an ELISA-reader and the Betamyl activity is calculate based on Activity=A420*d in Betarnyl units/ml of enzyme sample assayed.

Endo-Amylase Assay

The endo-amylase assay is identical to the Phadebas assay run according to manufacturer (Pharmacia & Upjohn Diagnostics AB).

Exo-Specificity

The ratio of exo-amylase activity to Phadebas activity was used to evaluate exo-specificity.

Specific Activity

For the PSac-D14, PSac-$D_2O$ and PSac-D34 variants we find an average specific activity of 10 Betamyl units per microgram of purified protein measured according to Bradford (1976; Anal. Biochem. 72, 248). This specific activity is used for based on activity to calculate the dosages used in the application trials.

Example 7

Half-life Determination t½ is defined as the time (in minutes) during which half the enzyme activity is inactivated under defined heat conditions. In order to determine the half life of the enzyme, the sample is heated for 1-10 minutes at constant temperatures of 60° C. to 90° C. The half life is calculated based on the residual Betamyl assay.

Procedure: In an Eppendorf vial, 1000 μl buffer is pre-heated for at least 10 minutes at 60° C. or higher. The heat treatment of the sample is started addition of 100 μl of the sample to the preheated buffer under continuous mixing (800 rpm) of the Eppendorf vial in an heat incubator (Termomixer comfort from Eppendorf). After 0, 2, 4, 6, 8 and 9 minutes of incubation, the treatment is stopped by transferring 45 μl of the sample to 1000 μl of the buffer equilibrated at 20° C. and incubating for one minute at 1500 rpm and at 20° C. The residual activity is measured with the Betamyl assay.

Calculation: Calculation of t½ is based on the slope of log 10 (the base −10 logarithm) of the residual Betamyl activity versus the incubation time. t½ is calculated as Slope/0.301=t½.

Example 8

Results

TABLE 9

Biochemical properties of PSac-variants compared to wild-type PSac-cc1

| Variant | t½-75 | t½-80 | Betamyl/ Phadebas | Mutations |
|---|---|---|---|---|
| PSac-cc1 | <0.5 | | 40 | |
| PSac-D3 | 9.3 | 3 | 43 | N33Y, D34N, K71R, G134R, A141P, I157L, L178F, A179T, G223A, H307L, D343E, S334P |
| PSac-D14 (SEQ ID NO: 4) | 9.3 | 2.7 | 65 | N33Y, D34N, K71R, G87S, G121D, G134R, A141P, I157L, L178F, A179T, G223A, H307L, D343E, S334P |
| PSac-D20 (SEQ ID NO: 3) | 7.1 | 2.7 | 86 | N33Y, D34N, K71R, G121D, G134R, A141P, I157L, L178F, A179T, G223A, H307L, D343E, S334P |
| PSac-D34 (SEQ ID NO: 2) | 8.4 | 2.9 | 67 | N33Y, D34N, G121D, G134R, A141P, I157L, L178F, A179T, G223A, H307L, S334P |
| PSac-pPD77d10 | 3.7 | | 61 | G121D, G134R, A141P, I157L, G223A, H307L, S334P, D343E |
| PSac-pPD77d32 | | 2.5 | 52 | G134R, A141P, I157L, G223A, H307L, S334P, L178F + A179T |
| PSac-pPD77d33 | 7.1 | 3 | 51 | N33Y, D34N, G134R, A141P, I157L, L178F, A179T, G223A, H307L, S334P |
| PSac-pPD77d36 | | 2.8 | 77 | G87S, G121D, G134R, A141P, I157L, G223A, H307L, S334P, K71R, L178F, A179T |
| PSac-pPD77d38 | 7.9 | 2.5 | 77 | G121D, G134R, A141P, I157L, G223A, H307L, S334P, L178F + A179T |
| PSac-pPD77d40 | 10.26 | 3.1 | 63 | N33Y D34N K71R G121D G134R A141P I157L L178F + A179T G223A H307L S334P |

Experiments are done with versions of each of the variants listed in the table above, but without mutations are position 33 (i.e., having wild type residue N at this position). Similar results are obtained for such versions, as for those with mutation N33Y.

Experiments are also done with versions of each of the variants listed in the table above, but without mutations are position 34 (i.e., having wild type residue D at this position). Similar results are obtained for such versions, as for those with mutation D34N.

Example 9

Model System Baking Tests

The doughs are made in the Farinograph at 30.0° C. 10.00 g reformed flour is weighed out and added in the Farinograph; after 1 min. mixing the reference/sample (reference=buffer or water, sample=enzyme+buffer or water) is added with a sterile pipette through the holes of the kneading vat. After 30 sec. the flour is scraped off the edges—also through the holes of the kneading vat. The sample is kneaded for 7 min.

A test with buffer or water is performed on the Farinograph before the final reference is run. FU should be 400 on the reference, if it is not, this should be adjusted with, for example, the quantity of liquid. The reference/sample is removed with a spatula and placed in the hand (with a disposable glove on it), before it is filled into small glass tubes (of approx. 4.5 cm's length) that are put in NMR tubes and corked up. 7 tubes per dough are made.

When all the samples have been prepared, the tubes are placed in a (programmable) water bath at 33° C. (without corks) for 25 min. and hereafter the water bath is set to stay for 5 min. at 33° C., then to heated to 98° C. over 56 min. (1.1° C. per minute) and finally to stay for 5 min. at 96° C.

Figure 2:
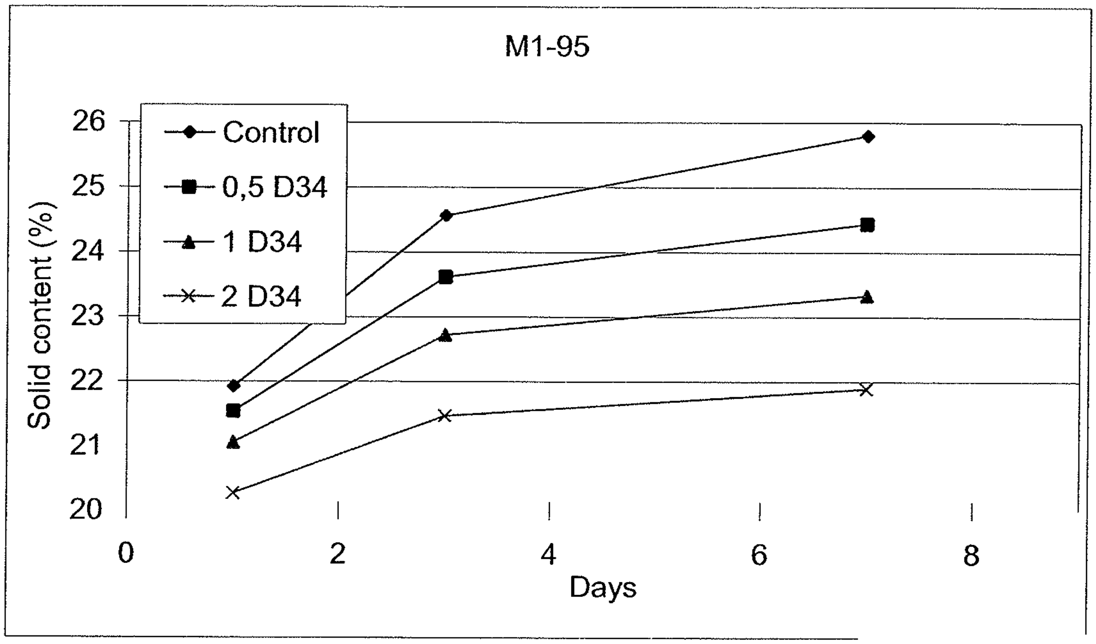
FIG. 2 is a graph showing dosage effect of PSac-D34 in a model baking system trial. Solid content of crumb was measured by NMR. The effect on retrogradation measured as solid content of the crumb is plotted against days after baking for control, 0.5, 1, 2 ppm of D34.

The tubes are stored at 20.0° C. in a thermo cupboard. The solid content of the crumb was measured by proton NMR using a Bruker NMS 120 Minispec NMR analyser at day 1, 3 and 7 as shown for crumb samples prepared with 0, 0.5, 1 and 2 ppm PSacD34 in FIG. 2. The lower increase in solid content over time represents the reduction in amylopectin retrogradation. After 7 days of storage at 20.0° C. in a thermo cupboard 10-20 mg samples of crumb weighed out and placed in 40 III aluminium standard DSC capsules and kept at 20° C.

The capsules are used for Differential Scanning Calorimetry on a Mettler Toledo DSC 820 instrument. As parameters are used a heating cycle of 20-95° C. with 10 C per min. heating and Gas/flow: $N_2$/80 ml per min. The results are analysed and the enthalpy for melting of retrograded amylopectin is calculated in J/g.

Example 10

Antistaling Effects

Model bread crumbs are prepared and measured according to Example 8. As shown in Table 2, PS4 variants show a strong reduction of the amylopectin retrogradation after baking as measured by Differential Scanning Calorimetry in comparison to the control. The PS4 variants shows a clear dosage effect.

Example 11

Firmness Effects in Baking Trials

Baking trials were carried out with a standard white bread sponge and dough recipe for US toast. The sponge dough is prepared from 1600 g of flour "All Purpose Classic" from Sisco Mills, USA", 950.g of water, 40 g of soy bean oil and 32 g of dry yeast. The sponge is mixed for 1 min. at low speed and subsequently 3 min. at speed 2 on a Hobart spiral mixer. The sponge is subsequently fermented for 2.5 hours at 35° C., 85% RH followed by 0.5 hour at 5° C.

Thereafter 400 g of flour, 4 g of dry yeast, 40 g of salt, 2.4 g of calcium propionate, 240 g of high fructose corn sirup (Isosweet), 5 g of the emulsifier PANODAN 205, 5 g of enzyme active soy flour, 30 g of non-active soy flour, 220 g of water and 30 g of a solution of ascorbic acid (prepared from 4 g ascorbic acid solubilised in 500 g of water) are added to the sponge. The resulting dough is mixed for 1 min. at low speed and then 6 min. on speed 2 on a Diosna mixer. Thereafter the dough is rested for 5 min. at ambient temperature, and then 550 g dough pieces are scaled, rested for 5 min. and then sheeted on Glimek sheeter with the settings 1:4, 2:4, 3:15, 4:12 and 10 on each side and transferred to a baking form. After 60 min. proofing at 43° C. at 90% RH the doughs are baked for 29 min. at 218° C.

Figure 3:
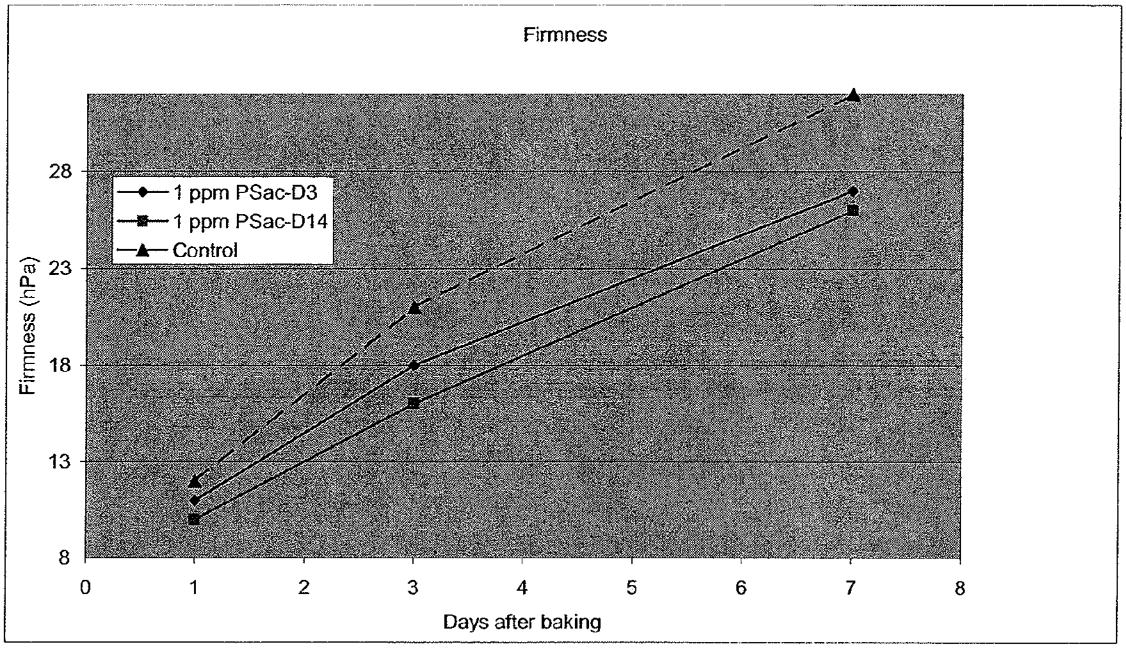
FIG. 3 is a graph showing the results of a baking trial showing reduced firmness and firming rate as upon adding PSac-D3a Psac-114 in a dosage of 1 mg per kg of flour. Firmness measured by hPa is plotted against days after baking for control.
Figure 4:
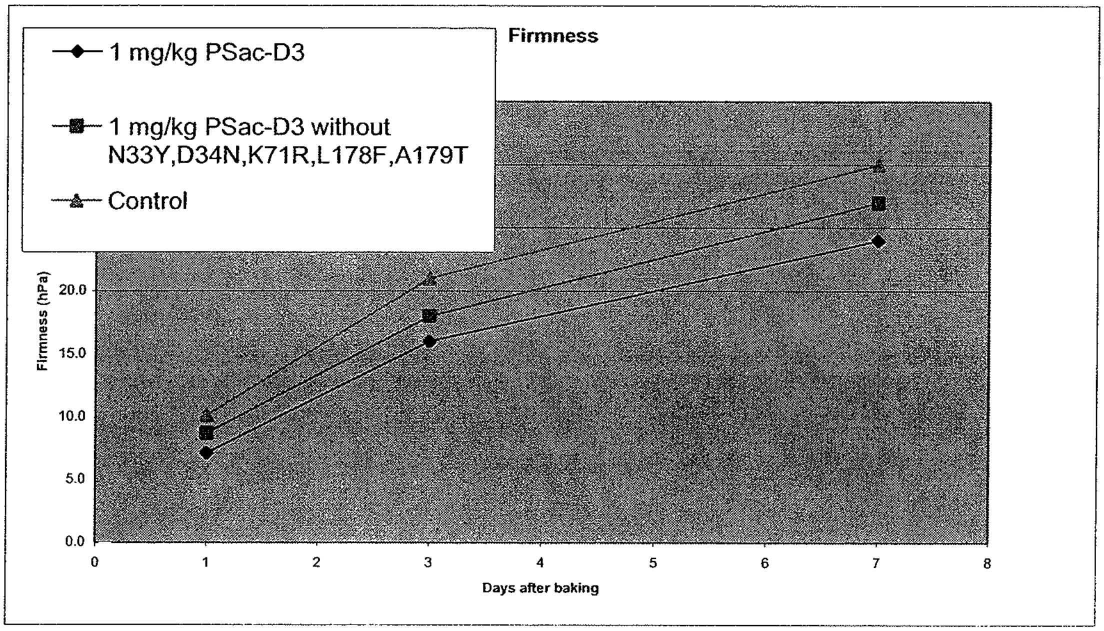
FIG. 4 shows a baking trial showing the increased softening effect of PSac-D3 (N33Y, D34N, K71R, G134R, A141P, 1157L, L178F, A179T, G223A, A307L, D343E, S334P) compared to PSac-D3 without N33Y, D34N, K71R, L178F, A179T, which has $t_{1/2}$–75 of 3.6 in contrast to that of PSac-D3 being 9.3 min at 75 C. Similar results are obtained with a variant of PSac-D3 lacking the mutations at N33Y, D34N.

Firmness and resilience were measured with a TA-XT 2 texture analyser. The Softness, cohesiveness and resilience is determined by analysing bread slices by Texture Profile Analysis using a Texture Analyser From Stable Micro Systems, UK. The following settings were used:

Pre Test Speed: 2 mm/s
Test Speed: 2 mm/s
Post Test Speed: 10 mm/s
Rupture Test Distance: 1%
Distance: 40%
Force: 0.098 N
Time: 5.00 sec
Count: 5
Load Cell: 5 kg
Trigger Type Auto—0.01 N
Results are shown in FIGS. 3 and 4.

Example 12

Control of Volume of Danish Rolls

Danish Rolls are prepared from a dough based on 2000 g Danish reform flour (from Cerealia), 120 g compressed yeast, 32 g salt, and 32 g sucrose. Water is added to the dough according to prior water optimisation.

The dough is mixed on a Diosna mixer (2 min. at low speed and 5 min. at high speed). The dough temperature after mixing is kept at 26° C. 1350 g dough is scaled and rested for 10 min. in a heating cabinet at 30 C. The rolls are moulded on a Fortuna molder and proofed for 45 min. at 34° C. and at 85% relative humidity. Subsequently the rolls are baked in a Bago 2 oven for 18 min. at 250° C. with steam in the first 13 seconds. After baking the rolls are cooled for 25 min. before weighing and measuring of volume.

The rolls are evaluated regarding crust appearance, crumb homogeneity, capping of the crust, ausbund and specific volume (measuring the volume with the rape seed displacement method).

Based on these criteria it is found that the PS4 variants increase the specific volume and improve the quality parameters of Danish rolls. Thus PS4 variants are able to control the volume of baked products.

Example 13

Chemically Leavened Vanilla Cake Donut

Vanilla cake donuts are prepared using a standard recipe as follows.

| Ingredients | Grams |
|---|---|
| Step 1 | |
| U.S. Soft wheat Flour (8.8-9.0% Protein) | 3600 |
| U.S. Hard Winter Wheat Flour (10.3-11.0%) | 2400 |
| Granulated Sugar | 2512 |
| Dried Egg Yolk | 200 |
| Defatted Soy Flour | 370 |
| Nonfat Dried Milk | 200 |
| Soda (USP #2) | 83 |
| Sodium Acid Pyrophosphate #40 | 83 |
| Sodium Acid Pyrophosphate #28 | 36 |
| Salt | 90 |
| Artificial Vanilla Flavor G28395 (DANISCO, New Century, Kansas) | 15 |
| Modified Food Starch (StabiTex Instant 12626, Cerestar, USA, Hammond, IN) | 30 |
| Cellulose Gum | 10 |
| DIMODAN ® PH300 K A Softener (DANISCO, New Century, Kansas) | 41 |
| Step 2 | |
| Soybean Oil | 300 |
| Fluid Lecithin | 30 |
| Total | 10,000 |

Mix Preparation Procedure

1. Use a Hobart A-200 mixer with a paddle and a 20-quart bowl. Combine Step 1 ingredients and blend for 10 minutes on Speed 1. 2. Add Step 2 ingredients over 2 minutes in Speed 1, then blend 18 additional minutes. 3. Run mix through cake finisher to smooth and remove lumps.

Batter Preparation Procedure

1. Use a Hobart A-200 mixer with a paddle and a 12-quart bowl. Mix: 2000 grams; Water: 900 grams. Add water to the bottom of the bowl. 2. Add mix on top. Mix 1 minute on Speed 1, them 2 minutes on Speed 2. 3. The target batter temperature should be 72° F. for donuts made in an open kettle fryer.

Frying Procedure

Set fryer temperature for 375° F. using well conditioned donut shortening to fry donuts (do not use oil or all-purpose shortening).

For an Open Kettle Fryer

Target a weight of 43 grams per donut using a 1¾ inch diameter cutter. Fry for 50 seconds on the first side, flip, then fry 50-60 seconds more. Remove from fryer and allow grease to drain and donuts to cool.

Example 14

Fresh keeping effects in Vanilla Cake Donut

Addition of PSac-D34 to Vanilla Cake Donuts (Example 13) improves the fresh keeping as evaluated on day 8 after baking:

TABLE 10

Freshness parameters evaluated in Donuts without and with PSac-D34

| | Hardness | Cohesiveness | Resilience | Freshness | Gumminess | Overall liking |
|---|---|---|---|---|---|---|
| Control | 330 | 0.581 | 0.272 | 5.04 | 4.19 | 4.54 |
| 2 mg/kg PSac-D34 | 240 | 0.646 | 0.295 | 5.53 | 5.46 | 5.15 |

Hardness, Cohesiveness and Resilience are measured on TPA as described in Example 11.

Freshness, Gumminess and Overall liking are scored by sensory evaluation on a scale from 1-9 where 1 is inferior and 9 is best.

It is observed that all quality parameters are improved due to addition of PSac-D34; hardness is reduced, cohesiveness and resilience are increased and freshness, gumminess and overall liking based on sensory evaluation are improved.

The invention will now be further described by the following numbered paragraphs:

1. A food additive comprising a PS4 variant polypeptide, in which the PS4 variant polypeptide is derivable from a parent polypeptide having non-maltogenic exoamylase activity, in which the PS4 variant polypeptide comprises substitutions at the following positions: G121D, 134, 141, 157, 223, 307 and 334 with reference to the position numbering of a *Pseudomonas saccharophilia* exoamylase sequence shown as SEQ ID NO: 1.
2. A food additive according to Paragraph 1, further comprising a further substitution at position 223, preferably G223A.
3. A food additive according to Paragraph 1 or Paragraph 2, further comprising one or more of: a substitution at position 33, preferably N33, more preferably N33Y, a substitution at position 34, preferably D34, more preferably D34N, a substitution at position 178 and a substitution at position 179.
4. A food additive according to Paragraph 1 or 2, in which the parent polypeptide comprises a non-maltogenic exoamylase, preferably a glucan 1,4-alpha-maltotetrahydrolase (EC 3.2.1.60), more preferably being derivable from *Pseudomonas* species, preferably *Pseudomonas saccharophilia* or *Pseudomonas stutzeri.*
5. A food additive according to any preceding paragraph, in which the parent polypeptide is a non-maltogenic exoamylase from *Pseudomonas saccharophilia* exoamylase having a sequence shown as SEQ ID NO: 1 or SEQ ID NO: 5.
6. A food additive according to any of Paragraphs 1 to 7, in which the parent polypeptide is a non-maltogenic exoamylase from *Pseudomonas stutzeri* having a sequence shown as SEQ ID NO: 7 or SEQ ID NO: 11.
7. A food additive according to any preceding paragraph, which has a higher thermostability compared to the parent polypeptide when tested under the same conditions.
8. A food additive according to any preceding paragraph, in which the half life ($t_{1/2}$), preferably at 60 degrees C., is increased by 15% or more, preferably 50% or more, most preferably 100% or more, relative to the parent polypeptide.
9. A food additive according to any preceding paragraph, which has a higher exo-specificity compared to the parent polypeptide when tested under the same conditions.
10. A food additive according to any preceding paragraph, which has 10% or more, preferably 20% or more, preferably 50% or more, exo-specificity compared to the parent polypeptide.
11. A food additive according to any preceding paragraph, in which the position 134 substitution comprises G134R.
12. A food additive according to any preceding paragraph, in which the position 141substitution comprises A141P.
13. A food additive to any preceding paragraph, in which the position 334 substitution comprises S334P.
14. A food additive according to any preceding paragraph, in which
    a. the position 33 substitution comprises N33Y;
    b. the position 34 substitution comprises D34N;
    c. the position 157 substitution comprises 1157L;
    d. the position 178 substitution comprises L178F;
    e. the position 179 substitution comprises A179T.
    f. the position 223 substitution comprises G223A; or
    g. the position 307 substitution comprises H307L.
15. A food additive according to any preceding paragraph, which comprises the substitutions: G134R, A141P, 1157L, G223A, H307L and S334P, together with phenylalanine at position 178 or threonine at position 179, or both, optionally together with N33Y and D34N.
16. A food additive according to any preceding paragraph, which has the sequence PSac-D34 (SEQ ID NO: 2) or the sequence PStu-D34 (SEQ ID NO: 8).
17. A food additive according to any preceding paragraph, which further comprises a substitution at position 121, preferably G121D.
18. A food additive according to Paragraph 17, which has the sequence PSac-D20 (SEQ ID NO: 3) or the sequence PStu-$D_2O$ (SEQ ID NO: 9).

19. A food additive according to any preceding paragraph, which further comprises a substitution at position 87, preferably G87S.
20. A food additive according to Paragraph 19, which has the sequence PSac-D14 (SEQ ID NO: 4).
21. A food additive according to Paragraph 19, which has the sequence PStu-D14 (SEQ ID NO: 10).
22. A food additive according to any preceding paragraph, which has the sequence PSac-pPD77d33.
23. Use of a PS4 variant polypeptide as set out in any preceding paragraph as a food additive.
24. A process for treating a starch comprising contacting the starch with a PS4 variant polypeptide as set out in any preceding paragraph and allowing the polypeptide to generate from the starch one or more linear products.
25. Use of a PS4 variant polypeptide as set out in any of Paragraphs 1 to 23 in preparing a food product.
26. A process of preparing a food product comprising admixing a polypeptide as set out in any of Paragraphs 1 to 23 with a food ingredient.
27. Use according to Paragraph 25, or a process according to Paragraph 26, in which the food product comprises a dough or a dough product, preferably a processed dough product.
28. A use or process according to any of Paragraphs 25 to 7, in which the food product is a bakery product.
29. A process for making a bakery product comprising: (a), providing a starch medium; (b) adding to the starch medium a PS4 variant polypeptide as set out in any of Paragraphs 1 to 23; and (c) applying heat to the starch-medium during or after step (b) to produce a bakery product.
30. A food product, dough product or a bakery product obtained by a process according to any of Paragraphs 25 to 29.
31. A improver composition for a dough, in which the improver composition comprises a PS4 variant polypeptide as set out in any of Paragraphs 1 to 23, and at least one further dough ingredient or dough additive.

32. A composition comprising a flour and a PS4 variant polypeptide as set out in any of Paragraphs 1 to 23.

33. Use of a PS4 variant polypeptide as set out in any of Paragraphs 1 to 23, in a dough product to retard or reduce staling, preferably detrimental retrogradation, of the dough product.

34. A combination of a PS4 variant polypeptide as set out in any preceding paragraph, together with Novamyl, or a variant, homologue, or mutants thereof which has maltogenic alpha-amylase activity.
35. Use of a combination according to Paragraph 34 for an application according to any preceding paragraph.
36. A food product produced by treatment with a combination according to Paragraph 34.

REFERENCES

Penninga, D., van der Veen, B. A., Knegtel, R. M., van Hijum, S. A., Rozeboom, H. J., Kalk, K. H., Dijkstra, B. W., Dijkhuizen, L. (1996). The raw starch binding domain of cyclodextrin glycosyltransferase from *Bacillus circulans* strain 251. J. Biol. Chem. 271, 32777-32784.

Sambrook J, F.E.M.T. (1989). Molecular Cloning: A Laboratory Manual, 2nd Edn. Cold Spring Harbor Laboratory, Cold Spring Harbor N.Y.

Zhou, J. H., Baba, T., Takano, T., Kobayashi, S., Arai, Y. (1989). Nucleotide sequence of the maltotetraohydrolase gene from *Pseudomonas saccharophila*. FEBS Lett. 255, 37-41.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A food additive comprising a polypeptide having non-maltogenic exoamylase activity and having at least 95% identity with SEQ ID NO:1, wherein the polypeptide comprises an amino acid sequence having substitutions at positions corresponding to positions 134, 141, 157, 223, 307 and 334 of SEQ ID NO: 1.

2. The food additive according to claim 1, wherein the substitution at a position corresponding to position 223 of SEQ ID NO: 1 is G223A.

3. The food additive according to claim 1, wherein the polypeptide comprises an amino acid sequence further comprising one or more of: a substitution at a position corresponding to position 33 of SEQ ID NO: 1, a substitution at a position corresponding to position 34 of SEQ ID NO: 1, a substitution at a position corresponding to position 178 of SEQ ID NO: 11 and a substitution at a position corresponding to position 179 of SEQ ID NO: 1.

4. The food additive according to claim 1, wherein the polypeptide is a glucan 1,4-alpha-maltotetrahydrolase (EC 3.2.1.60), obtained from *Pseudomonas* species.

5. The food additive according to claim 1, wherein the polypeptide is a non-maltogenic exoamylase obtained by modifying the *Pseudomonas saccharophila* non-maltogenic exoamylase of SEQ ID NO: 1 or SEQ ID NO: 5.

6. The food additive according to claim 1, wherein the polypeptide has a higher thermostability compared to the polypeptide of SEQ ID NO: 1 when tested under the same conditions.

7. The food additive according to claim 1, wherein the polypeptide has a half life at 60° C. increased by 15% or more relative to half life at 60° C. of the polypeptide of SEQ ID NO: 1.

8. The food additive according to claim 1, wherein the polypeptide has a higher exo-specificity compared to the exo-specificity of the polypeptide of SEQ ID NO: 1 when tested under the same conditions.

9. The food additive according to claim 1, wherein the polypeptide has 10% or more, exo-specificity compared to the polypeptide of SEQ ID NO: 1.

10. The food additive according to claim 1, wherein the substitution at a position corresponding to position 134 of SEQ ID NO: 1 comprises G134R.

11. The food additive according to claim 1, wherein substitution at a position corresponding to position 141 of the of SEQ ID NO: 1 comprises A141 P.

12. The food additive according to claim 1, in which the substitution at a position corresponding to position 334 of SEQ ID NO: 1 comprises S334P.

13. The food additive according to claim 3, in which (a) the substitution at a position corresponding to position 33 of SEQ ID NO: 1 comprises N33Y; (b) the substitution at a position corresponding to position 34 of SEQ ID NO: 1 comprises D34N; (c) the substitution at a position corresponding to position 157 of SEQ ID NO: 1 comprises I157L; (d) the substitution at a position corresponding to position 178 of SEQ ID NO: 1 comprises L178F; (e) the substitution at a position corresponding to position 179 of SEQ ID NO: 1 comprises Al 79T; (f) the substitution at a position corresponding to position 223 of SEQ ID NO: 1 comprises G223A; or (g) the substitution at a position corresponding to position 307 of SEQ ID NO: 1 comprises H307L.

14. The food additive according to claim 3, wherein the polypeptide comprises one of the following combinations of substitutions at positions corresponding to positions of SEQ ID NO: 1 selected from the group consisting of:

(a) G134R, A141P, I157L, G223A, H307L, S334P, and 178F;

(b) G134R, A141P, I157L, G223A, H307L, S334P, and 179T;

(c) G134R, A141P, I157L, G223A, H307L, S334P, 178F, and 179T; and (d) G134R, A141P, I157L, G223A, H307L, S334P, 178F, 179T, N33Y, and D34N.

15. The food additive according to claim 1, which has the sequence of SEQ ID NO: 2 (PSac-D34).

16. The food additive according to claim 1, wherein the polypeptide further comprises a substitution at position corresponding to position 121 of SEQ ID NO: 1.

17. The food additive according to claim 16, which has the sequence of SEQ ID NO: 3 (PSac-D20).

18. The food additive according to claim 1, which further comprises a substitution at a position corresponding to position 87 of SEQ ID NO: 1.

19. The food additive according to claim 18, which has the sequence of SEQ ID NO: 4 (PSac-D14).

20. A process for treating a starch comprising contacting the starch with the food additive of claim 1 and allowing the polypeptide to generate from the starch one or more linear products.

21. A process of preparing a food product comprising mixing the food additive of claim 1 with a food ingredient.

22. The process of claim 21, in which the food product comprises a dough or a dough product, or a processed dough product.

23. The process of claim 21, in which the food product is a bakery product.

24. A process for making a bakery product comprising: (a) providing a starch medium; (b) adding to the starch medium the food additive of claim 1; and (c) applying heat to the starch medium during or after step (b) to produce a bakery product.

25. An improved dough composition, wherein the composition comprises the food additive of claim 1, and at least one further dough ingredient or dough additive.

26. A composition comprising a flour and the food additive of claim 1.

27. A composition comprising food additive of claim 1, together with a maltogenic alpha-amylase.

* * * * *

SEQUENCE LISTING

```
<160> NUMBER OF SEQ ID NOS: 72

<210> SEQ ID NO 1
<211> LENGTH: 530
<212> TYPE: PRT
<213> ORGANISM: Pseudomonas saccharophila

<400> SEQUENCE: 1

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60
```

```
Ser Trp Thr Asp Gly Gly Lys Ser Gly Gly Gly Glu Gly Tyr Phe Trp
 65                 70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
```

```
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Ala Gly Ala Ser Thr Ser Gly
        515                 520                 525

Ser Phe
    530


<210> SEQ ID NO 2
<211> LENGTH: 429
<212> TYPE: PRT
<213> ORGANISM: Pseudomonas saccharophila

<400> SEQUENCE: 2

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Pro Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
```

-continued

```
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 3
<211> LENGTH: 429
<212> TYPE: PRT
<213> ORGANISM: Pseudomonas saccharophila

<400> SEQUENCE: 3

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Pro Gly Arg Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
```

```
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 4
<211> LENGTH: 429
<212> TYPE: PRT
<213> ORGANISM: Pseudomonas saccharophila

<400> SEQUENCE: 4

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
     50                  55                  60

Ser Trp Thr Asp Pro Gly Arg Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
```

```
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 5
<211> LENGTH: 551
<212> TYPE: PRT
<213> ORGANISM: Pseudomonas saccharophila

<400> SEQUENCE: 5

Met Ser His Ile Leu Arg Ala Ala Val Leu Ala Ala Val Leu Leu Pro
  1               5                  10                  15

Phe Pro Ala Leu Ala Asp Gln Ala Gly Lys Ser Pro Ala Gly Val Arg
             20                  25                  30

Tyr His Gly Gly Asp Glu Ile Ile Leu Gln Gly Phe His Trp Asn Val
         35                  40                  45

Val Arg Glu Ala Pro Asn Asp Trp Tyr Asn Ile Leu Arg Gln Gln Ala
     50                  55                  60

Ser Thr Ile Ala Ala Asp Gly Phe Ser Ala Ile Trp Met Pro Val Pro
 65                  70                  75                  80

Trp Arg Asp Phe Ser Ser Trp Thr Asp Gly Gly Lys Ser Gly Gly Gly
                 85                  90                  95

Glu Gly Tyr Phe Trp His Asp Phe Asn Lys Asn Gly Arg Tyr Gly Ser
            100                 105                 110

Asp Ala Gln Leu Arg Gln Ala Ala Gly Ala Leu Gly Gly Ala Gly Val
        115                 120                 125

Lys Val Leu Tyr Asp Val Val Pro Asn His Met Asn Arg Gly Tyr Pro
    130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Asp Gly Asp Arg
                165                 170                 175

Phe Ile Gly Gly Glu Ser Asp Leu Asn Thr Gly His Pro Gln Ile Tyr
```

-continued

```
            180                 185                 190

Gly Met Phe Arg Asp Glu Leu Ala Asn Leu Arg Ser Gly Tyr Gly Ala
        195                 200                 205

Gly Gly Phe Arg Phe Asp Phe Val Arg Gly Tyr Ala Pro Glu Arg Val
    210                 215                 220

Asp Ser Trp Met Ser Asp Ser Ala Asp Ser Ser Phe Cys Val Gly Glu
225                 230                 235                 240

Leu Trp Lys Gly Pro Ser Glu Tyr Pro Ser Trp Asp Trp Arg Asn Thr
                245                 250                 255

Ala Ser Trp Gln Gln Ile Ile Lys Asp Trp Ser Asp Arg Ala Lys Cys
            260                 265                 270

Pro Val Phe Asp Phe Ala Leu Lys Glu Arg Met Gln Asn Gly Ser Val
        275                 280                 285

Ala Asp Trp Lys His Gly Leu Asn Gly Asn Pro Asp Pro Arg Trp Arg
    290                 295                 300

Glu Val Ala Val Thr Phe Val Asp Asn His Asp Thr Gly Tyr Ser Pro
305                 310                 315                 320

Gly Gln Asn Gly Gly Gln His His Trp Ala Leu Gln Asp Gly Leu Ile
                325                 330                 335

Arg Gln Ala Tyr Ala Tyr Ile Leu Thr Ser Pro Gly Thr Pro Val Val
            340                 345                 350

Tyr Trp Ser His Met Tyr Asp Trp Gly Tyr Gly Asp Phe Ile Arg Gln
        355                 360                 365

Leu Ile Gln Val Arg Arg Thr Ala Gly Val Arg Ala Asp Ser Ala Ile
    370                 375                 380

Ser Phe His Ser Gly Tyr Ser Gly Leu Val Ala Thr Val Ser Gly Ser
385                 390                 395                 400

Gln Gln Thr Leu Val Val Ala Leu Asn Ser Asp Leu Ala Asn Pro Gly
                405                 410                 415

Gln Val Ala Ser Gly Ser Phe Ser Glu Ala Val Asn Ala Ser Asn Gly
            420                 425                 430

Gln Val Arg Val Trp Arg Ser Gly Ser Gly Asp Gly Gly Gly Asn Asp
        435                 440                 445

Gly Gly Glu Gly Gly Leu Val Asn Val Asn Phe Arg Cys Asp Asn Gly
    450                 455                 460

Val Thr Gln Met Gly Asp Ser Val Tyr Ala Val Gly Asn Val Ser Gln
465                 470                 475                 480

Leu Gly Asn Trp Ser Pro Ala Ser Ala Val Arg Leu Thr Asp Thr Ser
                485                 490                 495

Ser Tyr Pro Thr Trp Lys Gly Ser Ile Ala Leu Pro Asp Gly Gln Asn
            500                 505                 510

Val Glu Trp Lys Cys Leu Ile Arg Asn Glu Ala Asp Ala Thr Leu Val
        515                 520                 525

Arg Gln Trp Gln Ser Gly Gly Asn Asn Gln Val Gln Ala Ala Ala Gly
    530                 535                 540

Ala Ser Thr Ser Gly Ser Phe
545                 550
```

<210> SEQ ID NO 6
<211> LENGTH: 3050
<212> TYPE: DNA
<213> ORGANISM: Pseudomonas saccharophila

<400> SEQUENCE: 6
gatcggcgta ggtttcgcat tcgttgccca ggcgatattt cgccggtgcg ccagcagcct 60

-continued

```
ggaagcaggc ctggtcgccg ccgccggccg tggcgccgac gcccgaacgc agatagccgt    120
ggaaatcgac cgccagggcc gggccgccga ccagcagggc ggcaagcagg caggcgggtt    180
ttaggacgaa cagggggtgc gcggtgtgct tcatgacgag gtccttgttt ttcttgttaa    240
tgccgaatcg atcacgcctt cgctgcgtgt cgcagggcgc agctcggtgg cgaaagcctc    300
ggggatggct ccgctggcgg catcctcccg accagagatt tcgctggcgc agctcgaggg    360
cgtaatcagg atgagtgcgg cgtaatccct ggggtggggc tacgcccggc agggcgcaga    420
tgattgccag gggccttcgg cctggccact acgccgcctg caactgggcg ggggaggttg    480
gtggtcgggg cgtgcagggg cagcctgcgg gtgccggtcg aagacccggc cggcgttcat    540
cctcgtccgg cggccttgcc gtaggatacc cgaacaagca caagaaccgg agtattgcga    600
tgagccacat cctgcgtgcc gccgtattgg cggcggtcct gctgccgttt cccgcactgg    660
ccgatcaggc cggcaagagc ccggccgggg tgcgctacca cggcggcgac gaaatcatcc    720
tccagggctt ccactggaac gtcgtccgcg aagcgcccaa cgactggtac aacatcctcc    780
gccaacaggc ctcgacgatc gcggccgacg gcttctcggc aatctggatg ccggtgccct    840
ggcgtgactt ctccagctgg accgacggcg gcaagtccgg cggcggcgaa ggctacttct    900
ggcacgactt caacaagaac ggccgctacg gcagcgacgc ccagctgcgc caggccgccg    960
gcgcactcgg tggcgccggg gtgaaggtgc tctacgatgt ggtgcccaat cacatgaacc   1020
gcggctaccc ggacaaggag atcaacctgc cggccggcca gggcttctgg cgcaacgact   1080
gcgccgaccc gggcaactac cccaacgact gcgacgacgg tgaccgcttc atcggcggcg   1140
agtcggacct gaacaccggc catccgcaga tttacggcat gtttcgcgac gagcttgcca   1200
acctgcgcag cggctacggc gccggcggct tccgcttcga cttcgttcgc ggctatgcgc   1260
ccgagcgggt cgacagctgg atgagcgaca gcgccgacag cagcttctgc gttggcgagc   1320
tgtggaaagg cccttctgaa tatccgagct gggactggcg caacacggcg agctggcagc   1380
agatcatcaa ggactggtcc gaccgggcca agtgcccggt gttcgacttc gctctcaagg   1440
agcgcatgca gaacggctcg gtcgccgact ggaagcatgg cctcaatggc aaccccgacc   1500
cgcgctggcg cgaggtggcg gtgaccttcg tcgacaacca cgacaccggc tattcgcccg   1560
ggcagaacgg cggccagcac cactgggcgc tgcaggacgg gctgatccgc caggcctacg   1620
cctacatcct caccagcccg ggcacgccgg tggtgtactg gtcgcacatg tacgactggg   1680
gctacggcga cttcatccgc cagctgatcc aggtgcggcg caccgccggc gtgcgcgccg   1740
attcggcgat cagcttccat agcggctaca gcggtctggt cgctaccgtc agcggcagcc   1800
agcagaccct ggtggtggcg ctcaactccg atctggccaa ccccggccag gttgccagcg   1860
gcagcttcag cgaggcggtc aacgccagca acggccaggt gcgcgtctgg cgcagcggta   1920
gcggcgatgg cggcgggaat gacggcggcg agggtggctt ggtcaatgtg aactttcgct   1980
gcgacaacgg cgtgacgcag atgggcgaca gcgtctacgc ggtgggcaac gtcagccagc   2040
tcggcaactg gagcccggcc tccgcggtac ggctgaccga caccagcagc tatccgacct   2100
ggaagggcag catcgccctg cctgacggtc agaacgtgga atggaagtgc ctgatccgca   2160
acgaggcgga cgcgacgctg gtgcgtcagt ggcaatcggg cggcaacaac caggtccagg   2220
ccgccgccgg cgcgagcacc agcggctcgt tctgacgaca tgcccgcccg gcctcggcta   2280
cgcctacgcc gggcggctcc tcccgaccca gggtgggcag ggaggaggcc ggcgacgggc   2340
cgggccgccg atgctggcac gacaaccata aaagccttcg cgctgcgctg tcgtatcagg   2400
agctgttcat gttggcccag acccgctcga cccctttccg gcttggcttc ctggcccggc   2460
```

-continued

```
tgtacctgct gatcgccgca ctggtggcct tgctgatgct ggtagccggc accagcctgg   2520

ttgccatcgg ccgcctgcaa ggcaatgccg agcaaatctc gtcgaccgcg tcgcgtctgc   2580

tggtcagcga gagcttcttc ggtacgttgc agagcctgac gcagaacctg tccgacgccc   2640

tggccgagga ccggcctgac cagctcgacg gctatgtcgg ccggcatcgc acgctgcagg   2700

accaggccct cgagctgttc gcccagctgg agcgggtgac gccggcacat gccgagacca   2760

agcaagcctg gcggcgctgt tgccggagct cgaccgccgc agcctggcgc tgatcgatgc   2820

gcacgcgacc tgctcgcgcg tggggcgcaa cgccgtcgcc tgcgcgatct gcagctgcag   2880

ttctcgcggc tcaagcagga cctgctgcag gcgcagttcg tgacgggcga cgagctggtc   2940

gcctattcca tcaagcagtt catcatcccg ctcgagcagg tcgagcgctg ctgttcgatg   3000

ccatcggcgt gtcttcgatc aaggcactcg atgaagcggg tgcgcagatc              3050
```

```
<210> SEQ ID NO 7
<211> LENGTH: 527
<212> TYPE: PRT
<213> ORGANISM: Pseudomonas stutzeri

<400> SEQUENCE: 7

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Gly Ser Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Gly Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270
```

```
Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 8
<211> LENGTH: 527
<212> TYPE: PRT
<213> ORGANISM: Pseudomonas stutzeri

<400> SEQUENCE: 8

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Pro Ser Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125
```

-continued

```
Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525
```

<210> SEQ ID NO 9
<211> LENGTH: 527
<212> TYPE: PRT
<213> ORGANISM: Pseudomonas stutzeri

<400> SEQUENCE: 9

Asp Gln Ala Gly Lys Ser Pro Asn Ala Val Arg Tyr His Gly Gly Asp
1 5 10 15

Glu Ile Ile Leu Gln Gly Phe His Trp Asn Val Val Arg Glu Ala Pro
20 25 30

Tyr Asn Trp Tyr Asn Ile Leu Arg Gln Gln Ala Ala Thr Ile Ala Ala
35 40 45

Asp Gly Phe Ser Ala Ile Trp Met Pro Val Pro Trp Arg Asp Phe Ser
50 55 60

Ser Trp Ser Asp Pro Ser Arg Ser Gly Gly Gly Glu Gly Tyr Phe Trp
65 70 75 80

His Asp Phe Asn Lys Asn Gly Arg Tyr Gly Ser Asp Ala Gln Leu Arg
85 90 95

Gln Ala Ala Ser Ala Leu Gly Gly Ala Gly Val Lys Val Leu Tyr Asp
100 105 110

Val Val Pro Asn His Met Asn Arg Asp Tyr Pro Asp Lys Glu Ile Asn
115 120 125

Leu Pro Ala Gly Gln Arg Phe Trp Arg Asn Asp Cys Pro Asp Pro Gly
130 135 140

Asn Tyr Pro Asn Asp Cys Asp Asp Gly Asp Arg Phe Leu Gly Gly Asp
145 150 155 160

Ala Asp Leu Asn Thr Gly His Pro Gln Val Tyr Gly Met Phe Arg Asp
165 170 175

Glu Phe Thr Asn Leu Arg Ser Gln Tyr Gly Ala Gly Gly Phe Arg Phe
180 185 190

Asp Phe Val Arg Gly Tyr Ala Pro Glu Arg Val Asn Ser Trp Met Thr
195 200 205

Asp Ser Ala Asp Asn Ser Phe Cys Val Gly Glu Leu Trp Lys Ala Pro
210 215 220

Ser Glu Tyr Pro Asn Trp Asp Trp Arg Asn Thr Ala Ser Trp Gln Gln
225 230 235 240

Ile Ile Lys Asp Trp Ser Asp Arg Ala Lys Cys Pro Val Phe Asp Phe
245 250 255

Ala Leu Lys Glu Arg Met Gln Asn Gly Ser Ile Ala Asp Trp Lys His
260 265 270

Gly Leu Asn Gly Asn Pro Asp Pro Arg Trp Arg Glu Val Ala Val Thr
275 280 285

Phe Val Asp Asn His Asp Thr Gly Tyr Ser Pro Gly Gln Asn Gly Gly
290 295 300

Gln His Leu Trp Ala Leu Gln Asp Gly Leu Ile Arg Gln Ala Tyr Ala
305 310 315 320

Tyr Ile Leu Thr Ser Pro Gly Thr Pro Val Val Tyr Trp Pro His Met
325 330 335

Tyr Asp Trp Gly Tyr Gly Glu Phe Ile Arg Gln Leu Ile Gln Val Arg
340 345 350

Arg Ala Ala Gly Val Arg Ala Asp Ser Ala Ile Ser Phe His Ser Gly
355 360 365

Tyr Ser Gly Leu Val Ala Thr Val Ser Gly Ser Gln Gln Thr Leu Val
370 375 380

Val Ala Leu Asn Ser Asp Leu Gly Asn Pro Gly Gln Val Ala Ser Gly
385 390 395 400

Ser Phe Ser Glu Ala Val Asn Ala Ser Asn Gly Gln Val Arg Val Trp
405 410 415

```
Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 10
<211> LENGTH: 527
<212> TYPE: PRT
<213> ORGANISM: Pseudomonas stutzeri

<400> SEQUENCE: 10

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Pro Ser Arg Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270
```

```
Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 11
<211> LENGTH: 548
<212> TYPE: PRT
<213> ORGANISM: Pseudomonas stutzeri

<400> SEQUENCE: 11

Met Ser His Ile Leu Arg Ala Ala Val Leu Ala Ala Met Leu Leu Pro
  1               5                  10                  15

Leu Pro Ser Met Ala Asp Gln Ala Gly Lys Ser Pro Asn Ala Val Arg
             20                  25                  30

Tyr His Gly Gly Asp Glu Ile Ile Leu Gln Gly Phe His Trp Asn Val
         35                  40                  45

Val Arg Glu Ala Pro Asn Asp Trp Tyr Asn Ile Leu Arg Gln Gln Ala
     50                  55                  60

Ala Thr Ile Ala Ala Asp Gly Phe Ser Ala Ile Trp Met Pro Val Pro
 65                  70                  75                  80

Trp Arg Asp Phe Ser Ser Trp Ser Asp Gly Ser Lys Ser Gly Gly Gly
                 85                  90                  95

Glu Gly Tyr Phe Trp His Asp Phe Asn Lys Asn Gly Arg Tyr Gly Ser
            100                 105                 110

Asp Ala Gln Leu Arg Gln Ala Ala Ser Ala Leu Gly Gly Ala Gly Val
        115                 120                 125
```

```
Lys Val Leu Tyr Asp Val Val Pro Asn His Met Asn Arg Gly Tyr Pro
    130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Asp Gly Asp Arg
                165                 170                 175

Phe Ile Gly Gly Asp Ala Asp Leu Asn Thr Gly His Pro Gln Val Tyr
            180                 185                 190

Gly Met Phe Arg Asp Glu Phe Thr Asn Leu Arg Ser Gln Tyr Gly Ala
        195                 200                 205

Gly Gly Phe Arg Phe Asp Phe Val Arg Gly Tyr Ala Pro Glu Arg Val
    210                 215                 220

Asn Ser Trp Met Thr Asp Ser Ala Asp Asn Ser Phe Cys Val Gly Glu
225                 230                 235                 240

Leu Trp Lys Gly Pro Ser Glu Tyr Pro Asn Trp Asp Trp Arg Asn Thr
                245                 250                 255

Ala Ser Trp Gln Gln Ile Ile Lys Asp Trp Ser Asp Arg Ala Lys Cys
            260                 265                 270

Pro Val Phe Asp Phe Ala Leu Lys Glu Arg Met Gln Asn Gly Ser Ile
        275                 280                 285

Ala Asp Trp Lys His Gly Leu Asn Gly Asn Pro Asp Pro Arg Trp Arg
    290                 295                 300

Glu Val Ala Val Thr Phe Val Asp Asn His Asp Thr Gly Tyr Ser Pro
305                 310                 315                 320

Gly Gln Asn Gly Gly Gln His His Trp Ala Leu Gln Asp Gly Leu Ile
                325                 330                 335

Arg Gln Ala Tyr Ala Tyr Ile Leu Thr Ser Pro Gly Thr Pro Val Val
            340                 345                 350

Tyr Trp Ser His Met Tyr Asp Trp Gly Tyr Gly Asp Phe Ile Arg Gln
        355                 360                 365

Leu Ile Gln Val Arg Arg Ala Ala Gly Val Arg Ala Asp Ser Ala Ile
    370                 375                 380

Ser Phe His Ser Gly Tyr Ser Gly Leu Val Ala Thr Val Ser Gly Ser
385                 390                 395                 400

Gln Gln Thr Leu Val Val Ala Leu Asn Ser Asp Leu Gly Asn Pro Gly
                405                 410                 415

Gln Val Ala Ser Gly Ser Phe Ser Glu Ala Val Asn Ala Ser Asn Gly
            420                 425                 430

Gln Val Arg Val Trp Arg Ser Gly Thr Gly Ser Gly Gly Gly Glu Pro
        435                 440                 445

Gly Ala Leu Val Ser Val Ser Phe Arg Cys Asp Asn Gly Ala Thr Gln
    450                 455                 460

Met Gly Asp Ser Val Tyr Ala Val Gly Asn Val Ser Gln Leu Gly Asn
465                 470                 475                 480

Trp Ser Pro Ala Ala Ala Leu Arg Leu Thr Asp Thr Ser Gly Tyr Pro
                485                 490                 495

Thr Trp Lys Gly Ser Ile Ala Leu Pro Ala Gly Gln Asn Glu Glu Trp
            500                 505                 510

Lys Cys Leu Ile Arg Asn Glu Ala Asn Ala Thr Gln Val Arg Gln Trp
        515                 520                 525

Gln Gly Gly Ala Asn Asn Ser Leu Thr Pro Ser Glu Gly Ala Thr Thr
    530                 535                 540

Val Gly Arg Leu
```

-continued

545

<210> SEQ ID NO 12
<211> LENGTH: 2082
<212> TYPE: DNA
<213> ORGANISM: Pseudomonas stutzeri

<400> SEQUENCE: 12
gatcggcctt tacggaaagt gatagagctt ctcttccggc aaactttgtt ccccagtgac 60
agagggttag tatcggatcg cttcctcttt gggtttggta gatcaggagc gccgagagca 120
ggatgaaatc ctgcggccag aaggtcgcgc cgaagatgtg gaactgctgc tggccgagat 180
ccggccggcg ttcatcctcg tccggcggcc ttgccgccag ctacccgaac aagcacaaga 240
accggagtat tgcgatgagc cacatcctgc gagccgccgt attggcggcg atgctgttgc 300
cgttgccgtc catggccgat caggccggca agagccccaa cgctgtgcgc taccacggcg 360
gcgacgaaat cattctccag ggctttcact ggaacgtcgt ccgcgaagcg cccaacgact 420
ggtacaacat cctgcgccag caggccgcga ccatcgccgc cgacggcttc tcggcgatct 480
ggatgccggt gccctggcgc gacttctcca gctggagcga cggcagcaag tccggcggcg 540
gtgaaggcta cttctggcac gacttcaaca agaacggccg ctatggcagt gacgcccagc 600
tgcgtcaggc cgccagcgcg ctcggtggcg ccggcgtgaa agtgctttac gacgtggtgc 660
ccaaccacat gaaccgtggc tatccggaca aggagatcaa cctcccggcc ggccagggct 720
tctggcgcaa cgactgcgcc gacccgggca actaccccaa tgattgcgac gacggcgacc 780
gcttcatcgg cggcgatgcg gacctcaaca ccggccaccc gcaggtctac ggcatgttcc 840
gcgatgaatt caccaacctg cgcagtcagt acggtgccgg cggcttccgc ttcgactttg 900
ttcggggcta tgcgccggag cggtcaaca gctggatgac cgatagcgcc gacaacagct 960
tctgcgtcgg cgaactgtgg aaaggcccct ctgagtaccc gaactgggac tggcgcaaca 1020
ccgccagctg gcagcagatc atcaaggact ggtccgaccg ggccaagtgc ccggtgttcg 1080
acttcgccct caaggaacgc atgcagaacg ctcgatcgcc gactggaagc acgcctgaac 1140
ggcaatcccg acccgcgtgg cgcgaggtgg cggtgacctt cgtcgacaac cacgacaccg 1200
gctactcgcc cgggcagaac ggtgggcagc accactgggc tctgcaggac gggctgatcc 1260
gccaggccta cgcctacatc ctcaccagcc ccggtacgcc ggtggtgtac tggtcgcaca 1320
tgtacgactg gggttacggc gacttcatcc gtcagctgat ccaggtgcgt cgcgccgccg 1380
gcgtgcgcgc cgattcggcg atcagcttcc acagcggcta cagcggtctg gtcgccaccg 1440
tcagcggcag ccagcagacc ctggtggtgg cgctcaactc cgacctgggc aatcccggcc 1500
aggtggccag cggcagcttc agcgaggcgg tcaacgccag caacggccag gtgcgcgtgt 1560
ggcgtagcgg cacgggcagc ggtggcggtg aacccggcgc tctggtcagt gtgagtttcc 1620
gctgcgacaa cggcgcgacg cagatgggcg acagcgtcta cgcggtcggc aacgtcagcc 1680
agctcggtaa ctggagcccg gccgcggcgt tgcgcctgac cgacaccagc ggctacccga 1740
cctggaaggg cagcattgcc ttgcctgccg gccagaacga ggaatggaaa tgcctgatcc 1800
gcaacgaggc caacgccacc caggtgcggc aatggcaggg cggggcaaac aacagcctga 1860
cgccgagcga gggcgccacc accgtcggcc ggctctagcc cgggcggcaa ctcggccgtc 1920
tcgcggatgt gaggcggctg gtctcggcgg cggtatcgtt gcgctggggg cggggccgcc 1980
gttcacgcgc cctgctatcg ctagttttcg gcgctccgcg catcggccag ttgccagcga 2040
atcgcctgcg cttcggcctg gtgcaggtcg tcgagcagcg ct 2082

<210> SEQ ID NO 13
<211> LENGTH: 429
<212> TYPE: PRT
<213> ORGANISM: Pseudomonas saccharophila

<400> SEQUENCE: 13

Asp Gln Ala Gly Lys Ser Pro Ala Gly Val Arg Tyr His Gly Gly Asp
1 5 10 15

Glu Ile Ile Leu Gln Gly Phe His Trp Asn Val Val Arg Glu Ala Pro
20 25 30

Tyr Asn Trp Tyr Asn Ile Leu Arg Gln Gln Ala Ser Thr Ile Ala Ala
35 40 45

Asp Gly Phe Ser Ala Ile Trp Met Pro Val Pro Trp Arg Asp Phe Ser
50 55 60

Ser Trp Thr Asp Gly Gly Lys Ser Gly Gly Gly Glu Gly Tyr Phe Trp
65 70 75 80

His Asp Phe Asn Lys Asn Gly Arg Tyr Gly Ser Asp Ala Gln Leu Arg
85 90 95

Gln Ala Ala Gly Ala Leu Gly Gly Ala Gly Val Lys Val Leu Tyr Asp
100 105 110

Val Val Pro Asn His Met Asn Arg Gly Tyr Pro Asp Lys Glu Ile Asn
115 120 125

Leu Pro Ala Gly Gln Arg Phe Trp Arg Asn Asp Cys Pro Asp Pro Gly
130 135 140

Asn Tyr Pro Asn Asp Cys Asp Asp Gly Asp Arg Phe Leu Gly Gly Glu
145 150 155 160

Ser Asp Leu Asn Thr Gly His Pro Gln Ile Tyr Gly Met Phe Arg Asp
165 170 175

Glu Phe Thr Asn Leu Arg Ser Gly Tyr Gly Ala Gly Gly Phe Arg Phe
180 185 190

Asp Phe Val Arg Gly Tyr Ala Pro Glu Arg Val Asp Ser Trp Met Ser
195 200 205

Asp Ser Ala Asp Ser Ser Phe Cys Val Gly Glu Leu Trp Lys Ala Pro
210 215 220

Ser Glu Tyr Pro Ser Trp Asp Trp Arg Asn Thr Ala Ser Trp Gln Gln
225 230 235 240

Ile Ile Lys Asp Trp Ser Asp Arg Ala Lys Cys Pro Val Phe Asp Phe
245 250 255

Ala Leu Lys Glu Arg Met Gln Asn Gly Ser Val Ala Asp Trp Lys His
260 265 270

Gly Leu Asn Gly Asn Pro Asp Pro Arg Trp Arg Glu Val Ala Val Thr
275 280 285

Phe Val Asp Asn His Asp Thr Gly Tyr Ser Pro Gly Gln Asn Gly Gly
290 295 300

Gln His Leu Trp Ala Leu Gln Asp Gly Leu Ile Arg Gln Ala Tyr Ala
305 310 315 320

Tyr Ile Leu Thr Ser Pro Gly Thr Pro Val Val Tyr Trp Pro His Met
325 330 335

Tyr Asp Trp Gly Tyr Gly Asp Phe Ile Arg Gln Leu Ile Gln Val Arg
340 345 350

Arg Thr Ala Gly Val Arg Ala Asp Ser Ala Ile Ser Phe His Ser Gly
355 360 365

Tyr Ser Gly Leu Val Ala Thr Val Ser Gly Ser Gln Gln Thr Leu Val
370 375 380

Val Ala Leu Asn Ser Asp Leu Ala Asn Pro Gly Gln Val Ala Ser Gly
385 390 395 400

Ser Phe Ser Glu Ala Val Asn Ala Ser Asn Gly Gln Val Arg Val Trp
405 410 415

Arg Ser Gly Ser Gly Asp Gly Gly Gly Asn Asp Gly Gly
420 425

<210> SEQ ID NO 14
<211> LENGTH: 429
<212> TYPE: PRT
<213> ORGANISM: Pseudomonas saccharophila

<400> SEQUENCE: 14

Asp Gln Ala Gly Lys Ser Pro Ala Gly Val Arg Tyr His Gly Gly Asp
1 5 10 15

Glu Ile Ile Leu Gln Gly Phe His Trp Asn Val Val Arg Glu Ala Pro
20 25 30

Asn Asn Trp Tyr Asn Ile Leu Arg Gln Gln Ala Ser Thr Ile Ala Ala
35 40 45

Asp Gly Phe Ser Ala Ile Trp Met Pro Val Pro Trp Arg Asp Phe Ser
50 55 60

Ser Trp Thr Asp Pro Gly Lys Ser Gly Gly Gly Glu Gly Tyr Phe Trp
65 70 75 80

His Asp Phe Asn Lys Asn Gly Arg Tyr Gly Ser Asp Ala Gln Leu Arg
85 90 95

Gln Ala Ala Gly Ala Leu Gly Gly Ala Gly Val Lys Val Leu Tyr Asp
100 105 110

Val Val Pro Asn His Met Asn Arg Asp Tyr Pro Asp Lys Glu Ile Asn
115 120 125

Leu Pro Ala Gly Gln Arg Phe Trp Arg Asn Asp Cys Pro Asp Pro Gly
130 135 140

Asn Tyr Pro Asn Asp Cys Asp Asp Gly Asp Arg Phe Leu Gly Gly Glu
145 150 155 160

Ser Asp Leu Asn Thr Gly His Pro Gln Ile Tyr Gly Met Phe Arg Asp
165 170 175

Glu Phe Thr Asn Leu Arg Ser Gly Tyr Gly Ala Gly Gly Phe Arg Phe
180 185 190

Asp Phe Val Arg Gly Tyr Ala Pro Glu Arg Val Asp Ser Trp Met Ser
195 200 205

Asp Ser Ala Asp Ser Ser Phe Cys Val Gly Glu Leu Trp Lys Ala Pro
210 215 220

Ser Glu Tyr Pro Ser Trp Asp Trp Arg Asn Thr Ala Ser Trp Gln Gln
225 230 235 240

Ile Ile Lys Asp Trp Ser Asp Arg Ala Lys Cys Pro Val Phe Asp Phe
245 250 255

Ala Leu Lys Glu Arg Met Gln Asn Gly Ser Val Ala Asp Trp Lys His
260 265 270

Gly Leu Asn Gly Asn Pro Asp Pro Arg Trp Arg Glu Val Ala Val Thr
275 280 285

Phe Val Asp Asn His Asp Thr Gly Tyr Ser Pro Gly Gln Asn Gly Gly
290 295 300

Gln His Leu Trp Ala Leu Gln Asp Gly Leu Ile Arg Gln Ala Tyr Ala
305 310 315 320

Tyr Ile Leu Thr Ser Pro Gly Thr Pro Val Val Tyr Trp Pro His Met
325 330 335

```
Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 15
<211> LENGTH: 429
<212> TYPE: PRT
<213> ORGANISM: Pseudomonas saccharophila

<400> SEQUENCE: 15

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asn Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Pro Gly Arg Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285
```

```
Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 16
<211> LENGTH: 429
<212> TYPE: PRT
<213> ORGANISM: Pseudomonas saccharophila

<400> SEQUENCE: 16

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asn Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Pro Gly Arg Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240
```

```
Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425
```

<210> SEQ ID NO 17
<211> LENGTH: 527
<212> TYPE: PRT
<213> ORGANISM: Pseudomonas stutzeri

<400> SEQUENCE: 17

```
Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asn Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Pro Ser Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190
```

```
Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 18
<211> LENGTH: 527
<212> TYPE: PRT
<213> ORGANISM: Pseudomonas stutzeri

<400> SEQUENCE: 18

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
            20                  25                  30

Asn Asn Trp Tyr Asn Ile Leu Arg Gln Gln Ala Ala Thr Ile Ala Ala
        35                  40                  45
```

-continued

```
Asp Gly Phe Ser Ala Ile Trp Met Pro Val Pro Trp Arg Asp Phe Ser
     50                  55                  60

Ser Trp Ser Asp Pro Ser Arg Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480
```

-continued

Ile Ala Leu Pro Ala Gly Gln Asn Glu Glu Trp Lys Cys Leu Ile Arg
485 490 495

Asn Glu Ala Asn Ala Thr Gln Val Arg Gln Trp Gln Gly Gly Ala Asn
500 505 510

Asn Ser Leu Thr Pro Ser Glu Gly Ala Thr Thr Val Gly Arg Leu
515 520 525

<210> SEQ ID NO 19
<211> LENGTH: 527
<212> TYPE: PRT
<213> ORGANISM: Pseudomonas stutzeri

<400> SEQUENCE: 19

Asp Gln Ala Gly Lys Ser Pro Asn Ala Val Arg Tyr His Gly Gly Asp
1 5 10 15

Glu Ile Ile Leu Gln Gly Phe His Trp Asn Val Val Arg Glu Ala Pro
20 25 30

Asn Asn Trp Tyr Asn Ile Leu Arg Gln Gln Ala Ala Thr Ile Ala Ala
35 40 45

Asp Gly Phe Ser Ala Ile Trp Met Pro Val Pro Trp Arg Asp Phe Ser
50 55 60

Ser Trp Ser Asp Pro Ser Arg Ser Gly Gly Gly Glu Gly Tyr Phe Trp
65 70 75 80

His Asp Phe Asn Lys Asn Ser Arg Tyr Gly Ser Asp Ala Gln Leu Arg
85 90 95

Gln Ala Ala Ser Ala Leu Gly Gly Ala Gly Val Lys Val Leu Tyr Asp
100 105 110

Val Val Pro Asn His Met Asn Arg Asp Tyr Pro Asp Lys Glu Ile Asn
115 120 125

Leu Pro Ala Gly Gln Arg Phe Trp Arg Asn Asp Cys Pro Asp Pro Gly
130 135 140

Asn Tyr Pro Asn Asp Cys Asp Asp Gly Asp Arg Phe Leu Gly Gly Asp
145 150 155 160

Ala Asp Leu Asn Thr Gly His Pro Gln Val Tyr Gly Met Phe Arg Asp
165 170 175

Glu Phe Thr Asn Leu Arg Ser Gln Tyr Gly Ala Gly Gly Phe Arg Phe
180 185 190

Asp Phe Val Arg Gly Tyr Ala Pro Glu Arg Val Asn Ser Trp Met Thr
195 200 205

Asp Ser Ala Asp Asn Ser Phe Cys Val Gly Glu Leu Trp Lys Ala Pro
210 215 220

Ser Glu Tyr Pro Asn Trp Asp Trp Arg Asn Thr Ala Ser Trp Gln Gln
225 230 235 240

Ile Ile Lys Asp Trp Ser Asp Arg Ala Lys Cys Pro Val Phe Asp Phe
245 250 255

Ala Leu Lys Glu Arg Met Gln Asn Gly Ser Ile Ala Asp Trp Lys His
260 265 270

Gly Leu Asn Gly Asn Pro Asp Pro Arg Trp Arg Glu Val Ala Val Thr
275 280 285

Phe Val Asp Asn His Asp Thr Gly Tyr Ser Pro Gly Gln Asn Gly Gly
290 295 300

Gln His Leu Trp Ala Leu Gln Asp Gly Leu Ile Arg Gln Ala Tyr Ala
305 310 315 320

Tyr Ile Leu Thr Ser Pro Gly Thr Pro Val Val Tyr Trp Pro His Met
325 330 335

```
Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525
```

<210> SEQ ID NO 20
<211> LENGTH: 429
<212> TYPE: PRT
<213> ORGANISM: Pseudomonas saccharophila

<400> SEQUENCE: 20

```
Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asn Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Gly Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190
```

```
Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 21
<211> LENGTH: 429
<212> TYPE: PRT
<213> ORGANISM: Pseudomonas saccharophila

<400> SEQUENCE: 21

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Pro Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140
```

```
Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 22
<211> LENGTH: 429
<212> TYPE: PRT
<213> ORGANISM: Pseudomonas saccharophila

<400> SEQUENCE: 22

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Pro Gly Arg Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95
```

```
Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425
```

<210> SEQ ID NO 23
<211> LENGTH: 429
<212> TYPE: PRT
<213> ORGANISM: Pseudomonas saccharophila

<400> SEQUENCE: 23

```
Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asp Trp Tyr Asn Ile Leu Arg Gln Gln Ala Ser Thr Ile Ala Ala
         35                  40                  45
```

```
Asp Gly Phe Ser Ala Ile Trp Met Pro Val Pro Trp Arg Asp Phe Ser
     50                  55                  60

Ser Trp Thr Asp Pro Gly Arg Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425
```

```
<210> SEQ ID NO 24
<211> LENGTH: 527
<212> TYPE: PRT
<213> ORGANISM: Pseudomonas stutzeri

<400> SEQUENCE: 24
```

-continued

Asp Gln Ala Gly Lys Ser Pro Asn Ala Val Arg Tyr His Gly Gly Asp
1 5 10 15

Glu Ile Ile Leu Gln Gly Phe His Trp Asn Val Val Arg Glu Ala Pro
20 25 30

Tyr Asp Trp Tyr Asn Ile Leu Arg Gln Gln Ala Ala Thr Ile Ala Ala
35 40 45

Asp Gly Phe Ser Ala Ile Trp Met Pro Val Pro Trp Arg Asp Phe Ser
50 55 60

Ser Trp Ser Asp Pro Ser Lys Ser Gly Gly Gly Glu Gly Tyr Phe Trp
65 70 75 80

His Asp Phe Asn Lys Asn Gly Arg Tyr Gly Ser Asp Ala Gln Leu Arg
85 90 95

Gln Ala Ala Ser Ala Leu Gly Gly Ala Gly Val Lys Val Leu Tyr Asp
100 105 110

Val Val Pro Asn His Met Asn Arg Asp Tyr Pro Asp Lys Glu Ile Asn
115 120 125

Leu Pro Ala Gly Gln Arg Phe Trp Arg Asn Asp Cys Pro Asp Pro Gly
130 135 140

Asn Tyr Pro Asn Asp Cys Asp Asp Gly Asp Arg Phe Leu Gly Gly Asp
145 150 155 160

Ala Asp Leu Asn Thr Gly His Pro Gln Val Tyr Gly Met Phe Arg Asp
165 170 175

Glu Phe Thr Asn Leu Arg Ser Gln Tyr Gly Ala Gly Gly Phe Arg Phe
180 185 190

Asp Phe Val Arg Gly Tyr Ala Pro Glu Arg Val Asn Ser Trp Met Thr
195 200 205

Asp Ser Ala Asp Asn Ser Phe Cys Val Gly Glu Leu Trp Lys Ala Pro
210 215 220

Ser Glu Tyr Pro Asn Trp Asp Trp Arg Asn Thr Ala Ser Trp Gln Gln
225 230 235 240

Ile Ile Lys Asp Trp Ser Asp Arg Ala Lys Cys Pro Val Phe Asp Phe
245 250 255

Ala Leu Lys Glu Arg Met Gln Asn Gly Ser Ile Ala Asp Trp Lys His
260 265 270

Gly Leu Asn Gly Asn Pro Asp Pro Arg Trp Arg Glu Val Ala Val Thr
275 280 285

Phe Val Asp Asn His Asp Thr Gly Tyr Ser Pro Gly Gln Asn Gly Gly
290 295 300

Gln His Leu Trp Ala Leu Gln Asp Gly Leu Ile Arg Gln Ala Tyr Ala
305 310 315 320

Tyr Ile Leu Thr Ser Pro Gly Thr Pro Val Val Tyr Trp Pro His Met
325 330 335

Tyr Asp Trp Gly Tyr Gly Asp Phe Ile Arg Gln Leu Ile Gln Val Arg
340 345 350

Arg Ala Ala Gly Val Arg Ala Asp Ser Ala Ile Ser Phe His Ser Gly
355 360 365

Tyr Ser Gly Leu Val Ala Thr Val Ser Gly Ser Gln Gln Thr Leu Val
370 375 380

Val Ala Leu Asn Ser Asp Leu Gly Asn Pro Gly Gln Val Ala Ser Gly
385 390 395 400

Ser Phe Ser Glu Ala Val Asn Ala Ser Asn Gly Gln Val Arg Val Trp
405 410 415

Arg Ser Gly Thr Gly Ser Gly Gly Gly Glu Pro Gly Ala Leu Val Ser

```
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 25
<211> LENGTH: 527
<212> TYPE: PRT
<213> ORGANISM: Pseudomonas stutzeri

<400> SEQUENCE: 25

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
            20                  25                  30

Tyr Asp Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Pro Ser Arg Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
```

```
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 26
<211> LENGTH: 527
<212> TYPE: PRT
<213> ORGANISM: Pseudomonas stutzeri

<400> SEQUENCE: 26

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asp Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Pro Ser Arg Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
```

```
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525
```

<210> SEQ ID NO 27
<211> LENGTH: 429
<212> TYPE: PRT
<213> ORGANISM: Pseudomonas saccharophila

```
<400> SEQUENCE: 27

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Gly Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415
```

-continued

```
Arg Ser Gly Ser Gly Asp Gly Gly Gly Asn Asp Gly Gly
            420                 425


<210> SEQ ID NO 28
<211> LENGTH: 429
<212> TYPE: PRT
<213> ORGANISM: Pseudomonas saccharophila

<400> SEQUENCE: 28

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Pro Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365
```

```
Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 29
<211> LENGTH: 429
<212> TYPE: PRT
<213> ORGANISM: Pseudomonas saccharophila

<400> SEQUENCE: 29

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
     50                  55                  60

Ser Trp Thr Asp Pro Gly Arg Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320
```

```
Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 30
<211> LENGTH: 429
<212> TYPE: PRT
<213> ORGANISM: Pseudomonas saccharophila

<400> SEQUENCE: 30

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
     50                  55                  60

Ser Trp Thr Asp Pro Gly Arg Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270
```

-continued

```
Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425


<210> SEQ ID NO 31
<211> LENGTH: 527
<212> TYPE: PRT
<213> ORGANISM: Pseudomonas stutzeri

<400> SEQUENCE: 31

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
     50                  55                  60

Ser Trp Ser Asp Pro Ser Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220
```

```
Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525
```

<210> SEQ ID NO 32
<211> LENGTH: 527
<212> TYPE: PRT
<213> ORGANISM: Pseudomonas stutzeri

<400> SEQUENCE: 32

```
Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Pro Ser Arg Ser Gly Gly Gly Glu Gly Tyr Phe Trp
 65                  70                  75                  80
```

-continued

```
His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510
```

```
Asn Ser Leu Thr Pro Ser Glu Gly Ala Thr Thr Val Gly Arg Leu
        515                 520                 525


<210> SEQ ID NO 33
<211> LENGTH: 527
<212> TYPE: PRT
<213> ORGANISM: Pseudomonas stutzeri

<400> SEQUENCE: 33

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Pro Ser Arg Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365
```

```
Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 34
<211> LENGTH: 429
<212> TYPE: PRT
<213> ORGANISM: Pseudomonas saccharophila

<400> SEQUENCE: 34

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220
```

Ser Glu Tyr Pro Ser Trp Asp Trp Arg Asn Thr Ala Ser Trp Gln Gln
225 230 235 240

Ile Ile Lys Asp Trp Ser Asp Arg Ala Lys Cys Pro Val Phe Asp Phe
245 250 255

Ala Leu Lys Glu Arg Met Gln Asn Gly Ser Val Ala Asp Trp Lys His
260 265 270

Gly Leu Asn Gly Asn Pro Asp Pro Arg Trp Arg Glu Val Ala Val Thr
275 280 285

Phe Val Asp Asn His Asp Thr Gly Tyr Ser Pro Gly Gln Asn Gly Gly
290 295 300

Gln His Leu Trp Ala Leu Gln Asp Gly Leu Ile Arg Gln Ala Tyr Ala
305 310 315 320

Tyr Ile Leu Thr Ser Pro Gly Thr Pro Val Val Tyr Trp Pro His Met
325 330 335

Tyr Asp Trp Gly Tyr Gly Asp Phe Ile Arg Gln Leu Ile Gln Val Arg
340 345 350

Arg Thr Ala Gly Val Arg Ala Asp Ser Ala Ile Ser Phe His Ser Gly
355 360 365

Tyr Ser Gly Leu Val Ala Thr Val Ser Gly Ser Gln Gln Thr Leu Val
370 375 380

Val Ala Leu Asn Ser Asp Leu Ala Asn Pro Gly Gln Val Ala Ser Gly
385 390 395 400

Ser Phe Ser Glu Ala Val Asn Ala Ser Asn Gly Gln Val Arg Val Trp
405 410 415

Arg Ser Gly Ser Gly Asp Gly Gly Gly Asn Asp Gly Gly
420 425

<210> SEQ ID NO 35
<211> LENGTH: 530
<212> TYPE: PRT
<213> ORGANISM: Pseudomonas saccharophila

<400> SEQUENCE: 35

Asp Gln Ala Gly Lys Ser Pro Ala Gly Val Arg Tyr His Gly Gly Asp
1 5 10 15

Glu Ile Ile Leu Gln Gly Phe His Trp Asn Val Val Arg Glu Ala Pro
20 25 30

Tyr Asn Trp Tyr Asn Ile Leu Arg Gln Gln Ala Ser Thr Ile Ala Ala
35 40 45

Asp Gly Phe Ser Ala Ile Trp Met Pro Val Pro Trp Arg Asp Phe Ser
50 55 60

Ser Trp Thr Asp Pro Gly Lys Ser Gly Gly Gly Glu Gly Tyr Phe Trp
65 70 75 80

His Asp Phe Asn Lys Asn Gly Arg Tyr Gly Ser Asp Ala Gln Leu Arg
85 90 95

Gln Ala Ala Gly Ala Leu Gly Gly Ala Gly Val Lys Val Leu Tyr Asp
100 105 110

Val Val Pro Asn His Met Asn Arg Gly Tyr Pro Asp Lys Glu Ile Asn
115 120 125

Leu Pro Ala Gly Gln Arg Phe Trp Arg Asn Asp Cys Pro Asp Pro Gly
130 135 140

Asn Tyr Pro Asn Asp Cys Asp Asp Gly Asp Arg Phe Leu Gly Gly Glu
145 150 155 160

Ser Asp Leu Asn Thr Gly His Pro Gln Ile Tyr Gly Met Phe Arg Asp
165 170 175

```
Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Ala Gly Ala Ser Thr Ser Gly
        515                 520                 525

Ser Phe
    530


<210> SEQ ID NO 36
<211> LENGTH: 480
<212> TYPE: PRT
<213> ORGANISM: Pseudomonas saccharophila

<400> SEQUENCE: 36

Asp Gln Ala Gly Lys Ser Pro Ala Gly Val Arg Tyr His Gly Gly Asp
  1               5                  10                  15
```

```
Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Pro Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly Glu Gly Gly
            420                 425                 430

Leu Val Asn Val Asn Phe Arg Cys Asp Asn Gly Val Thr Gln Met Gly
```

```
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480


<210> SEQ ID NO 37
<211> LENGTH: 480
<212> TYPE: PRT
<213> ORGANISM: Pseudomonas saccharophila

<400> SEQUENCE: 37

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Pro Gly Lys Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
```

```
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480


<210> SEQ ID NO 38
<211> LENGTH: 527
<212> TYPE: PRT
<213> ORGANISM: Pseudomonas saccharophila

<400> SEQUENCE: 38

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
     50                  55                  60

Ser Trp Ser Asp Pro Ser Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
```

```
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 39
<211> LENGTH: 527
<212> TYPE: PRT
<213> ORGANISM: Pseudomonas saccharophila

<400> SEQUENCE: 39

Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Pro Ser Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
```

-continued

```
        100                 105                 110

Val Val Pro Asn His Met Asn Arg Asp Tyr Pro Asp Lys Glu Ile Asn
    115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525
```

<210> SEQ ID NO 40
<211> LENGTH: 527
<212> TYPE: PRT
<213> ORGANISM: Pseudomonas saccharophila

<400> SEQUENCE: 40

```
Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Pro Ser Lys Ser Gly Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380
```

-continued

```
Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525


<210> SEQ ID NO 41
<211> LENGTH: 21
<212> TYPE: PRT
<213> ORGANISM: Pseudomonas saccharophila

<400> SEQUENCE: 41

Met Ser His Ile Leu Arg Ala Ala Val Leu Ala Ala Val Leu Leu Pro
  1               5                  10                  15

Phe Pro Ala Leu Ala
            20


<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

atgacgaggt ccttgttttt c                                                21


<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

cgctagtcgt ccatgtcg                                                    18


<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

gccatggatc aggccggcaa gagcccg                                          27
```

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
tggatcctca gaacgagccg ctggt 25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
gaattcagcc gccgtcattc ccgcc 25

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
agatttacgg catgtttcgc 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
tagccgctat ggaagctgat 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
tgaccttcgt cgacaaccac 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
gatagctgct ggtgacggtc 20

<210> SEQ ID NO 51

<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
ctgccggccg gccagcgctt ctggcg 26

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 52
cgccagaagc gctggccggc cggcag 26

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
gacggtgacc gcttcctggg cggcgagtcg 30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
cgactcgccg cccaggaagc ggtcaccgtc 30

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
ggcgagctgt ggaaagcccc ttctgaatat ccg 33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
cggatattca gaaggggctt tccacagctc gcc 33

<210> SEQ ID NO 57
<211> LENGTH: 31
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 57
gaacggcggc cagcacctgt gggcgctgca g 31

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
ctgcagcgcc cacaggtgct ggccgccgtt c 31

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
gtactggccg cacatgtacg actggggcta cggcgaattc atc 43

<210> SEQ ID NO 60
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
gatgaattcg ccgtagcccc agtcgtacat gtgcggccag tac 43

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
gcgaagcgcc ctacaactgg tacaac 26

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
ccgacggcgg caggtccggc g 21

<210> SEQ ID NO 63
<211> LENGTH: 25
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 63
caagaacagc cgctacggca gcgac 25

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
cacatgaacc gcgactaccc ggacaag 27

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
ctgccggccg gccagcgctt ctggcg 26

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
cgcaacgact gcgccgaccc ggg 23

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
gacggtgacc gcttcctggg cggcgagtcg 30

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
cgcgacgagt ttaccaacct gcg 23

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide -continued

```
<400> SEQUENCE: 69

ggcgagctgt ggaaagcccc ttctgaatat ccg                              33


<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70

gaacggcggc cagcacctgt gggcgctgca g                                31


<210> SEQ ID NO 71
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71

gtactggccg cacatgtacg actggggcta cggcgaattc atc                   43


<210> SEQ ID NO 72
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

gtactggccg cacatgtacg actggggcta cggc                             34
```